(12) United States Patent
Sleeman et al.

(10) Patent No.: US 8,354,103 B2
(45) Date of Patent: Jan. 15, 2013

(54) HUMAN ANTIBODIES TO HUMAN ANGIOPOIETIN-LIKE PROTEIN 4

(75) Inventors: Mark W. Sleeman, Mahopac, NY (US); Viktoria Gusarova, Springfield, NJ (US); Jee H. Kim, White Plains, NY (US); Gang Chen, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/977,361

(22) Filed: Dec. 23, 2010

(65) Prior Publication Data
US 2011/0159015 A1  Jun. 30, 2011

Related U.S. Application Data

(60) Provisional application No. 61/356,126, filed on Jun. 18, 2010, provisional application No. 61/349,273, filed on May 28, 2010, provisional application No. 61/328,316, filed on Apr. 27, 2010, provisional application No. 61/306,359, filed on Feb. 19, 2010, provisional application No. 61/290,092, filed on Dec. 24, 2009.

(51) Int. Cl.
*A61K 39/395* (2006.01)
*C07K 16/28* (2006.01)

(52) U.S. Cl. ............... 424/130.1; 530/387.1; 530/388.1; 530/388.22

(58) Field of Classification Search .................. None
See application file for complete search history.

(56) References Cited

U.S. PATENT DOCUMENTS
7,655,762 B2   2/2010   Lee et al.

FOREIGN PATENT DOCUMENTS
WO   WO 2006/074228 A1   7/2006
WO   WO 2007/109307 A2   9/2007

OTHER PUBLICATIONS

Yoshida K., et al., 2002. Angiopoietin-like protein 4 is a potent hyperlipidemia-inducing factor in mice and inhibitor of lipoprotein lipase. J Lipid Res. 43:1770-1772.
Ge H., et al., 2004. Oligomerization and Regulated Proteolytic Processing of Angiopoitin-like Protein 4. J Biol Chem. 279(3):2038-2045.
Ge H., et al., 2005. Differential regulation and properties of angiopoietin-like proteins 3 and 4. J Lipid Res. 46:1484-1490.
Ono M., et al., 2003. Protein Region Important for Regulation of Lipid Metabolism in Angiopoitin-like 3 (ANGPTL3). J Biol Chem. 278(43):41804-41809.

*Primary Examiner* — Marianne P Allen
(74) *Attorney, Agent, or Firm* — Christopher B. Westberg

(57) ABSTRACT

A fully human antibody or antigen-binding fragment of a human antibody that specifically binds and inhibits human angiopoietin-like protein 4 (hANGPTL4) is provided. The human anti-hANGPTL4 antibodies are useful in treating diseases or disorders associated with ANGPTL4, such as hyperlipidemia, hyperlipoproteinemia and dyslipidemia, including hypertriglyceridemia, hypercholesterolemia, chylomicronemia, and so forth. Furthermore, the anti-hANGPTL4 antibodies can be administered to a subject in need thereof to prevent or treat diseases or disorders, for which abnormal lipid metabolism is a risk factor. Such diseases or disorders include cardiovascular diseases, such as atherosclerosis and coronary artery diseases; acute pancreatitis; nonalcoholic steatohepatitis (NASH); diabetes; obesity; and the like.

6 Claims, 7 Drawing Sheets

HCDR

```
                              20                              40
H1H268P HCVR (SEQ ID NO:42)   QVQLQESGAGLLKPSETLSLTCTVYGGSFSIHHWTWIRHPPGKGL
H1H284P HCVR (SEQ ID NO:90)   QVQLVESGGGVVQPGRSLRLSCAASGFTFSSYGMHWVRQAPGKGL
H1H291P HCVR (SEQ ID NO:138)  EVQLVESGGGLVQPGGSLRLSCAASGFTFSSYDMHWVRQLGKGL
H1H292P HCVR (SEQ ID NO:162)  EVQLVESGGGLVQPGGSLRLSCVASGFTFSSYDMHWVRQLPGKGL 60                              80
H1H268P HCVR (SEQ ID NO:42)   EWIGEINHRG-STNYNPSLKSRVTISIDTSKNQFSLKLSAVTAAD
H1H284P HCVR (SEQ ID NO:90)   EWMAVISFDGGNKNNADSVKGRFTISRDNSKNTLYLQMNSLRAED
H1H291P HCVR (SEQ ID NO:138)  EWVSAIGSAG-DTYYPGSVKGRFTISRDNAKSSLFLHMNSLRAGD
H1H292P HCVR (SEQ ID NO:162)  EWVSAIGVAG-DTYYPASVKGRFTISRENAKNSLYLQMNSLRAGD 100                             120
H1H268P HCVR (SEQ ID NO:42)   TAVYYC ARG--LREFLDWLSSYF-DY WGQGTLVTVSSS
H1H284P HCVR (SEQ ID NO:90)   TAVYYC AKEGDRSGHPYFYYYGLDV WGQGTTVTVSSS
H1H291P HCVR (SEQ ID NO:138)  TALYYC ARGD--SRNYFVGDYF-DY WGQGTLVTVSSS
H1H292P HCVR (SEQ ID NO:162)  TAVYYC ARGD--SGNYYDGDYF-DF WGQGTLVTVSSS
```

Fig. 1

LCDR

```
                                              10              20              30          40
H1H268P LCVR (SEQ ID NO:44)   D I Q M T Q S P S S L S A S V G D R V T I T C R A S Q G I S D Y L A W Y Q Q K P
H1H284P LCVR (SEQ ID NO:92)   D I Q L T Q S P S F L S A S V G D R V T I T C R A S Q G I S S Y L A W Y Q Q K P
H1H291P LCVR (SEQ ID NO:140)  D I Q M T Q S P S T L S A S I G D R V T I T C W A S Q S I S S W L A W Y Q Q K P
H1H292P LCVR (SEQ ID NO:164)  D I Q M T Q S P S T L S A S V G D R V T I T C R A S Q S I N R W L A W Y Q Q K P 50              60              70          80
H1H268P LCVR (SEQ ID NO:44)   G K V P N L L I Y A A S A L Q S G V P S R F S G S G S G T D F T L T I S S L Q P
H1H284P LCVR (SEQ ID NO:92)   G K A P K L L I Y A A S T L Q S G V P S R F S G S G S G T E T E F T L T I S S L Q P
H1H291P LCVR (SEQ ID NO:140)  G K A P K V L I Y K A S S L E A G V P S R F S G S G S G T E F T L T I S S L Q P
H1H292P LCVR (SEQ ID NO:164)  G K A P K V L I Y K A S N L E S G V P S R F S G S G S G T E F T L T I S S L Q P 90              100
H1H268P LCVR (SEQ ID NO:44)   E D V A T Y Y C Q N Y N T A P L T F G G G T K V E I K
H1H284P LCVR (SEQ ID NO:92)   E D F A T Y Y C Q Q L H S Y P L T F G G G T K V E I K
H1H291P LCVR (SEQ ID NO:140)  D D F A S Y Y C Q Q Y S S Y S R T F G Q G T K V E I K
H1H292P LCVR (SEQ ID NO:164)  D D F A T Y Y C Q Q Y D S Y F R T F G Q G T K V E I K
```

Fig. 2

```
                        SEQUENCE LISTING

<160> NUMBER OF SEQ ID NOS: 492

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1
caggtgcagc tggtgcagtc tgggggaggc ttggtgcagc ctgggggtc cctgagactc        60 tcctgtgcag cctctggatt cactttcagt agctacgaca tgcactgggt ccgccaagtt      120
gcaggaaaag gtctggagtg ggtctcagcc attggtactc tggtgacac atactatcca      180 gtctccgtga agggccgatt caccatctct agagaaaatg ccaagaactc cttgtatctt      240
cacatgaaca gcctgagagc cggggacacg gctgtgtatt tctgtgcaag aggagacagt      300
agaaactact acgttgggga ctactttgac tactggggcc agggaaccac ggtcaccgtc      360
tcctca                                                                 366

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Val Ala Gly Lys Gly Leu Glu Trp Val
        35                  40                  45

Ser Ala Ile Gly Thr Ala Gly Asp Thr Tyr Tyr Pro Val Ser Val Lys
    50                  55                  60

Gly Arg Phe Thr Ile Ser Arg Glu Asn Ala Lys Asn Ser Leu Tyr Leu
65                  70                  75                  80

His Met Asn Ser Leu Arg Ala Gly Asp Thr Ala Val Tyr Phe Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Thr Val Thr Val Ser Ser
        115                 120

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
```

```
ggattcactt tcagtagcta cgac                                              24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Tyr Asp
 1               5

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5

```
attggtactg ctggtgacac a                                                 21
```

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Gly Thr Ala Gly Asp Thr
 1               5

<210> SEQ ID NO 7
<211> LENGTH: 48
<212> TYPE: DNA
<213> ORGANISM: Artificial Sequence
<220> FEATURE:
<223> OTHER INFORMATION: Synthetic

<400> SEQUENCE: 7

```
gcaagaggag acagtagaaa ctactacgtt ggggactact ttgactac                    48
```

<210> SEQ ID NO 8
<211> LENGTH: 16
<212> TYPE: PRT
<213> ORGANISM: Artificial Sequence
<220> FEATURE:
<223> OTHER INFORMATION: Synthetic

<400> SEQUENCE: 8

Ala Arg Gly Asp Ser Arg Asn Tyr Tyr Val Gly Asp Tyr Phe Asp Tyr
 1               5                  10                  15

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9

```
gccatccaga tgacccagtc tccttccacc ctgtctgcat ctgtaggaga cagagtcacc       60
atcacttgcc gggccagtca gagtattagt aggtggttgg cctggtatca gcaaaaacca      120
```

```
gggaaagccc ctaaggtcct gatctatcag gcgtccaatt tagaaagtgg ggtcccatca    180
aggttcagcg gcagtggatc tgggacagaa ttcactctca ccatcagcag cctgcagcct    240
gatgattttg caacttatta ctgccaacag tatgatagtt attctcgggc gttcggccga    300
gggaccaagg tggaaatcaa a                                              321
```

```
<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10
```

Ala Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Val Leu Ile
        35                  40                  45

Tyr Gln Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Ser Arg
                85                  90                  95

Ala Phe Gly Arg Gly Thr Lys Val Glu Ile Lys
            100                 105

```
<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagtatta gtaggtgg                                                   18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12
```

Gln Ser Ile Ser Arg Trp
1               5

```
<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 caggcgtcc                                                              9

<210> SEQ ID NO 14
<211> LENGTH: 3
<212> TYPE: PRT
```

```
<213> ORGANISM: Artificial Sequence
<220> FEATURE:
<223> OTHER INFORMATION: Synthetic

<400> SEQUENCE: 14

Gln Ala Ser
  1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacagtatg atagttattc tcgggcg                                         27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Asp Ser Tyr Ser Arg Ala
  1               5

<210> SEQ ID NO 17
<211> LENGTH: 366
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaggc ttggtgcagc ctggggggtc cctgagactc      60
tcctgtgcag cctctggatt cactttcagt agctacgaca tgcactgggt ccgccaagtt     120
gcaggaaaag gtctggagtg gtctcagcc attggtactg ctggtgacac atactatcca     180
gtctccgtga agggccgatt caccatctct agagaaaatg ccaagaactc cttgtatctt     240
cacatgaaca gcctgagagc cggggacacg gctgtgtatt tctgtgcaag aggagacagt     300
agaaactact acgttgggga ctactttgac tactggggcc agggaaccct ggtcaccgtc     360
tcctca                                                                366

<210> SEQ ID NO 18
<211> LENGTH: 122
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met His Trp Val Arg Gln Val Ala Gly Lys Gly Leu Glu Trp Val
         35                  40                  45

Ser Ala Ile Gly Thr Ala Gly Asp Thr Tyr Tyr Pro Val Ser Val Lys
     50                  55                  60
```

Gly Arg Phe Thr Ile Ser Arg Glu Asn Ala Lys Asn Ser Leu Tyr Leu
 65                  70                  75                  80

His Met Asn Ser Leu Arg Ala Gly Asp Thr Ala Val Tyr Phe Cys Ala
                 85                  90                  95

Arg Gly Asp Ser Arg Asn Tyr Tyr Val Gly Asp Tyr Phe Asp Tyr Trp
            100                 105                 110

Gly Gln Gly Thr Leu Val Thr Val Ser Ser
        115                 120

<210> SEQ ID NO 19
<211> LENGTH: 321
<212> TYPE: DNA
<213> ORGANISM: Artificial Sequence
<220> FEATURE:
<223> OTHER INFORMATION: Synthetic

<400> SEQUENCE: 19
gacatccaga tgacccagtc tccttccacc ctgtctgcat ctgtaggaga cagagtcacc    60
atcacttgcc gggccagtca gagtattagt aggtggttgg cctggtatca gcaaaaacca   120
gggaaagccc ctaaggtcct gatctatcag gcgtccaatt tagaaagtgg ggtcccatca   180
aggttcagcg gcagtggatc tgggacagaa ttcactctca ccatcagcag cctgcagcct   240
gatgattttg caacttatta ctgccaacag tatgatagtt attctcgggc gttcggccga   300
gggaccaagg tggaaatcaa a                                            321

<210> SEQ ID NO 20
<211> LENGTH: 107
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Arg Trp
             20                  25                  30

Leu Ala Trp Tyr Gln Gln Lys Pro Gly Lys Ala Pro Lys Val Leu Ile
         35                  40                  45

Tyr Gln Ala Ser Asn Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Ser Tyr Ser Arg
                 85                  90                  95

Ala Phe Gly Arg Gly Thr Lys Val Glu Ile Lys
            100                 105

<210> SEQ ID NO 21
<211> LENGTH: 366
<212> TYPE: DNA
<213> ORGANISM: Artificial Sequence
<220> FEATURE:
<223> OTHER INFORMATION: Synthetic

<400> SEQUENCE: 21
gaggtgcagc tggtggagtc tgggggaggc ttggtacagc ctggggggtc cctgagactc    60
tcctgtgcag cctctggatt cactttcagt agctacgaca tgcactgggt ccgccaagct   120
acaggaaaag gtctggagtg ggtctcagct attggtactg ctggtgacac atactatcca   180

```
ggctccgtga agggccgatt caccatctcc agagaaaatg ccaagaactc cttgtatctt      240
caaatgaaca gcctgagagc cggggacacg gctgtgtatt actgtgcaag aggagacagt      300
agaaactact acgttgggga ctactttgac tactggggcc agggaaccct ggtcaccgtc      360
tcctca                                                                  366
```

<210> SEQ ID NO 22
<211> LENGTH: 122
<212> TYPE: PRT
<213> ORGANISM: Artificial Sequence
<220> FEATURE:
<223> OTHER INFORMATION: Synthetic

<400> SEQUENCE: 22

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Leu Val Thr Val Ser Ser
        115                 120
```

<210> SEQ ID NO 23
<211> LENGTH: 322
<212> TYPE: DNA
<213> ORGANISM: Artificial Sequence
<220> FEATURE:
<223> OTHER INFORMATION: Synthetic

<400> SEQUENCE: 23

```
gacatccaga tgacccagtc tccttccacc ctgtctgcat ctgtaggaga cagagtcacc       60
atcacttgcc gggccagtca gagtattagt aggtggttgg cctggtatca gcagaaacca      120
gggaaagccc ctaagctcct gatctatcag gcgtccagtt tagaaagtgg ggtcccatca      180
aggttcagcg gcagtggatc tgggacagaa ttcactctca ccatcagcag cctgcagcct      240
gatgattttg caacttatta ctgccaacag tatgatagtt attctcgggc gttcggccaa      300
gggaccaagg tggaaatcaa ac                                               322
```

<210> SEQ ID NO 24
<211> LENGTH: 107
<212> TYPE: PRT
<213> ORGANISM: Artificial Sequence
<220> FEATURE:
<223> OTHER INFORMATION: Synthetic

<400> SEQUENCE: 24

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Arg Trp
            20                  25                  30
```

Leu Ala Trp Tyr Gln Gln Lys Pro Gly Lys Ala Pro Lys Leu Leu Ile
            35                  40                  45

Tyr Gln Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Ser Tyr Ser Arg
                 85                  90                  95

Ala Phe Gly Gln Gly Thr Lys Val Glu Ile Lys
                100                 105

<210> SEQ ID NO 25
<211> LENGTH: 366
<212> TYPE: DNA
<213> ORGANISM: Artificial Sequence
<220> FEATURE:
<223> OTHER INFORMATION: Synthetic

<400> SEQUENCE: 25
caggtacagc tgcagcagtg gggcgcagga ctgttgaagc cttcggagac cctgtccctc      60
acctgcactg tctatggtgg atccttcagt attcatcact ggacctggat ccgccatccc     120
ccagggaagg gactggagtg gattggggag atcaatcatc gtggaagcac caactacaac     180
ccgtccctca gagtcgagt caccatatca atagacacgt ccaagaacca gttctccctg     240
aagctgagcg ctgtgaccgc cgcggacacg gctgtatatt actgtgcgag aggcttacga     300
tttttggact ggttatcgtc ctactttgac tactggggcc agggaaccac ggtcaccgtc     360
tcctca                                                                366

<210> SEQ ID NO 26
<211> LENGTH: 122
<212> TYPE: PRT
<213> ORGANISM: Artificial Sequence
<220> FEATURE:
<223> OTHER INFORMATION: Synthetic

<400> SEQUENCE: 26

Gln Val Gln Leu Gln Gln Trp Gly Ala Gly Leu Leu Lys Pro Ser Glu
  1               5                  10                  15

Thr Leu Ser Leu Thr Cys Thr Val Tyr Gly Gly Ser Phe Ser Ile His
             20                  25                  30

His Trp Thr Trp Ile Arg His Pro Pro Gly Lys Gly Leu Glu Trp Ile
         35                  40                  45

Gly Glu Ile Asn His Arg Gly Ser Thr Asn Tyr Asn Pro Ser Leu Lys
     50                  55                  60

Ser Arg Val Thr Ile Ser Ile Asp Thr Ser Lys Asn Gln Phe Ser Leu
 65                  70                  75                  80

Lys Leu Ser Ala Val Thr Ala Ala Asp Thr Ala Val Tyr Tyr Cys Ala
                 85                  90                  95

Arg Gly Leu Arg Phe Leu Asp Trp Leu Ser Ser Tyr Phe Asp Tyr Trp
                100                 105                 110

Gly Gln Gly Thr Thr Val Thr Val Ser Ser
            115                 120

<210> SEQ ID NO 27
<211> LENGTH: 24
<212> TYPE: DNA
<213> ORGANISM: Artificial Sequence
<220> FEATURE:

-continued

<223> OTHER INFORMATION: Synthetic

<400> SEQUENCE: 27
ggtggatcct tcagtattca tcac                                             24

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Gly Gly Ser Phe Ser Ile His His
 1               5

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
atcaatcatc gtggaagcac c                                                21

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Ile Asn His Arg Gly Ser Thr
 1               5

<210> SEQ ID NO 31
<211> LENGTH: 48
<212> TYPE: DNA
<213> ORGANISM: Artificial Sequence
<220> FEATURE:
<223> OTHER INFORMATION: Synthetic

<400> SEQUENCE: 31
gcgagaggct tacgattttt ggactggtta tcgtcctact ttgactac                   48

<210> SEQ ID NO 32
<211> LENGTH: 16
<212> TYPE: PRT
<213> ORGANISM: Artificial Sequence
<220> FEATURE:
<223> OTHER INFORMATION: Synthetic

<400> SEQUENCE: 32

Ala Arg Gly Leu Arg Phe Leu Asp Trp Leu Ser Ser Tyr Phe Asp Tyr
 1               5                  10                  15

<210> SEQ ID NO 33
<211> LENGTH: 321
<212> TYPE: DNA
<213> ORGANISM: Artificial Sequence
<220> FEATURE:
<223> OTHER INFORMATION: Synthetic

<400> SEQUENCE: 33
gacatccagt tgacccagtc tccatcctcc ctgtctgcat ctgtaggaga cagagtcacc      60

```
atcacttgcc gggcgagtca gggcattagc gattatttag cctggtatca gcagaaacca    120
gggaaagttc ctaacctcct gatctatgct gcgtccgctt tacaatcagg ggtcccatct    180
cgtttcagtg gcagtggatc tgggacagat ttcactctca ccatcagcag cctgcagcct    240
gaggatgttg caacttatta ctgtcaaaat tataacactg ccccgctcac tttcggcggg    300
gggaccaagg tggaaatcaa a                                              321
```

<210> SEQ ID NO 34
<211> LENGTH: 107
<212> TYPE: PRT
<213> ORGANISM: Artificial Sequence
<220> FEATURE:
<223> OTHER INFORMATION: Synthetic

<400> SEQUENCE: 34

```
Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asp Tyr
            20                  25                  30

Leu Ala Trp Tyr Gln Gln Lys Pro Gly Lys Val Pro Asn Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Thr Ala Pro Leu
                85                  90                  95

Thr Phe Gly Gly Gly Thr Lys Val Glu Ile Lys
            100                 105
```

<210> SEQ ID NO 35
<211> LENGTH: 18
<212> TYPE: DNA
<213> ORGANISM: Artificial Sequence
<220> FEATURE:
<223> OTHER INFORMATION: Synthetic

<400> SEQUENCE: 35

```
cagggcatta gcgattat                                                   18
```

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

```
Gln Gly Ile Ser Asp Tyr
 1               5
```

<210> SEQ ID NO 37
<211> LENGTH: 9
<212> TYPE: DNA
<213> ORGANISM: Artificial Sequence
<220> FEATURE:
<223> OTHER INFORMATION: Synthetic

<400> SEQUENCE: 37

```
gctgcgtcc                                                              9
```

```
<210> SEQ ID NO 38
<211> LENGTH: 3
<212> TYPE: PRT
<213> ORGANISM: Artificial Sequence
<220> FEATURE:
<223> OTHER INFORMATION: Synthetic

<400> SEQUENCE: 38

Ala Ala Ser
 1

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
caaaattata acactgcccc gctcact                                           27

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Gln Asn Tyr Asn Thr Ala Pro Leu Thr
 1               5

<210> SEQ ID NO 41
<211> LENGTH: 366
<212> TYPE: DNA
<213> ORGANISM: Artificial Sequence
<220> FEATURE:
<223> OTHER INFORMATION: Synthetic

<400> SEQUENCE: 41
caggtgcagc tgcaggagtc gggcgcagga ctgttgaagc cttcggagac cctgtccctc      60
acctgcactg tctatggtgg atccttcagt attcatcact ggacctggat ccgccatccc     120
ccagggaagg ggctggagtg gattggggag atcaatcatc gtggaagcac caactacaac     180
ccgtccctca agagtcgagt caccatatca atagacacgt ccaagaacca gttctccctg     240
aagctgagcg ctgtgaccgc cgcggacacg gctgtatatt actgtgcgag aggcttacga     300
tttttggact ggttatcgtc ctactttgac tactggggcc agggaaccct ggtcactgtc     360
tcctca                                                                366

<210> SEQ ID NO 42
<211> LENGTH: 122
<212> TYPE: PRT
<213> ORGANISM: Artificial Sequence
<220> FEATURE:
<223> OTHER INFORMATION: Synthetic

<400> SEQUENCE: 42

Gln Val Gln Leu Gln Glu Ser Gly Ala Gly Leu Leu Lys Pro Ser Glu
 1               5                  10                  15

Thr Leu Ser Leu Thr Cys Thr Val Tyr Gly Gly Ser Phe Ser Ile His
                20                  25                  30

His Trp Thr Trp Ile Arg His Pro Pro Gly Lys Gly Leu Glu Trp Ile
            35                  40                  45
```

```
Gly Glu Ile Asn His Arg Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ala Val Thr Ala Ala Asp Thr Ala Val Tyr Tyr Cys Ala
                85                  90                  95

Arg Gly Leu Arg Phe Leu Asp Trp Leu Ser Ser Tyr Phe Asp Tyr Trp
            100                 105                 110

Gly Gln Gly Thr Leu Val Thr Val Ser Ser
            115                 120
```

```
<210> SEQ ID NO 43
<211> LENGTH: 321
<212> TYPE: DNA
<213> ORGANISM: Artificial Sequence
<220> FEATURE:
<223> OTHER INFORMATION: Synthetic

<400> SEQUENCE: 43
gacatccaga tgacccagtc tccatcctcc ctgtctgcat ctgtaggaga cagagtcacc      60
atcacttgcc gggcgagtca gggcattagc gattatttag cctggtatca gcagaaacca     120
gggaaagttc ctaacctcct gatctatgct gcgtccgctt acaatcagg  gtcccatct     180 cgtttcagtg gcagtggatc tgggacagat ttcactctca ccatcagcag cctgcagcct    240
gaggatgttg caacttatta ctgtcaaaat tataacactg ccccgctcac tttcggcggg    300
gggaccaagg tggaaatcaa a                                              321
```

```
<210> SEQ ID NO 44
<211> LENGTH: 107
<212> TYPE: PRT
<213> ORGANISM: Artificial Sequence
<220> FEATURE:
<223> OTHER INFORMATION: Synthetic

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asp Tyr
            20                  25                  30

Leu Ala Trp Tyr Gln Gln Lys Pro Gly Lys Val Pro Asn Leu Leu Ile
        35                  40                  45

Tyr Ala Ala Ser Ala Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Asn Tyr Asn Thr Ala Pro Leu
                85                  90                  95

Thr Phe Gly Gly Gly Thr Lys Val Glu Ile Lys
            100                 105
```

```
<210> SEQ ID NO 45
<211> LENGTH: 366
<212> TYPE: DNA
<213> ORGANISM: Artificial Sequence
<220> FEATURE:
<223> OTHER INFORMATION: Synthetic

<400> SEQUENCE: 45
caggtgcagc tacagcagtg gggcgcagga ctgttgaagc cttcggagac cctgtccctc      60
```

```
acctgcgctg tctatggtgg atccttcagt attcatcact ggagctggat ccgccagccc    120
ccagggaagg ggctggagtg gattggggaa atcaatcatc gtggaagcac caactacaac    180
ccgtccctca agagtcgagt caccatatca gtagacacgt ccaagaacca gttctccctg    240
aagctgagct ctgtgaccgc cgcggacacg gctgtgtatt actgtgcgag aggcttacga    300
tttttggact ggttatcgtc ctactttgac tactggggcc agggaaccct ggtcaccgtc    360
tcctca                                                               366
```

<210> SEQ ID NO 46
<211> LENGTH: 122
<212> TYPE: PRT
<213> ORGANISM: Artificial Sequence
<220> FEATURE:
<223> OTHER INFORMATION: Synthetic

<400> SEQUENCE: 46

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Ile His
             20                  25                  30

His Trp Ser Trp Ile Arg Gln Pro Pro Gly Lys Gly Leu Glu Trp Ile
         35                  40                  45

Gly Glu Ile Asn His Arg Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Leu Arg Phe Leu Asp Trp Leu Ser Ser Tyr Phe Asp Tyr Trp
            100                 105                 110

Gly Gln Gly Thr Leu Val Thr Val Ser Ser
        115                 120
```

<210> SEQ ID NO 47
<211> LENGTH: 322
<212> TYPE: DNA
<213> ORGANISM: Artificial Sequence
<220> FEATURE:
<223> OTHER INFORMATION: Synthetic

<400> SEQUENCE: 47

```
gacatccaga tgacccagtc tccatcctcc ctgtctgcat ctgtaggaga cagagtcacc     60
atcacttgcc gggcgagtca gggcattagc gattatttag cctggtatca gcagaaacca    120
gggaaagttc ctaagctcct gatctatgct gcgtccactt tgcaatcagg ggtcccatct    180
cggttcagtg gcagtggatc tgggacagat ttcactctca ccatcagcag cctgcagcct    240
gaagatgttg caactattc tgtcaaaat taatactg ccccgctcac tttcggcgga    300
gggaccaagg tggagatcaa ac                                             322
```

<210> SEQ ID NO 48
<211> LENGTH: 107
<212> TYPE: PRT
<213> ORGANISM: Artificial Sequence
<220> FEATURE:
<223> OTHER INFORMATION: Synthetic

<400> SEQUENCE: 48

```
Asp Ile Gln Met Thr Gln Ser Pro Ser Ser Leu Ser Ala Ser Val Gly
  1               5                  10                  15
```

```
Asp Arg Val Thr Ile Thr Cys Arg Ala Ser Gln Gly Ile Ser Asp Tyr
             20                  25                  30

Leu Ala Trp Tyr Gln Gln Lys Pro Gly Lys Val Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Asn Tyr Asn Thr Ala Pro Leu
                 85                  90                  95

Thr Phe Gly Gly Gly Thr Lys Val Glu Ile Lys
            100                 105
```

<210> SEQ ID NO 49
<211> LENGTH: 366
<212> TYPE: DNA
<213> ORGANISM: Artificial Sequence
<220> FEATURE:
<223> OTHER INFORMATION: Synthetic

<400> SEQUENCE: 49

```
caggtgcagc tggtgcagtc tgggggaggc ttggtgcagc ctggggggtc cctgagactc      60
tcctgtgcag cctctggatt cactttcagt agctacgaca tgcactgggt ccgccaagtt     120
gcaggaaaag gtctggagtg ggtctcagcc attggtactg ctggtgacac atactatcca     180
gtctccgtga agggccgatt caccatctct agagaaaatg ccaagaactc cttgtatctt     240
cacatgaaca gcctgagagc cggggacacg gctgtgtatt tctgtgcaag aggagacagt     300
agaaactact acgttgggga ctactttgac tactggggcc agggaaccac ggtcaccgtc     360
tcctca                                                                 366
```

<210> SEQ ID NO 50
<211> LENGTH: 122
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asp Met His Trp Val Arg Gln Val Ala Gly Lys Gly Leu Glu Trp Val
         35                  40                  45

Ser Ala Ile Gly Thr Ala Gly Asp Thr Tyr Tyr Pro Val Ser Val Lys
 50                  55                  60

Gly Arg Phe Thr Ile Ser Arg Glu Asn Ala Lys Asn Ser Leu Tyr Leu
 65                  70                  75                  80

His Met Asn Ser Leu Arg Ala Gly Asp Thr Ala Val Tyr Phe Cys Ala
                 85                  90                  95

Arg Gly Asp Ser Arg Asn Tyr Tyr Val Gly Asp Tyr Phe Asp Tyr Trp
            100                 105                 110

Gly Gln Gly Thr Thr Val Thr Val Ser Ser
            115                 120
```

<210> SEQ ID NO 51
<211> LENGTH: 24

```
<212> TYPE: DNA
<213> ORGANISM: Artificial Sequence
<220> FEATURE:
<223> OTHER INFORMATION: Synthetic

<400> SEQUENCE: 51
ggattcactt tcagtagcta cgac                                         24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Tyr Asp
 1               5

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53
attggtactg ctggtgacac a                                            21

<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Ile Gly Thr Ala Gly Asp Thr
 1               5

<210> SEQ ID NO 55
<211> LENGTH: 48
<212> TYPE: DNA
<213> ORGANISM: Artificial Sequence
<220> FEATURE:
<223> OTHER INFORMATION: Synthetic

<400> SEQUENCE: 55
gcaagaggag acagtagaaa ctactacgtt ggggactact ttgactac               48

<210> SEQ ID NO 56
<211> LENGTH: 16
<212> TYPE: PRT
<213> ORGANISM: Artificial Sequence
<220> FEATURE:
<223> OTHER INFORMATION: Synthetic

<400> SEQUENCE: 56

Ala Arg Gly Asp Ser Arg Asn Tyr Tyr Val Gly Asp Tyr Phe Asp Tyr
 1               5                  10                  15

<210> SEQ ID NO 57
<211> LENGTH: 321
<212> TYPE: DNA
<213> ORGANISM: Artificial Sequence
<220> FEATURE:
<223> OTHER INFORMATION: Synthetic
```

-continued

```
<400> SEQUENCE: 57
gacatcgtga tgacccagtc tccttccacc ctgtctgcat ctgtaggaga cagagtcacc    60
atcacttgcc gggccagtca gagtattagt aggtggttgg cctggtatca gcaaaaacca   120
ggaaaagccc ctaaggtcct gatctataag gcgtctaatt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggagatcaa a                                             321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Val Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Val Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagagtatta gtaggtgg                                                  18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Ser Ile Ser Arg Trp
 1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61
``` aaggcgtct                                                                 9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Ala Ser
 1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atagttattc tcggacg                                            27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Ser Tyr Ser Arg Thr
 1               5

<210> SEQ ID NO 65
<211> LENGTH: 366
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtgcagc ctggggggtc cctgagactc        60
tcctgtgcag cctctggatt cactttcagt agctacgaca tgcactgggt ccgccaagtt       120
gcaggaaaag gtctggagtg ggtctcagcc attggtactg ctggtgacac atactatcca       180
gtctccgtga agggccgatt caccatctct agagaaaatg ccaagaactc cttgtatctt       240
cacatgaaca gcctgagagc cggggacacg gctgtgtatt tctgtgcaag aggagacagt       300
agaaactact acgttgggga ctactttgac tactggggcc agggaaccct ggtcaccgtc       360
tcctca                                                                 366

<210> SEQ ID NO 66
<211> LENGTH: 122
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
 1               5                  10                  15

Ser Leu Arg Leu Ser Cys Ala Ser Gly Phe Thr Phe Ser Ser Tyr
            20                  25                  30

Asp Met His Trp Val Arg Gln Val Ala Gly Lys Gly Leu Glu Trp Val
              35                  40                  45

Ser Ala Ile Gly Thr Ala Gly Asp Thr Tyr Tyr Pro Val Ser Val Lys
 50                  55                  60

Gly Arg Phe Thr Ile Ser Arg Glu Asn Ala Lys Asn Ser Leu Tyr Leu
 65                  70                  75                  80

His Met Asn Ser Leu Arg Ala Gly Asp Thr Ala Val Tyr Phe Cys Ala
              85                  90                  95

Arg Gly Asp Ser Arg Asn Tyr Tyr Val Gly Asp Tyr Phe Asp Tyr Trp
             100                 105                 110

Gly Gln Gly Thr Leu Val Thr Val Ser Ser
             115                 120

<210> SEQ ID NO 67
<211> LENGTH: 321
<212> TYPE: DNA
<213> ORGANISM: Artificial Sequence
<220> FEATURE:
<223> OTHER INFORMATION: Synthetic

<400> SEQUENCE: 67
gacatccaga tgacccagtc tccttccacc ctgtctgcat ctgtaggaga cagagtcacc     60
atcacttgcc gggccagtca gagtattagt aggtggttgg cctggtatca gcaaaaacca    120
ggaaaagccc ctaaggtcct gatctataag gcgtctaatt tagaaagtgg ggtcccatca    180
aggttcagcg gcagtggatc tgggacagaa ttcactctca ccatcagcag cctgcagcct    240
gatgattttg caacttatta ctgccaacag tataatagtt attctcggac gttcggccaa    300
gggaccaagg tggaaatcaa a                                              321

<210> SEQ ID NO 68
<211> LENGTH: 107
<212> TYPE: PRT
<213> ORGANISM: Artificial Sequence
<220> FEATURE:
<223> OTHER INFORMATION: Synthetic

<400> SEQUENCE: 68

Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Ser Arg Trp
             20                  25                  30

Leu Ala Trp Tyr Gln Gln Lys Pro Gly Lys Ala Pro Lys Val Leu Ile
         35                  40                  45

Tyr Lys Ala Ser Asn Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Arg
             85                  90                  95

Thr Phe Gly Gln Gly Thr Lys Val Glu Ile Lys
            100                 105

<210> SEQ ID NO 69
<211> LENGTH: 366
<212> TYPE: DNA
<213> ORGANISM: Artificial Sequence
<220> FEATURE:
<223> OTHER INFORMATION: Synthetic

<400> SEQUENCE: 69

```
gaggtgcagc tggtggagtc tggggggaggc ttggtacagc ctgggggggtc cctgagactc    60 tcctgtgcag cctctggatt cactttcagt agctacgaca tgcactgggt ccgccaagct   120
acaggaaaag gtctggagtg ggtctcagct attggtactg ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag aggagacagt   300
agaaactact acgttgggga ctactttgac tactggggcc agggaaccct ggtcaccgtc   360
tcctca                                                              366
```

```
<210> SEQ ID NO 70
<211> LENGTH: 122
<212> TYPE: PRT
<213> ORGANISM: Artificial Sequence
<220> FEATURE:
<223> OTHER INFORMATION: Synthetic

<400> SEQUENCE: 70

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
         35                  40                  45

Ser Ala Ile Gly Thr Ala Gly Asp Thr Tyr Tyr Pro Gly Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Gly Asp Ser Arg Asn Tyr Tyr Val Gly Asp Tyr Phe Asp Tyr Trp
            100                 105                 110

Gly Gln Gly Thr Leu Val Thr Val Ser Ser
        115                 120
```

```
<210> SEQ ID NO 71
<211> LENGTH: 322
<212> TYPE: DNA
<213> ORGANISM: Artificial Sequence
<220> FEATURE:
<223> OTHER INFORMATION: Synthetic

<400> SEQUENCE: 71
gacatccaga tgacccagtc tccttccacc ctgtctgcat ctgtaggaga cagagtcacc    60
atcacttgcc gggccagtca gagtattagt aggtggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attctcggac gttcggccaa   300
gggaccaagg tggaaatcaa ac                                            322
```

```
<210> SEQ ID NO 72
<211> LENGTH: 107
<212> TYPE: PRT
<213> ORGANISM: Artificial Sequence
<220> FEATURE:
<223> OTHER INFORMATION: Synthetic

<400> SEQUENCE: 72
```

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 73
<211> LENGTH: 378
<212> TYPE: DNA
<213> ORGANISM: Artificial Sequence
<220> FEATURE:
<223> OTHER INFORMATION: Synthetic

<400> SEQUENCE: 73
gaggtgcagc tggtgcagtc tggggggaggc gtggtccagc ctgggaggtc cctgagactc      60
tcctgtgcag cctctggatt caccttcagt agttatggca tgcactgggt ccgccaggct     120
ccaggcaagg ggctggagtg gatggcagtt atatcatttg atggaggtaa taaaaataat     180
gcagactccg tgaagggccg gttcaccatc tccagagaca attccaagaa cacgctgtat     240
ctgcaaatga acagcctgag agctgaggac acggctgtgt attattgtgc gaaagagggc     300
gatagaagtg gtcacccctta cttctactat tacggttttgg acgtctgggg ccaagggacc     360
acggtcaccg tctcctca                                                    378

<210> SEQ ID NO 74
<211> LENGTH: 126
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Val Ile Ser Phe Asp Gly Gly Asn Lys Asn Asn Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Gly Asp Arg Ser Gly His Pro Tyr Phe Tyr Tyr Tyr Gly
            100                 105                 110

Leu Asp Val Trp Gly Gln Gly Thr Thr Val Thr Val Ser Ser
        115                 120                 125

<210> SEQ ID NO 75
<211> LENGTH: 24
<212> TYPE: DNA
<213> ORGANISM: Artificial Sequence
<220> FEATURE:
<223> OTHER INFORMATION: Synthetic

<400> SEQUENCE: 75
ggattcacct tcagtagtta tggc                                          24

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Gly Phe Thr Phe Ser Ser Tyr Gly
 1               5

<210> SEQ ID NO 77
<211> LENGTH: 24
<212> TYPE: DNA
<213> ORGANISM: Artificial Sequence
<220> FEATURE:
<223> OTHER INFORMATION: Synthetic

<400> SEQUENCE: 77
atatcatttg atggaggtaa taaa                                          24

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Ile Ser Phe Asp Gly Gly Asn Lys
 1               5

<210> SEQ ID NO 79
<211> LENGTH: 57
<212> TYPE: DNA
<213> ORGANISM: Artificial Sequence
<220> FEATURE:
<223> OTHER INFORMATION: Synthetic

<400> SEQUENCE: 79
gcgaaagagg gcgatagaag tggtcaccct tacttctact attacggttt ggacgtc      57

<210> SEQ ID NO 80
<211> LENGTH: 19
<212> TYPE: PRT
<213> ORGANISM: Artificial Sequence
<220> FEATURE:
<223> OTHER INFORMATION: Synthetic

<400> SEQUENCE: 80

Ala Lys Glu Gly Asp Arg Ser Gly His Pro Tyr Phe Tyr Tyr Tyr Gly
 1               5                  10                  15

Leu Asp Val

<210> SEQ ID NO 81
<211> LENGTH: 321

<212> TYPE: DNA
<213> ORGANISM: Artificial Sequence
<220> FEATURE:
<223> OTHER INFORMATION: Synthetic

<400> SEQUENCE: 81

```
gccatccaga tgacccagtc tccatccttc ctgtctgcat ctgtaggaga cagagtcacc    60
atcacttgct gggccagtca gggcattagc agttatttag cctggtatca gcagaaacca   120
gggaaagccc ctaagctcct gatctatgct gcatccactt tgcaaagtgg ggtcccatca   180
aggttcagcg gcagtggatc tgagacagaa ttcactctca caatcagcag cctgcagcct   240
gaagattttg caacttatta ctgtcaacag cttcatagtt accctctcac tttcggcgga   300
gggaccaagg tggaaatcaa a                                             321
```

<210> SEQ ID NO 82
<211> LENGTH: 107
<212> TYPE: PRT
<213> ORGANISM: Artificial Sequence
<220> FEATURE:
<223> OTHER INFORMATION: Synthetic

<400> SEQUENCE: 82

```
Ala Ile Gln Met Thr Gln Ser Pro Ser Phe Leu Ser Ala Ser Val Gly
  1               5                  10                  15

Asp Arg Val Thr Ile Thr Cys Trp Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Glu Thr Glu Phe Thr Leu Thr Ile Ser Ser Leu Gln Pro
 65                  70                  75                  80

Glu Asp Phe Ala Thr Tyr Tyr Cys Gln Gln Leu His Ser Tyr Pro Leu
                 85                  90                  95

Thr Phe Gly Gly Gly Thr Lys Val Glu Ile Lys
            100                 105
```

<210> SEQ ID NO 83
<211> LENGTH: 18
<212> TYPE: DNA
<213> ORGANISM: Artificial Sequence
<220> FEATURE:
<223> OTHER INFORMATION: Synthetic

<400> SEQUENCE: 83

```
cagggcatta gcagttat                                                  18
```

<210> SEQ ID NO 84
<211> LENGTH: 6
<212> TYPE: PRT
<213> ORGANISM: Artificial Sequence
<220> FEATURE:
<223> OTHER INFORMATION: Synthetic

<400> SEQUENCE: 84

```
Gln Gly Ile Ser Ser Tyr
  1               5
```

<210> SEQ ID NO 85
<211> LENGTH: 9
<212> TYPE: DNA
<213> ORGANISM: Artificial Sequence

```
<220> FEATURE:
<223> OTHER INFORMATION: Synthetic

<400> SEQUENCE: 85 gctgcatcc                                                                  9

<210> SEQ ID NO 86
<211> LENGTH: 3
<212> TYPE: PRT
<213> ORGANISM: Artificial Sequence
<220> FEATURE:
<223> OTHER INFORMATION: Synthetic

<400> SEQUENCE: 86

Ala Ala Ser
 1

<210> SEQ ID NO 87
<211> LENGTH: 27
<212> TYPE: DNA
<213> ORGANISM: Artificial Sequence
<220> FEATURE:
<223> OTHER INFORMATION: Synthetic

<400> SEQUENCE: 87
caacagcttc atagttaccc tctcact                                              27

<210> SEQ ID NO 88
<211> LENGTH: 9
<212> TYPE: PRT
<213> ORGANISM: Artificial Sequence
<220> FEATURE:
<223> OTHER INFORMATION: Synthetic

<400> SEQUENCE: 88

Gln Gln Leu His Ser Tyr Pro Leu Thr
 1               5

<210> SEQ ID NO 89
<211> LENGTH: 375
<212> TYPE: DNA
<213> ORGANISM: Artificial Sequence
<220> FEATURE:
<223> OTHER INFORMATION: Synthetic

<400> SEQUENCE: 89
caggtgcagc tggtggagtc tgggggaggc gtggtccagc ctgggaggtc cctgagactc          60
tcctgtgcag cctctggatt caccttcagt agttatggca tgcactgggt ccgccaggct         120
ccaggcaagg ggctggagtg gatggcagtt atatcatttg atggaggtaa taaaaataat         180
gcagactccg tgaagggccg gttcaccatc tccagagaca attccaagaa cacgctgtat         240
ctgcaaatga acagcctgag agctgaggac acggctgtgt attattgtgc gaaagagggc         300
gatagaagtg gtcacccta cttctactat tacggtttgg acgtctgggg ccaagggacc         360
acggtcaccg tctcc                                                         375

<210> SEQ ID NO 90
<211> LENGTH: 125
<212> TYPE: PRT
<213> ORGANISM: Artificial Sequence
<220> FEATURE:
<223> OTHER INFORMATION: Synthetic

<400> SEQUENCE: 90

Gln Val Gln Leu Val Glu Ser Gly Gly Gly Val Val Gln Pro Gly Arg
```

```
                1               5                  10                 15
Ser Leu Arg Leu Ser Cys Ala Ala Ser Gly Phe Thr Phe Ser Ser Tyr
            20                  25                 30

Gly Met His Trp Val Arg Gln Ala Pro Gly Lys Gly Leu Glu Trp Met
            35                  40                 45

Ala Val Ile Ser Phe Asp Gly Gly Asn Lys Asn Asn Ala Asp Ser Val
        50                  55                 60

Lys Gly Arg Phe Thr Ile Ser Arg Asp Asn Ser Lys Asn Thr Leu Tyr
65                  70                  75                     80

Leu Gln Met Asn Ser Leu Arg Ala Glu Asp Thr Ala Val Tyr Tyr Cys
                85                  90                 95

Ala Lys Glu Gly Asp Arg Ser Gly His Pro Tyr Phe Tyr Tyr Tyr Gly
            100                 105                110

Leu Asp Val Trp Gly Gln Gly Thr Thr Val Thr Val Ser
            115                 120             125

<210> SEQ ID NO 91
<211> LENGTH: 321
<212> TYPE: DNA
<213> ORGANISM: Artificial Sequence
<220> FEATURE:
<223> OTHER INFORMATION: Synthetic

<400> SEQUENCE: 91
gacatccagt tgacccagtc tccatccttc ctgtctgcat ctgtaggaga cagagtcacc    60
atcacttgct gggccagtca gggcattagc agttatttag cctggtatca gcagaaacca   120
gggaaagccc ctaagctcct gatctatgct gcatccactt tgcaaagtgg ggtcccatca   180
aggttcagcg gcagtggatc tgagacagaa ttcactctca caatcagcag cctgcagcct   240
gaagattttg caacttatta ctgtcaacag cttcatagtt accctctcac tttcggcgga   300
gggaccaagg tggaaatcaa a                                             321

<210> SEQ ID NO 92
<211> LENGTH: 107
<212> TYPE: PRT
<213> ORGANISM: Artificial Sequence
<220> FEATURE:
<223> OTHER INFORMATION: Synthetic

<400> SEQUENCE: 92

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Glu Thr Glu Phe Thr Leu Thr Ile Ser Ser Leu Gln Pro
65                  70                  75                  80

Glu Asp Phe Ala Thr Tyr Tyr Cys Gln Gln Leu His Ser Tyr Pro Leu
                85                  90                  95

Thr Phe Gly Gly Gly Thr Lys Val Glu Ile Lys
            100                 105

<210> SEQ ID NO 93
<211> LENGTH: 376
<212> TYPE: DNA
```

<210> SEQ ID NO 93
<211> LENGTH: 376
<212> TYPE: DNA
<213> ORGANISM: Artificial Sequence
<220> FEATURE:
<223> OTHER INFORMATION: Synthetic

<400> SEQUENCE: 93

```
caggtgcagc tggtggagtc tgggggaggc gtggtccagc ctggagggtc cctgagactc      60
tcctgtgcag cctctggatt caccttcagt agttatggca tgcactgggt ccgccaggct     120
ccaggcaagg gctggagtg gtggcagtt atatcatttg atggaggtaa taaatactat       180
gcagactccg tgaagggccg attcaccatc tccagagaca attccaagaa cacgctgtat     240
ctgcaaatga acagcctgag agctgaggac acggctgtgt attactgtgc gaaagagggc     300
gatagaagtg gtcacccta cttctactat tacggtttgg acgtctgggg ccaagggacc     360
acggtcaccg tctcct                                                    376
```

<210> SEQ ID NO 94
<211> LENGTH: 125
<212> TYPE: PRT
<213> ORGANISM: Artificial Sequence
<220> FEATURE:
<223> OTHER INFORMATION: Synthetic

<400> SEQUENCE: 94

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Phe Asp Gly Gly Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Glu Gly Asp Arg Ser Gly His Pro Tyr Phe Tyr Tyr Tyr Gly
            100                 105                 110
Leu Asp Val Trp Gly Gln Gly Thr Thr Val Thr Val Ser
        115                 120                 125

<210> SEQ ID NO 95
<211> LENGTH: 321
<212> TYPE: DNA
<213> ORGANISM: Artificial Sequence
<220> FEATURE:
<223> OTHER INFORMATION: Synthetic

<400> SEQUENCE: 95

```
gacatccagt tgacccagtc tccatccttc ctgtctgcat ctgtaggaga cagagtcacc      60
atcacttgca gagccagtca gggcattagc agttatttag cctggtatca gcagaaacca    120
gggaaagccc ctaagctcct gatctatgct gcatccactt tgcaaagtgg ggtcccatca    180
aggttcagcg gcagtggatc tggcacagaa ttcactctca caatcagcag cctgcagcct    240
gaagattttg caacttatta ctgtcaacag cttcatagtt accctctcac tttcggcgga    300
gggaccaagg tggagatcaa a                                              321
```

<210> SEQ ID NO 96
<211> LENGTH: 107
<212> TYPE: PRT

<213> ORGANISM: Artificial Sequence
<220> FEATURE:
<223> OTHER INFORMATION: Synthetic

<400> SEQUENCE: 96

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu His Ser Tyr Pro Leu
                85                  90                  95

Thr Phe Gly Gly Gly Thr Lys Val Glu Ile Lys
            100                 105

<210> SEQ ID NO 97
<211> LENGTH: 366
<212> TYPE: DNA
<213> ORGANISM: Artificial Sequence
<220> FEATURE:
<223> OTHER INFORMATION: Synthetic

<400> SEQUENCE: 97
gaggtgcagc tggtgcagtc tgggggaggc ttagtacagc cggggggggtc cctgcgactc      60
tcctgtgcag cctctggatt caccttcagt cggtacgaca tgcactgggt ccgccaagtg     120
acaggaaaag gtctggaatg ggtatcaggc attggtacag caggtgacac atactatcca     180
ggctccgtga agggccgatt caccatctcc agagaaaatg acaagaactc cctgtatctt     240
caaatgaaca gcctgagagt cggggacacg gctgtttatt actgtgcaag aggagatagt     300
aagaactact acgttgggga ctactttgac tactggggcc agggaaccac ggtcaccgtc     360
tcctca                                                                366

<210> SEQ ID NO 98
<211> LENGTH: 122
<212> TYPE: PRT
<213> ORGANISM: Artificial Sequence
<220> FEATURE:
<223> OTHER INFORMATION: Synthetic

<400> SEQUENCE: 98

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Val Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Asp Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Asp Ser Lys Asn Tyr Tyr Val Gly Asp Tyr Phe Asp Tyr Trp

Gly Gln Gly Thr Thr Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct tcagtcggta cgac                                          24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Arg Tyr Asp
 1               5

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
attggtacag caggtgacac a                                             21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Gly Thr Ala Gly Asp Thr
 1               5

<210> SEQ ID NO 103
<211> LENGTH: 48
<212> TYPE: DNA
<213> ORGANISM: Artificial Sequence
<220> FEATURE:
<223> OTHER INFORMATION: Synthetic

<400> SEQUENCE: 103
gcaagaggag atagtaagaa ctactacgtt ggggactact ttgactac                48

<210> SEQ ID NO 104
<211> LENGTH: 16
<212> TYPE: PRT
<213> ORGANISM: Artificial Sequence
<220> FEATURE:
<223> OTHER INFORMATION: Synthetic

<400> SEQUENCE: 104

Ala Arg Gly Asp Ser Lys Asn Tyr Tyr Val Gly Asp Tyr Phe Asp Tyr
 1               5                  10                  15

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105

```
gacatccaga tgacccagtc tccttccacc ctgtctgcat ctgtaggaga cagagtcacc      60
ttcacttgcc gggccagtca cagtattggt aattggttgg cctggtatca gcagaaacca     120
gggaaagccc ctaaggtcct gatctatgag cgtctagtt tagaagatgg ggtcccatca      180
aggttcagcg gcagtggatc tgggacagaa ttcactctca ccatcagcag cctgcagcct    240
gatgattttg caacttatta ctgccaacaa tatgatactt attttcggac gttcggccaa    300
gggaccaagg tggagatcaa a                                              321
```

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

```
Asp Ile Gln Met Thr Gln Ser Pro Ser Thr Leu Ser Ala Ser Val Gly
 1               5                  10                  15

Asp Arg Val Thr Phe Thr Cys Arg Ala Ser His Ser Ile Gly Asn Trp
            20                  25                  30

Leu Ala Trp Tyr Gln Gln Lys Pro Gly Lys Ala Pro Lys Val Leu Ile
        35                  40                  45

Tyr Glu Ala Ser Ser Leu Glu Asp Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Phe Arg
                85                  90                  95

Thr Phe Gly Gln Gly Thr Lys Val Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107

```
cacagtattg gtaattgg                                                   18
```

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

```
His Ser Ile Gly Asn Trp
 1               5
```

<210> SEQ ID NO 109

```
<211> LENGTH: 9
<212> TYPE: DNA
<213> ORGANISM: Artificial Sequence
<220> FEATURE:
<223> OTHER INFORMATION: Synthetic

<400> SEQUENCE: 109 gaggcgtct                                                                       9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Glu Ala Ser
 1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacaatatg atacttattt tcggacg                                                  27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Tyr Asp Thr Tyr Phe Arg Thr
 1               5

<210> SEQ ID NO 113
<211> LENGTH: 366
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttagtacagc cggggggtc cctgcgactc              60 tcctgtgcag cctctggatt caccttcagt cggtacgaca tgcactgggt ccgccaagtg           120
acaggaaaag gtctggaatg ggtatcaggc attggtacag caggtgacac atactatcca           180
ggctccgtga aggccgatt caccatctcc agagaaaatg caagaactc cctgtatctt             240 caaatgaaca gcctgagagt cggggacacg gctgtttatt actgtgcaag aggagatagt           300
aagaactact acgttgggga ctactttgac tactggggcc agggaaccct ggtcaccgtc           360
tcctca                                                                      366

<210> SEQ ID NO 114
<211> LENGTH: 122
<212> TYPE: PRT
<213> ORGANISM: Artificial Sequence
<220> FEATURE:
<223> OTHER INFORMATION: Synthetic
```

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asp Met His Trp Val Arg Gln Val Thr Gly Lys Gly Leu Glu Trp Val
        35                  40                  45

Ser Gly Ile Gly Thr Ala Gly Asp Thr Tyr Tyr Pro Gly Ser Val Lys
50                  55                  60

Gly Arg Phe Thr Ile Ser Arg Glu Asn Asp Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Asp Ser Lys Asn Tyr Tyr Val Gly Asp Tyr Phe Asp Tyr Trp
            100                 105                 110

Gly Gln Gly Thr Leu Val Thr Val Ser Ser
        115                 120

<210> SEQ ID NO 115
<211> LENGTH: 321
<212> TYPE: DNA
<213> ORGANISM: Artificial Sequence
<220> FEATURE:
<223> OTHER INFORMATION: Synthetic

<400> SEQUENCE: 115
gacatccaga tgacccagtc tccttccacc ctgtctgcat ctgtaggaga cagagtcacc    60
ttcacttgcc gggccagtca cagtattggt aattggttgg cctggtatca gcagaaacca   120
gggaaagccc ctaaggtcct gatctatgag gcgtctagtt tagaagatgg ggtcccatca   180
aggttcagcg gcagtggatc tgggacagaa ttcactctca ccatcagcag cctgcagcct   240
gatgattttg caacttatta ctgccaacaa tatgatactt attttcggac gttcggccaa   300
gggaccaagg tggaaatcaa a                                             321

<210> SEQ ID NO 116
<211> LENGTH: 107
<212> TYPE: PRT
<213> ORGANISM: Artificial Sequence
<220> FEATURE:
<223> OTHER INFORMATION: Synthetic

<400> SEQUENCE: 116

Asp Ile Gln Met Thr Gln Ser Pro Ser Thr Leu Ser Ala Ser Val Gly
1               5                   10                  15

Asp Arg Val Thr Phe Thr Cys Arg Ala Ser His Ser Ile Gly Asn Trp
            20                  25                  30

Leu Ala Trp Tyr Gln Gln Lys Pro Gly Lys Ala Pro Lys Val Leu Ile
        35                  40                  45

Tyr Glu Ala Ser Ser Leu Glu Asp Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Tyr Phe Arg
                85                  90                  95

Thr Phe Gly Gln Gly Thr Lys Val Glu Ile Lys
            100                 105

<210> SEQ ID NO 117
<211> LENGTH: 366
<212> TYPE: DNA
<213> ORGANISM: Artificial Sequence
<220> FEATURE:
<223> OTHER INFORMATION: Synthetic

<400> SEQUENCE: 117

```
gaggtgcagc tggtggagtc tgggggaggc ttggtacagc ctgggggtc cctgagactc      60
tcctgtgcag cctctggatt caccttcagt cggtacgaca tgcactgggt ccgccaagct    120
acaggaaaag gtctgagtg gtctcagct attggtacag caggtgacac atactatcca     180
ggctccgtga agggccgatt caccatctcc agagaaaatg ccaagaactc cttgtatctt    240
caaatgaaca gcctgagagc cggggacacg gctgtgtatt actgtgcaag aggagatagt    300
aagaactact acgttgggga ctactttgac tactggggcc agggaaccct ggtcaccgtc    360
tcctca                                                                366
```

<210> SEQ ID NO 118
<211> LENGTH: 122
<212> TYPE: PRT
<213> ORGANISM: Artificial Sequence
<220> FEATURE:
<223> OTHER INFORMATION: Synthetic

<400> SEQUENCE: 118

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Asp Met His Trp Val Arg Gln Ala Thr Gly Lys Gly Leu Glu Trp Val
         35                  40                  45

Ser Ala Ile Gly Thr Ala Gly Asp Thr Tyr Tyr Pro Gly Ser Val Lys
     50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                 85                  90                  95

Arg Gly Asp Ser Lys Asn Tyr Tyr Val Gly Asp Tyr Phe Asp Tyr Trp
            100                 105                 110

Gly Gln Gly Thr Leu Val Thr Val Ser Ser
        115                 120
```

<210> SEQ ID NO 119
<211> LENGTH: 322
<212> TYPE: DNA
<213> ORGANISM: Artificial Sequence
<220> FEATURE:
<223> OTHER INFORMATION: Synthetic

<400> SEQUENCE: 119

```
gacatccaga tgacccagtc tccttccacc ctgtctgcat ctgtaggaga cagagtcacc      60
atcacttgcc gggccagtca cagtattggt aattggttgg cctggtatca gcagaaacca    120
gggaaagccc ctaagctcct gatctatgag gcgtctagtt tagaaagtgg ggtcccatca    180
aggttcagcg gcagtggatc tgggacagaa ttcactctca ccatcagcag cctgcagcct    240
gatgattttg caacttatta ctgccaacaa tatgatactt attttcggac gttcggccaa    300
gggaccaagg tggaaatcaa ac                                              322
```

<210> SEQ ID NO 120
<211> LENGTH: 107
<212> TYPE: PRT
<213> ORGANISM: Artificial Sequence
<220> FEATURE:
<223> OTHER INFORMATION: Synthetic

<400> SEQUENCE: 120

```
Asp Ile Gln Met Thr Gln Ser Pro Ser Thr Leu Ser Ala Ser Val Gly
 1               5                   10                  15

Asp Arg Val Thr Ile Thr Cys Arg Ala Ser His Ser Ile Gly Asn Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Tyr Phe Arg
                85                  90                  95

Thr Phe Gly Gln Gly Thr Lys Val Glu Ile Lys
            100                 105
```

<210> SEQ ID NO 121
<211> LENGTH: 366
<212> TYPE: DNA
<213> ORGANISM: Artificial Sequence
<220> FEATURE:
<223> OTHER INFORMATION: Synthetic

<400> SEQUENCE: 121

```
caggtgcagc tggtggagtc cggggggaggc ttggtccagc ctgggggtc cctgagactc    60
tcctgtgcag cctctggatt caccttcagt acctacgaca tgcactggt ccgccaaggt   120
ctaggaaaag gtctggagtg gtctcagct attggttctg ctggtgacac atactatcca   180
ggctccgtga agggccgctt caccatctcc agagacaatg ccaagagctc cttgtttctt   240
cacatgaaca gcctgagagc cggggacacg gctctatatt actgtgcaag aggagatagt   300
cggaactact cgttgggga ctactttgac tactggggcc agggaaccac ggtcaccgtc   360
tcctca                                                              366
```

<210> SEQ ID NO 122
<211> LENGTH: 122
<212> TYPE: PRT
<213> ORGANISM: Artificial Sequence
<220> FEATURE:
<223> OTHER INFORMATION: Synthetic

<400> SEQUENCE: 122

```
Gln Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Thr Tyr
            20                  25                  30

Asp Met His Trp Val Arg Gln Gly Leu Gly Lys Gly Leu Glu Trp Val
        35                  40                  45

Ser Ala Ile Gly Ser Ala Gly Asp Thr Tyr Tyr Pro Gly Ser Val Lys
 50                  55                  60

Gly Arg Phe Thr Ile Ser Arg Asp Asn Ala Lys Ser Ser Leu Phe Leu
 65                  70                  75                  80

His Met Asn Ser Leu Arg Ala Gly Asp Thr Ala Leu Tyr Tyr Cys Ala
```

85                  90                  95
Arg Gly Asp Ser Arg Asn Tyr Phe Val Gly Asp Tyr Phe Asp Tyr Trp
                100                 105                 110

Gly Gln Gly Thr Thr Val Thr Val Ser Ser
        115                 120

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ggattcacct tcagtaccta cgac                                              24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Phe Thr Phe Ser Thr Tyr Asp
1               5

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
attggttctg ctggtgacac a                                                 21

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Ile Gly Ser Ala Gly Asp Thr
1               5

<210> SEQ ID NO 127
<211> LENGTH: 48
<212> TYPE: DNA
<213> ORGANISM: Artificial Sequence
<220> FEATURE:
<223> OTHER INFORMATION: Synthetic

<400> SEQUENCE: 127
gcaagaggag atagtcggaa ctacttcgtt ggggactact ttgactac                    48

<210> SEQ ID NO 128
<211> LENGTH: 16
<212> TYPE: PRT
<213> ORGANISM: Artificial Sequence
<220> FEATURE:
<223> OTHER INFORMATION: Synthetic

<400> SEQUENCE: 128

Ala Arg Gly Asp Ser Arg Asn Tyr Phe Val Gly Asp Tyr Phe Asp Tyr
1               5                   10                  15

<210> SEQ ID NO 129
<211> LENGTH: 321
<212> TYPE: DNA
<213> ORGANISM: Artificial Sequence
<220> FEATURE:
<223> OTHER INFORMATION: Synthetic

<400> SEQUENCE: 129
gccatccaga tgacccagtc tccgtccacc ctgtctgcat ctataggaga cagagtcacc        60
atcacttgcc gggccagtca gagtattagt agttggttgg cctggtatca gcagaaacca      120
gggaaagccc ctaaggtcct gatctataag gcgtctagtt tagaagctgg ggtcccatca      180
aggttcagcg gcagtggatc tgggacagaa ttcactctca ccatcagcag cctacagcct      240
gatgattttg caagttatta ctgccaacag tatagtagtt attctcggac gttcggccaa      300
gggaccaagg tggagatcaa a                                                321

<210> SEQ ID NO 130
<211> LENGTH: 107
<212> TYPE: PRT
<213> ORGANISM: Artificial Sequence
<220> FEATURE:
<223> OTHER INFORMATION: Synthetic

<400> SEQUENCE: 130

Ala Ile Gln Met Thr Gln Ser Pro Ser Thr Leu Ser Ala Ser Ile Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Val Leu Ile
            35                  40                  45

Tyr Lys Ala Ser Ser Leu Glu Ala Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Ser Ser Tyr Ser Arg
                85                  90                  95

Thr Phe Gly Gln Gly Thr Lys Val Glu Ile Lys
            100                 105

<210> SEQ ID NO 131
<211> LENGTH: 18
<212> TYPE: DNA
<213> ORGANISM: Artificial Sequence
<220> FEATURE:
<223> OTHER INFORMATION: Synthetic

<400> SEQUENCE: 131
cagagtatta gtagttgg                                                     18

<210> SEQ ID NO 132
<211> LENGTH: 6
<212> TYPE: PRT
<213> ORGANISM: Artificial Sequence
<220> FEATURE:
<223> OTHER INFORMATION: Synthetic

<400> SEQUENCE: 132

Gln Ser Ile Ser Ser Trp
1               5

<210> SEQ ID NO 133
<211> LENGTH: 9
<212> TYPE: DNA
<213> ORGANISM: Artificial Sequence
<220> FEATURE:
<223> OTHER INFORMATION: Synthetic

<400> SEQUENCE: 133 aaggcgtct                                                                  9

<210> SEQ ID NO 134
<211> LENGTH: 3
<212> TYPE: PRT
<213> ORGANISM: Artificial Sequence
<220> FEATURE:
<223> OTHER INFORMATION: Synthetic

<400> SEQUENCE: 134

Lys Ala Ser
 1

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
caacagtata gtagttattc tcggacg                                             27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Gln Gln Tyr Ser Ser Tyr Ser Arg Thr
 1               5

<210> SEQ ID NO 137
<211> LENGTH: 366
<212> TYPE: DNA
<213> ORGANISM: Artificial Sequence
<220> FEATURE:
<223> OTHER INFORMATION: Synthetic

<400> SEQUENCE: 137
gaggtgcagc tggtggagtc tgggggaggc ttggtccagc ctggggggtc cctgagactc      60
tcctgtgcag cctctggatt caccttcagt acctacgaca tgcactgggt ccgccaaggt     120
ctaggaaaag gtctggagtg gtctcagct attggttctg ctggtgacac atactatcca     180
ggctccgtga agggccgctt caccatctcc agagacaatg ccaagagctc cttgtttctt     240
cacatgaaca gcctgagagc cggggacacg gctctatatt actgtgcaag aggagatagt     300
cggaactact cgttgggga ctactttgac tactggggcc agggaaccct ggtcaccgtc     360
tcctca                                                                   366

<210> SEQ ID NO 138
<211> LENGTH: 122
<212> TYPE: PRT
<213> ORGANISM: Artificial Sequence
<220> FEATURE:
<223> OTHER INFORMATION: Synthetic

<400> SEQUENCE: 138

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Asp Met His Trp Val Arg Gln Gly Leu Gly Lys Gly Leu Glu Trp Val
        35                  40                  45

Ser Ala Ile Gly Ser Ala Gly Asp Thr Tyr Tyr Pro Gly Ser Val Lys
    50                  55                  60

Gly Arg Phe Thr Ile Ser Arg Asp Asn Ala Lys Ser Ser Leu Phe Leu
65                  70                  75                  80

His Met Asn Ser Leu Arg Ala Gly Asp Thr Ala Leu Tyr Tyr Cys Ala
                85                  90                  95

Arg Gly Asp Ser Arg Asn Tyr Phe Val Gly Asp Tyr Phe Asp Tyr Trp
            100                 105                 110

Gly Gln Gly Thr Leu Val Thr Val Ser Ser
        115                 120

<210> SEQ ID NO 139
<211> LENGTH: 321
<212> TYPE: DNA
<213> ORGANISM: Artificial Sequence
<220> FEATURE:
<223> OTHER INFORMATION: Synthetic

<400> SEQUENCE: 139
gacatccaga tgacccagtc tccgtccacc ctgtctgcat ctataggaga cagagtcacc      60
atcacttgcc gggccagtca gagtattagt agttggttgg cctggtatca gcagaaacca    120
gggaaagccc ctaaggtcct gatctataag gcgtctagtt tagaagctgg ggtcccatca    180
aggttcagcg gcagtggatc tgggacagaa ttcactctca ccatcagcag cctacagcct    240
gatgattttg caagttatta ctgccaacag tatagtagtt attctcggac gttcggccaa    300
gggaccaagg tggaaatcaa a                                              321

<210> SEQ ID NO 140
<211> LENGTH: 107
<212> TYPE: PRT
<213> ORGANISM: Artificial Sequence
<220> FEATURE:
<223> OTHER INFORMATION: Synthetic

<400> SEQUENCE: 140

Asp Ile Gln Met Thr Gln Ser Pro Ser Thr Leu Ser Ala Ser Ile Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Glu Ala Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Ser Ser Tyr Ser Arg
                85                  90                  95

Thr Phe Gly Gln Gly Thr Lys Val Glu Ile Lys

<210> SEQ ID NO 141
<211> LENGTH: 366
<212> TYPE: DNA
<213> ORGANISM: Artificial Sequence
<220> FEATURE:
<223> OTHER INFORMATION: Synthetic

<400> SEQUENCE: 141

```
gaggtgcagc tggtggagtc tgggggaggc ttggtacagc ctggggggtc cctgagactc    60
tcctgtgcag cctctggatt caccttcagt acctacgaca tgcactgggt ccgccaagct   120
acaggaaaag gtctggagtg gtctcagct attggttctg ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag aggagatagt   300
cggaactact cgttgggga ctactttgac tactggggcc agggaaccct ggtcaccgtc   360
tcctca                                                              366
```

<210> SEQ ID NO 142
<211> LENGTH: 122
<212> TYPE: PRT
<213> ORGANISM: Artificial Sequence
<220> FEATURE:
<223> OTHER INFORMATION: Synthetic

<400> SEQUENCE: 142

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Thr Tyr
            20                  25                  30
Asp Met His Trp Val Arg Gln Ala Thr Gly Lys Gly Leu Glu Trp Val
        35                  40                  45
Ser Ala Ile Gly Ser Ala Gly Asp Thr Tyr Tyr Pro Gly Ser Val Lys
    50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Ala
                85                  90                  95
Arg Gly Asp Ser Arg Asn Tyr Phe Val Gly Asp Tyr Phe Asp Tyr Trp
            100                 105                 110
Gly Gln Gly Thr Leu Val Thr Val Ser Ser
        115                 120
```

<210> SEQ ID NO 143
<211> LENGTH: 322
<212> TYPE: DNA
<213> ORGANISM: Artificial Sequence
<220> FEATURE:
<223> OTHER INFORMATION: Synthetic

<400> SEQUENCE: 143

```
gacatccaga tgacccagtc tccttccacc ctgtctgcat ctgtaggaga cagagtcacc    60
atcacttgcc gggccagtca gagtattagt agttggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatagtagtt attctcggac gttcggccaa   300
```
gggaccaagg tggaaatcaa ac    322

<210> SEQ ID NO 144
<211> LENGTH: 107
<212> TYPE: PRT
<213> ORGANISM: Artificial Sequence
<220> FEATURE:
<223> OTHER INFORMATION: Synthetic

<400> SEQUENCE: 144

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Tyr Ser Arg
                85                  90                  95

Thr Phe Gly Gln Gly Thr Lys Val Glu Ile Lys
            100                 105

<210> SEQ ID NO 145
<211> LENGTH: 366
<212> TYPE: DNA
<213> ORGANISM: Artificial Sequence
<220> FEATURE:
<223> OTHER INFORMATION: Synthetic

<400> SEQUENCE: 145
caggtgcagc tggtggagtc tgggggaggc ttggtacagc ctggggggtc cctgagactc    60
tcctgtgtag cctctggatt caccttcagt agttacgaca tgcactgggt ccgccaactt    120
ccaggaaaag gtctggagtg gtctcagcc attggtgttg ctggtgacac atactatcca    180
gcctccgtga agggccgatt caccatctct agagaaaatg ccaagaactc cttgtatctt    240
caaatgaaca gcctgagagc cggggacacg gctgtgtatt actgtgcaag aggagacagt    300
gggaactact acgatgggga ctactttgac ttctggggcc agggaaccac ggtcaccgtc    360
tcctca    366

<210> SEQ ID NO 146
<211> LENGTH: 122
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Asp Met His Trp Val Arg Gln Leu Pro Gly Lys Gly Leu Glu Trp Val
        35                  40                  45

Ser Ala Ile Gly Val Ala Gly Asp Thr Tyr Tyr Pro Ala Ser Val Lys
    50                  55                  60

Gly Arg Phe Thr Ile Ser Arg Glu Asn Ala Lys Asn Ser Leu Tyr Leu

-continued

```
                65                  70                  75                  80
Gln Met Asn Ser Leu Arg Ala Gly Asp Thr Ala Val Tyr Tyr Cys Ala
                    85                  90                  95

Arg Gly Asp Ser Gly Asn Tyr Tyr Asp Gly Asp Tyr Phe Asp Phe Trp
                100                 105                 110

Gly Gln Gly Thr Thr Val Thr Val Ser Ser
        115                 120
```

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcacct tcagtagtta cgac                                    24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

```
Gly Phe Thr Phe Ser Ser Tyr Asp
  1               5
```

<210> SEQ ID NO 149
<211> LENGTH: 21
<212> TYPE: DNA
<213> ORGANISM: Artificial Sequence
<220> FEATURE:
<223> OTHER INFORMATION: Synthetic

<400> SEQUENCE: 149
attggtgttg ctggtgacac a                                       21

<210> SEQ ID NO 150
<211> LENGTH: 7
<212> TYPE: PRT
<213> ORGANISM: Artificial Sequence
<220> FEATURE:
<223> OTHER INFORMATION: Synthetic

<400> SEQUENCE: 150

```
Ile Gly Val Ala Gly Asp Thr
  1               5
```

<210> SEQ ID NO 151
<211> LENGTH: 48
<212> TYPE: DNA
<213> ORGANISM: Artificial Sequence
<220> FEATURE:
<223> OTHER INFORMATION: Synthetic

<400> SEQUENCE: 151
gcaagaggag acagtgggaa ctactacgat ggggactact ttgacttc          48

<210> SEQ ID NO 152
<211> LENGTH: 16
<212> TYPE: PRT
<213> ORGANISM: Artificial Sequence
<220> FEATURE:
<223> OTHER INFORMATION: Synthetic

<400> SEQUENCE: 152

Ala Arg Gly Asp Ser Gly Asn Tyr Tyr Asp Gly Asp Tyr Phe Asp Phe
1               5                   10                  15

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccttccacc ctgtctgcat ctgtaggaga cagagtcacc    60
atcacttgcc gggccagtca gagtattaat aggtggttgg cctggtatca gcaaaaacca   120
gggaaagccc ctaaggtcct gatctataag gcgtctaatt tagaaagtgg ggtcccatca   180
aggttcagcg gcagtggatc tgggacagaa ttcactctca ccatcagcag cctgcagcct   240
gatgattttg caacttatta ctgccaacag tatgatagtt attttcggac gttcggccaa   300
gggaccaagg tggagatcaa a                                             321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Arg Trp
            20                  25                  30

Leu Ala Trp Tyr Gln Gln Lys Pro Gly Lys Ala Pro Lys Val Leu Ile
        35                  40                  45

Tyr Lys Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Phe Arg
                85                  90                  95

Thr Phe Gly Gln Gly Thr Lys Val Glu Ile Lys
            100                 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
cagagtatta ataggtgg                                                  18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

```
Gln Ser Ile Asn Arg Trp
  1               5
```

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 aaggcgtct                                                              9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

```
Lys Ala Ser
  1
```

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacagtatg atagttattt tcggacg                                         27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

```
Gln Gln Tyr Asp Ser Tyr Phe Arg Thr
  1               5
```

<210> SEQ ID NO 161
<211> LENGTH: 366
<212> TYPE: DNA
<213> ORGANISM: Artificial Sequence
<220> FEATURE:
<223> OTHER INFORMATION: Synthetic

<400> SEQUENCE: 161
gaggtgcagc tggtggagtc tgggggaggc ttggtacagc ctggggggtc cctgagactc      60
tcctgtgtag cctctggatt caccttcagt agttacgaca tgcactgggt ccgccaactt     120
ccaggaaaag gtctggagtg gtctcagcc attggtgttg ctggtgacac atactatcca     180
gcctccgtga agggccgatt caccatctct agagaaaatg ccaagaactc cttgtatctt     240
caaatgaaca gcctgagagc cggggacacg gctgtgtatt actgtgcaag aggagacagt     300
gggaactact acgatgggga ctactttgac ttctggggcc agggaaccct ggtcaccgtc     360
tcctca                                                               366

<210> SEQ ID NO 162

<211> LENGTH: 122
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Asp Met His Trp Val Arg Gln Leu Pro Gly Lys Gly Leu Glu Trp Val
        35                  40                  45

Ser Ala Ile Gly Val Ala Gly Asp Thr Tyr Tyr Pro Ala Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Ser Gly Asn Tyr Tyr Asp Gly Asp Tyr Phe Asp Phe Trp
            100                 105                 110

Gly Gln Gly Thr Leu Val Thr Val Ser Ser
        115                 120

<210> SEQ ID NO 163
<211> LENGTH: 321
<212> TYPE: DNA
<213> ORGANISM: Artificial Sequence
<220> FEATURE:
<223> OTHER INFORMATION: Synthetic

<400> SEQUENCE: 163
gacatccaga tgacccagtc tccttccacc ctgtctgcat ctgtaggaga cagagtcacc      60
atcacttgcc gggccagtca gagtattaat aggtggttgg cctggtatca gcaaaaacca    120
gggaaagccc ctaaggtcct gatctataag gcgtctaatt tagaaagtgg ggtcccatca    180
aggttcagcg gcagtggatc tgggacagaa ttcactctca ccatcagcag cctgcagcct    240
gatgattttg caacttatta ctgccaacag tatgatagtt attttcggac gttcggccaa    300
gggaccaagg tggagatcaa a                                              321

<210> SEQ ID NO 164
<211> LENGTH: 107
<212> TYPE: PRT
<213> ORGANISM: Artificial Sequence
<220> FEATURE:
<223> OTHER INFORMATION: Synthetic

<400> SEQUENCE: 164

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Arg Trp
            20                  25                  30

Leu Ala Trp Tyr Gln Gln Lys Pro Gly Lys Ala Pro Lys Val Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Phe Arg

```
                    85                  90                  95
Thr Phe Gly Gln Gly Thr Lys Val Glu Ile Lys
            100                 105

<210> SEQ ID NO 165
<211> LENGTH: 366
<212> TYPE: DNA
<213> ORGANISM: Artificial Sequence
<220> FEATURE:
<223> OTHER INFORMATION: Synthetic

<400> SEQUENCE: 165
gaggtgcagc tggtggagtc tgggggaggc ttggtacagc ctggggggtc cctgagactc      60
tcctgtgcag cctctggatt caccttcagt agttacgaca tgcactgggt ccgccaagct     120
acaggaaaag gtctggagtg ggtctcagct attggtgttg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag aggagacagt     300
gggaactact acgatgggga ctactttgac ttctggggcc agggaaccct ggtcaccgtc     360
tcctca                                                                366

<210> SEQ ID NO 166
<211> LENGTH: 122
<212> TYPE: PRT
<213> ORGANISM: Artificial Sequence
<220> FEATURE:
<223> OTHER INFORMATION: Synthetic

<400> SEQUENCE: 166

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Val Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Ser Gly Asn Tyr Tyr Asp Gly Asp Tyr Phe Asp Phe Trp
            100                 105                 110

Gly Gln Gly Thr Leu Val Thr Val Ser Ser
        115                 120

<210> SEQ ID NO 167
<211> LENGTH: 322
<212> TYPE: DNA
<213> ORGANISM: Artificial Sequence
<220> FEATURE:
<223> OTHER INFORMATION: Synthetic

<400> SEQUENCE: 167
gacatccaga tgacccagtc tccttccacc ctgtctgcat ctgtaggaga cagagtcacc      60
atcacttgcc gggccagtca gagtattaat aggtggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
```

```
gatgattttg caacttatta ctgccaacag tatgatagtt attttcggac gttcggccaa    300
gggaccaagg tggaaatcaa ac                                             322
```

<210> SEQ ID NO 168
<211> LENGTH: 107
<212> TYPE: PRT
<213> ORGANISM: Artificial Sequence
<220> FEATURE:
<223> OTHER INFORMATION: Synthetic

<400> SEQUENCE: 168

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Asn Arg Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Phe Arg
                85                  90                  95

Thr Phe Gly Gln Gly Thr Lys Val Glu Ile Lys
            100                 105
```

<210> SEQ ID NO 169
<211> LENGTH: 366
<212> TYPE: DNA
<213> ORGANISM: Artificial Sequence
<220> FEATURE:
<223> OTHER INFORMATION: Synthetic

<400> SEQUENCE: 169

```
gaggtgcagc tggtggagtc tgggggaggc ttggtccagc ctgggggtc cctgagactc      60 tcctgtgcag cctctggatt caccttcagt acctacgaca tgcactgggt ccgccaagct    120
ccaggaaaag gtctggagtg ggtctcagct attggttctg ctggtgacac atactatcca    180
ggctccgtga agggccgatt caccatctcc agagacaatg ccaagagctc cttgtttctt    240
caaatgaaca gcctgagagc cggggacacg gctctatatt actgtgcaag aggagatagt    300
cggaactact tcgttgggga ctactttgac tactggggcc agggaaccac ggtcaccgtc    360
tcctca                                                              366
```

<210> SEQ ID NO 170
<211> LENGTH: 122
<212> TYPE: PRT
<213> ORGANISM: Artificial Sequence
<220> FEATURE:
<223> OTHER INFORMATION: Synthetic

<400> SEQUENCE: 170

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Asp Met His Trp Val Arg Gln Ala Pro Gly Lys Gly Leu Glu Trp Val
        35                  40                  45

Ser Ala Ile Gly Ser Ala Gly Asp Thr Tyr Tyr Pro Gly Ser Val Lys
```

```
                50                  55                  60
Gly Arg Phe Thr Ile Ser Arg Asp Asn Ala Lys Ser Ser Leu Phe Leu
 65                  70                  75                  80

Gln Met Asn Ser Leu Arg Ala Gly Asp Thr Ala Leu Tyr Tyr Cys Ala
                 85                  90                  95

Arg Gly Asp Ser Arg Asn Tyr Phe Val Gly Asp Tyr Phe Asp Tyr Trp
            100                 105                 110

Gly Gln Gly Thr Thr Val Thr Val Ser Ser
        115                 120
```

<210> SEQ ID NO 171
<211> LENGTH: 24
<212> TYPE: DNA
<213> ORGANISM: Artificial Sequence
<220> FEATURE:
<223> OTHER INFORMATION: Synthetic

<400> SEQUENCE: 171
ggattcacct tcagtaccta cgac                                          24

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

```
Gly Phe Thr Phe Ser Thr Tyr Asp
 1               5
```

<210> SEQ ID NO 173
<211> LENGTH: 21
<212> TYPE: DNA
<213> ORGANISM: Artificial Sequence
<220> FEATURE:
<223> OTHER INFORMATION: Synthetic

<400> SEQUENCE: 173
attggttctg ctggtgacac a                                             21

<210> SEQ ID NO 174
<211> LENGTH: 7
<212> TYPE: PRT
<213> ORGANISM: Artificial Sequence
<220> FEATURE:
<223> OTHER INFORMATION: Synthetic

<400> SEQUENCE: 174

```
Ile Gly Ser Ala Gly Asp Thr
 1               5
```

<210> SEQ ID NO 175
<211> LENGTH: 48
<212> TYPE: DNA
<213> ORGANISM: Artificial Sequence
<220> FEATURE:
<223> OTHER INFORMATION: Synthetic

<400> SEQUENCE: 175
gcaagaggag atagtcggaa ctacttcgtt ggggactact ttgactac                48

<210> SEQ ID NO 176
<211> LENGTH: 16
<212> TYPE: PRT

```
<213> ORGANISM: Artificial Sequence
<220> FEATURE:
<223> OTHER INFORMATION: Synthetic

<400> SEQUENCE: 176

Ala Arg Gly Asp Ser Arg Asn Tyr Phe Val Gly Asp Tyr Phe Asp Tyr
 1               5                  10                  15

<210> SEQ ID NO 177
<211> LENGTH: 321
<212> TYPE: DNA
<213> ORGANISM: Artificial Sequence
<220> FEATURE:
<223> OTHER INFORMATION: Synthetic

<400> SEQUENCE: 177
gacatccagt tgacccagtc tccttccacc ctgtctgcat ctgtaggaga cagagtcacc      60
atcacttgcc gggccagtca gagtattggt acctggttgg cctggtatca gcagaaacca    120
gggaaagccc ctaagatcct gatctataag gcgtctagtt tagaaggtgg ggtcccatca    180
aggttcagcg gcagtggatc tgggacagaa ttcactctca ccatcagcag cctgcagcct    240
gatgattttg caaattacta ctgccaacag tataatagtt tttatcggac gttcggccaa    300
gggaccaagg tggagatcaa a                                              321

<210> SEQ ID NO 178
<211> LENGTH: 107
<212> TYPE: PRT
<213> ORGANISM: Artificial Sequence
<220> FEATURE:
<223> OTHER INFORMATION: Synthetic

<400> SEQUENCE: 178

Asp Ile Gln Leu Thr Gln Ser Pro Ser Thr Leu Ser Ala Ser Val Gly
 1               5                  10                  15

Asp Arg Val Thr Ile Thr Cys Arg Ala Ser Gln Ser Ile Gly Thr Trp
             20                  25                  30

Leu Ala Trp Tyr Gln Gln Lys Pro Gly Lys Ala Pro Lys Ile Leu Ile
         35                  40                  45

Tyr Lys Ala Ser Ser Leu Glu Gly Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Asn Tyr Tyr Cys Gln Gln Tyr Asn Ser Phe Tyr Arg
                 85                  90                  95

Thr Phe Gly Gln Gly Thr Lys Val Glu Ile Lys
             100                 105

<210> SEQ ID NO 179
<211> LENGTH: 18
<212> TYPE: DNA
<213> ORGANISM: Artificial Sequence
<220> FEATURE:
<223> OTHER INFORMATION: Synthetic

<400> SEQUENCE: 179
cagagtattg gtacctgg                                                   18

<210> SEQ ID NO 180
<211> LENGTH: 6
<212> TYPE: PRT
<213> ORGANISM: Artificial Sequence
<220> FEATURE:
```

<223> OTHER INFORMATION: Synthetic

<400> SEQUENCE: 180

Gln Ser Ile Gly Thr Trp
1               5

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181 aaggcgtct                                                                 9

<210> SEQ ID NO 182
<211> LENGTH: 3
<212> TYPE: PRT
<213> ORGANISM: Artificial Sequence
<220> FEATURE:
<223> OTHER INFORMATION: Synthetic

<400> SEQUENCE: 182

Lys Ala Ser
1

<210> SEQ ID NO 183
<211> LENGTH: 27
<212> TYPE: DNA
<213> ORGANISM: Artificial Sequence
<220> FEATURE:
<223> OTHER INFORMATION: Synthetic

<400> SEQUENCE: 183
caacagtata atagttttta tcggacg                                            27

<210> SEQ ID NO 184
<211> LENGTH: 9
<212> TYPE: PRT
<213> ORGANISM: Artificial Sequence
<220> FEATURE:
<223> OTHER INFORMATION: Synthetic

<400> SEQUENCE: 184

Gln Gln Tyr Asn Ser Phe Tyr Arg Thr
1               5

<210> SEQ ID NO 185
<211> LENGTH: 366
<212> TYPE: DNA
<213> ORGANISM: Artificial Sequence
<220> FEATURE:
<223> OTHER INFORMATION: Synthetic

<400> SEQUENCE: 185
gaggtgcagc tggtggagtc tggggggaggc ttggtccagc ctggggggtc cctgagactc        60
tcctgtgcag cctctggatt caccttcagt acctacgaca tgcactgggt ccgccaagct       120
ccaggaaaag gtctgagtg gtctcagct attggttctg ctggtgacac atactatcca        180
ggctccgtga agggccgatt caccatctcc agagacaatg ccaagagctc cttgtttctt       240
caaatgaaca gcctgagagc cggggacacg gctctatatt actgtgcaag aggagatagt       300
cggaactact cgttgggga ctactttgac tactggggcc agggaaccct ggtcaccgtc       360
tcctca                                                                 366

<210> SEQ ID NO 186
<211> LENGTH: 122
<212> TYPE: PRT
<213> ORGANISM: Artificial Sequence
<220> FEATURE:
<223> OTHER INFORMATION: Synthetic

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Asp Met His Trp Val Arg Gln Ala Pro Gly Lys Gly Leu Glu Trp Val
        35                  40                  45

Ser Ala Ile Gly Ser Ala Gly Asp Thr Tyr Tyr Pro Gly Ser Val Lys
    50                  55                  60

Gly Arg Phe Thr Ile Ser Arg Asp Asn Ala Lys Ser Ser Leu Phe Leu
65                  70                  75                  80

Gln Met Asn Ser Leu Arg Ala Gly Asp Thr Ala Leu Tyr Tyr Cys Ala
                85                  90                  95

Arg Gly Asp Ser Arg Asn Tyr Phe Val Gly Asp Tyr Phe Asp Tyr Trp
            100                 105                 110

Gly Gln Gly Thr Leu Val Thr Val Ser Ser
        115                 120

<210> SEQ ID NO 187
<211> LENGTH: 321
<212> TYPE: DNA
<213> ORGANISM: Artificial Sequence
<220> FEATURE:
<223> OTHER INFORMATION: Synthetic

<400> SEQUENCE: 187
gacatccaga tgacccagtc tccttccacc ctgtctgcat ctgtaggaga cagagtcacc     60
atcacttgcc gggccagtca gagtattggt acctggttgg cctggtatca gcagaaacca    120
gggaaagccc ctaagatcct gatctataag gcgtctagtt tagaaggtgg ggtcccatca    180
aggttcagcg gcagtggatc tgggacagaa ttcactctca ccatcagcag cctgcagcct    240
gatgattttg caaattacta ctgccaacag tataatagtt tttatcggac gttcggccaa    300
gggaccaagg tggaaatcaa a                                              321

<210> SEQ ID NO 188
<211> LENGTH: 107
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Thr Trp
            20                  25                  30

Leu Ala Trp Tyr Gln Gln Lys Pro Gly Lys Ala Pro Lys Ile Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro

```
                65                  70                  75                  80
Asp Asp Phe Ala Asn Tyr Tyr Cys Gln Gln Tyr Asn Ser Phe Tyr Arg
                    85                  90                  95
Thr Phe Gly Gln Gly Thr Lys Val Glu Ile Lys
            100                 105
```

<210> SEQ ID NO 189
<211> LENGTH: 366
<212> TYPE: DNA
<213> ORGANISM: Artificial Sequence
<220> FEATURE:
<223> OTHER INFORMATION: Synthetic

<400> SEQUENCE: 189

```
gaggtgcagc tggtggagtc tgggggaggc ttggtacagc ctgggggggtc cctgagactc      60
tcctgtgcag cctctggatt caccttcagt acctacgaca tgcactgggt ccgccaagct     120
acaggaaaag gtctggagtg ggtctcagct attggttctg ctggtgacac atactatcca     180
ggctccgtga agggccgatt caccatctcc agagaaaatg ccaagaactc cttgtatctt     240
caaatgaaca gcctgagagc cggggacacg gctgtgtatt actgtgcaag aggagatagt     300
cggaactact tcgttgggga ctactttgac tactggggcc agggaaccct ggtcaccgtc     360
tcctca                                                                 366
```

<210> SEQ ID NO 190
<211> LENGTH: 122
<212> TYPE: PRT
<213> ORGANISM: Artificial Sequence
<220> FEATURE:
<223> OTHER INFORMATION: Synthetic

<400> SEQUENCE: 190

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Thr Tyr
            20                  25                  30
Asp Met His Trp Val Arg Gln Ala Thr Gly Lys Gly Leu Glu Trp Val
        35                  40                  45
Ser Ala Ile Gly Ser Ala Gly Asp Thr Tyr Tyr Pro Gly Ser Val Lys
    50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Ala
                85                  90                  95
Arg Gly Asp Ser Arg Asn Tyr Phe Val Gly Asp Tyr Phe Asp Tyr Trp
            100                 105                 110
Gly Gln Gly Thr Leu Val Thr Val Ser Ser
        115                 120
```

<210> SEQ ID NO 191
<211> LENGTH: 322
<212> TYPE: DNA
<213> ORGANISM: Artificial Sequence
<220> FEATURE:
<223> OTHER INFORMATION: Synthetic

<400> SEQUENCE: 191

```
gacatccaga tgacccagtc tccttccacc ctgtctgcat ctgtaggaga cagagtcacc      60
atcacttgcc gggccagtca gagtattggt acctggttgg cctggtatca gcagaaacca     120
```

```
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tataatagtt tttatcggac gttcggccaa      300
gggaccaagg tggaaatcaa ac                                               322
```

<210> SEQ ID NO 192
<211> LENGTH: 107
<212> TYPE: PRT
<213> ORGANISM: Artificial Sequence
<220> FEATURE:
<223> OTHER INFORMATION: Synthetic

<400> SEQUENCE: 192

```
Asp Ile Gln Met Thr Gln Ser Pro Ser Thr Leu Ser Ala Ser Val Gly
  1               5                  10                  15

Asp Arg Val Thr Ile Thr Cys Arg Ala Ser Gln Ser Ile Gly Thr Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Phe Tyr Arg
                 85                  90                  95

Thr Phe Gly Gln Gly Thr Lys Val Glu Ile Lys
            100                 105
```

<210> SEQ ID NO 193
<211> LENGTH: 378
<212> TYPE: DNA
<213> ORGANISM: Artificial Sequence
<220> FEATURE:
<223> OTHER INFORMATION: Synthetic

<400> SEQUENCE: 193

```
caggtgcagc tggtgcagtc tgggggaggc ttggtacagc cggggggggtc cctgagactc      60 tcctgtgcag cctctgaatt cattttagc agctatgcca tgaactgggt ccgccaggct      120
ccagggaagg ggctggagtg gtctcagtc attagtggta gtggtgatag caaatactac      180
gcagactccg tgaagggccg attcaccatc tccagagaca attccaagaa cacactgtat      240
ctgcaaatga acagcctgag agtcgaggac acggccgtgt attactgtgc gaaagatggg      300
aaggacaggt atggtttta ctacaacttc tacggtatgg acgtctgggg ccaagggacc      360
acggtcaccg tctcctca                                                    378
```

<210> SEQ ID NO 194
<211> LENGTH: 126
<212> TYPE: PRT
<213> ORGANISM: Artificial Sequence
<220> FEATURE:
<223> OTHER INFORMATION: Synthetic

<400> SEQUENCE: 194

```
Gln Val Gln Leu Val Gln Ser Gly Gly Gly Leu Val Gln Pro Gly Gly
  1               5                  10                  15

Ser Leu Arg Leu Ser Cys Ala Ala Ser Glu Phe Ile Phe Ser Ser Tyr
                 20                  25                  30

Ala Met Asn Trp Val Arg Gln Ala Pro Gly Lys Gly Leu Glu Trp Val
```

```
                35                  40                  45
Ser Val Ile Ser Gly Ser Gly Asp Ser Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Gly Lys Asp Arg Tyr Gly Phe Tyr Tyr Asn Phe Tyr Gly
            100                 105                 110

Met Asp Val Trp Gly Gln Gly Thr Thr Val Thr Val Ser Ser
            115                 120                 125
```

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
gaattcattt ttagcagcta tgcc                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Glu Phe Ile Phe Ser Ser Tyr Ala
 1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attagtggta gtggtgatag caaa                                          24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Gly Ser Gly Asp Ser Lys
 1               5

<210> SEQ ID NO 199
<211> LENGTH: 57
<212> TYPE: DNA
<213> ORGANISM: Artificial Sequence
<220> FEATURE:
<223> OTHER INFORMATION: Synthetic

<400> SEQUENCE: 199
gcgaaagatg ggaaggacag gtatggtttt tactacaact tctacggtat ggacgtc     57

<210> SEQ ID NO 200
<211> LENGTH: 19
<212> TYPE: PRT
<213> ORGANISM: Artificial Sequence
<220> FEATURE:
<223> OTHER INFORMATION: Synthetic

<400> SEQUENCE: 200

Ala Lys Asp Gly Lys Asp Arg Tyr Gly Phe Tyr Tyr Asn Phe Tyr Gly
 1               5                  10                  15

Met Asp Val

<210> SEQ ID NO 201
<211> LENGTH: 324
<212> TYPE: DNA
<213> ORGANISM: Artificial Sequence
<220> FEATURE:
<223> OTHER INFORMATION: Synthetic

<400> SEQUENCE: 201
gcacatccga tgacccagtc tccatccttc ctgtctgcat ctgtaggaga cagagtcacc      60
atcacttgct gggccagtca gggcataagc agttatttag cctggtatca gcaaaaacca     120
gggaaagccc ctaagatcct gatctatgct gcatccactt tgcaaagtgg ggtcccatca     180
aggttcagcg ccagtgggtc tgggacagaa ttcactctca caatcagcag cctgcagcct     240
gaagattttg caacttatca ctgtcaacag cttaatagtt acccattcac tttcggccct     300
gggaccaagg tggaaatcaa acga                                            324

<210> SEQ ID NO 202
<211> LENGTH: 108
<212> TYPE: PRT
<213> ORGANISM: Artificial Sequence
<220> FEATURE:
<223> OTHER INFORMATION: Synthetic

<400> SEQUENCE: 202

Ala His Pro Met Thr Gln Ser Pro Ser Phe Leu Ser Ala Ser Val Gly
 1               5                  10                  15

Asp Arg Val Thr Ile Thr Cys Trp Ala Ser Gln Gly Ile Ser Ser Tyr
             20                  25                  30

Leu Ala Trp Tyr Gln Gln Lys Pro Gly Lys Ala Pro Lys Ile Leu Ile
         35                  40                  45

Tyr Ala Ala Ser Thr Leu Gln Ser Gly Val Pro Ser Arg Phe Ser Ala
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr His Cys Gln Gln Leu Asn Ser Tyr Pro Phe
                 85                  90                  95

Thr Phe Gly Pro Gly Thr Lys Val Glu Ile Lys Arg
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagggcataa gcagttat                                                    18

```
<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Gly Ile Ser Ser Tyr
 1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 gctgcatcc                                                                 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
 1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagctta atagttaccc attcact                                            27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Leu Asn Ser Tyr Pro Phe Thr
 1               5

<210> SEQ ID NO 209
<211> LENGTH: 375
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ttggtacagc cggggggtc cctgagactc        60 tcctgtgcag cctctgaatt cattttttagc agctatgcca tgaactgggt ccgccaggct     120
ccagggaagg ggctggagtg ggtctcagtc attagtggta gtggtgatag caaatactac     180
gcagactccg tgaagggccg attcaccatc tccagagaca attccaagaa cacactgtat     240
```

```
ctgcaaatga acagcctgag agtcgaggac acggccgtgt attactgtgc gaaagatggg    300
aaggacaggt atggttttta ctacaacttc tacggtatgg acgtctgggg ccaagggacc    360
acggtcaccg tctcc                                                     375
```

<210> SEQ ID NO 210
<211> LENGTH: 125
<212> TYPE: PRT
<213> ORGANISM: Artificial Sequence
<220> FEATURE:
<223> OTHER INFORMATION: Synthetic

<400> SEQUENCE: 210

```
Glu Val Gln Leu Val Glu Ser Gly Gly Gly Leu Val Gln Pro Gly Gly
 1               5                  10                  15

Ser Leu Arg Leu Ser Cys Ala Ala Ser Glu Phe Ile Phe Ser Ser Tyr
            20                  25                  30

Ala Met Asn Trp Val Arg Gln Ala Pro Gly Lys Gly Leu Glu Trp Val
        35                  40                  45

Ser Val Ile Ser Gly Ser Gly Asp Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Gly Lys Asp Arg Tyr Gly Phe Tyr Tyr Asn Phe Tyr Gly
            100                 105                 110

Met Asp Val Trp Gly Gln Gly Thr Thr Val Thr Val Ser
        115                 120                 125
```

<210> SEQ ID NO 211
<211> LENGTH: 321
<212> TYPE: DNA
<213> ORGANISM: Artificial Sequence
<220> FEATURE:
<223> OTHER INFORMATION: Synthetic

<400> SEQUENCE: 211

```
gacatccaga tgacccagtc tccatccttc ctgtctgcat ctgtaggaga cagagtcacc     60
atcacttgct gggccagtca gggcataagc agttatttag cctggtatca gcaaaaacca    120
gggaaagccc ctaagatcct gatctatgct gcatccactt tgcaaagtgg ggtcccatca    180
aggttcagcg ccagtgggtc tgggacagaa ttcactctca caatcagcag cctgcagcct    240
gaagattttg caacttatca ctgtcaacag cttaatagtt acccattcac tttcggccct    300
gggaccaaag tggatatcaa a                                              321
```

<210> SEQ ID NO 212
<211> LENGTH: 107
<212> TYPE: PRT
<213> ORGANISM: Artificial Sequence
<220> FEATURE:
<223> OTHER INFORMATION: Synthetic

<400> SEQUENCE: 212

```
Asp Ile Gln Met Thr Gln Ser Pro Ser Phe Leu Ser Ala Ser Val Gly
 1               5                  10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Ile Leu Ile
        35                  40                  45
```

Tyr Ala Ala Ser Thr Leu Gln Ser Gly Val Pro Ser Arg Phe Ser Ala
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr His Cys Gln Gln Leu Asn Ser Tyr Pro Phe
                 85                  90                  95

Thr Phe Gly Pro Gly Thr Lys Val Asp Ile Lys
             100                 105

<210> SEQ ID NO 213
<211> LENGTH: 376
<212> TYPE: DNA
<213> ORGANISM: Artificial Sequence
<220> FEATURE:
<223> OTHER INFORMATION: Synthetic

<400> SEQUENCE: 213
gaggtgcagc tggtggagtc tgggggaggc ttggtacagc ctggggggtc cctgagactc      60
tcctgtgcag cctctgaatt cattttagc agctatgcca tgagctgggt ccgccaggct     120
ccagggaagg gctggagtg gtctcagct attagtggta gtggtgatag caaatactac     180
gcagactccg tgaagggccg gttcaccatc tccagagaca attccaagaa cacgctgtat    240
ctgcaaatga acagcctgag agccgaggac acggccgtat attactgtgc gaaagatggg    300
aaggacaggt atggtttta ctacaacttc tacggtatgg acgtctgggg ccaagggacc    360
acggtcaccg tctcct                                                     376

<210> SEQ ID NO 214
<211> LENGTH: 125
<212> TYPE: PRT
<213> ORGANISM: Artificial Sequence
<220> FEATURE:
<223> OTHER INFORMATION: Synthetic

<400> SEQUENCE: 214

Glu Val Gln Leu Val Glu Ser Gly Gly Gly Leu Val Gln Pro Gly Gly
 1               5                  10                  15

Ser Leu Arg Leu Ser Cys Ala Ala Ser Glu Phe Ile Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Asp Ser Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Gly Lys Asp Arg Tyr Gly Phe Tyr Tyr Asn Phe Tyr Gly
            100                 105                 110

Met Asp Val Trp Gly Gln Gly Thr Thr Val Thr Val Ser
        115                 120                 125

<210> SEQ ID NO 215
<211> LENGTH: 322
<212> TYPE: DNA
<213> ORGANISM: Artificial Sequence
<220> FEATURE:
<223> OTHER INFORMATION: Synthetic

<400> SEQUENCE: 215

```
gacatccaga tgacccagtc tccatcctcc ctgtctgcat ctgtaggaga cagagtcacc     60
atcacttgcc gggcaagtca gggcataagc agttatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtcaacag cttaatagtt acccattcac tttcggccct    300
gggaccaaag tggatatcaa ac                                             322
```

<210> SEQ ID NO 216
<211> LENGTH: 107
<212> TYPE: PRT
<213> ORGANISM: Artificial Sequence
<220> FEATURE:
<223> OTHER INFORMATION: Synthetic

<400> SEQUENCE: 216

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Phe
                85                  90                  95

Thr Phe Gly Pro Gly Thr Lys Val Asp Ile Lys
            100                 105
```

<210> SEQ ID NO 217
<211> LENGTH: 366
<212> TYPE: DNA
<213> ORGANISM: Artificial Sequence
<220> FEATURE:
<223> OTHER INFORMATION: Synthetic

<400> SEQUENCE: 217

```
gaggtgcagc tggtgcagtc tgggggagac ttggtacagt ctggggggtc cctgagactc     60
tcctgtgcag cctctggatt caccttcagt tcctacgaca tgcactgggt ccgccaagtt    120
aaaggaaaag gtctggagtg ggtctcagct attggaactg ctggtgacac atactatcaa    180
ggctccgtga agggccgatt caccatctcc agagaaaatg ccaagaactc cttgtttctt    240
caaatgaaca gcctgagagc cggggacacg gctgtatatt actgtgcaag aggagatagt    300
agaaactact cgttgggga ctactttgac tactggggcc agggaaccac ggtcaccgtc    360
tcctca                                                               366
```

<210> SEQ ID NO 218
<211> LENGTH: 122
<212> TYPE: PRT
<213> ORGANISM: Artificial Sequence
<220> FEATURE:
<223> OTHER INFORMATION: Synthetic

<400> SEQUENCE: 218

```
Glu Val Gln Leu Val Gln Ser Gly Gly Asp Leu Val Gln Ser Gly Gly
 1               5                  10                  15
```

Ser Leu Arg Leu Ser Cys Ala Ala Ser Gly Phe Thr Phe Ser Ser Tyr
            20                  25                  30

Asp Met His Trp Val Arg Gln Val Lys Gly Lys Gly Leu Glu Trp Val
        35                  40                  45

Ser Ala Ile Gly Thr Ala Gly Asp Thr Tyr Tyr Gln Gly Ser Val Lys
    50                  55                  60

Gly Arg Phe Thr Ile Ser Arg Glu Asn Ala Lys Asn Ser Leu Phe Leu
65                  70                  75                  80

Gln Met Asn Ser Leu Arg Ala Gly Asp Thr Ala Val Tyr Tyr Cys Ala
                85                  90                  95

Arg Gly Asp Ser Arg Asn Tyr Phe Val Gly Asp Tyr Phe Asp Tyr Trp
            100                 105                 110

Gly Gln Gly Thr Thr Val Thr Val Ser Ser
            115                 120

<210> SEQ ID NO 219
<211> LENGTH: 24
<212> TYPE: DNA
<213> ORGANISM: Artificial Sequence
<220> FEATURE:
<223> OTHER INFORMATION: Synthetic

<400> SEQUENCE: 219
ggattcacct tcagttccta cgac                                          24

<210> SEQ ID NO 220
<211> LENGTH: 8
<212> TYPE: PRT
<213> ORGANISM: Artificial Sequence
<220> FEATURE:
<223> OTHER INFORMATION: Synthetic

<400> SEQUENCE: 220

Gly Phe Thr Phe Ser Ser Tyr Asp
1               5

<210> SEQ ID NO 221
<211> LENGTH: 21
<212> TYPE: DNA
<213> ORGANISM: Artificial Sequence
<220> FEATURE:
<223> OTHER INFORMATION: Synthetic

<400> SEQUENCE: 221
attggaactg ctggtgacac a                                             21

<210> SEQ ID NO 222
<211> LENGTH: 7
<212> TYPE: PRT
<213> ORGANISM: Artificial Sequence
<220> FEATURE:
<223> OTHER INFORMATION: Synthetic

<400> SEQUENCE: 222

Ile Gly Thr Ala Gly Asp Thr
1               5

<210> SEQ ID NO 223
<211> LENGTH: 48
<212> TYPE: DNA
<213> ORGANISM: Artificial Sequence
<220> FEATURE:
<223> OTHER INFORMATION: Synthetic

<400> SEQUENCE: 223
gcaagaggag atagtagaaa ctacttcgtt ggggactact ttgactac            48

<210> SEQ ID NO 224
<211> LENGTH: 16
<212> TYPE: PRT
<213> ORGANISM: Artificial Sequence
<220> FEATURE:
<223> OTHER INFORMATION: Synthetic

<400> SEQUENCE: 224

Ala Arg Gly Asp Ser Arg Asn Tyr Phe Val Gly Asp Tyr Phe Asp Tyr
 1               5                  10                  15

<210> SEQ ID NO 225
<211> LENGTH: 324
<212> TYPE: DNA
<213> ORGANISM: Artificial Sequence
<220> FEATURE:
<223> OTHER INFORMATION: Synthetic

<400> SEQUENCE: 225
gacatccaga tgacccagtc tccttccacc ctgtctgcat ctgtaggaga cagagtcacc     60
atcacttgcc gggccagtca gagtattagt aactggttgg cctggtatca gcagaaacca    120
gggaaagccc ctaaggtcct gatctataag gcgtctaatt tagaaggtgg ggtcccatca    180
aggttcagcg gcagtggatc tgggacagaa ttcactctca ccataagcaa cctgcagcct    240
gatgattttg caacttatta ctgccaacag tataatagtt attctcggac gttcggccaa    300
gggaccaagg tggaaatcaa acga                                          324

<210> SEQ ID NO 226
<211> LENGTH: 108
<212> TYPE: PRT
<213> ORGANISM: Artificial Sequence
<220> FEATURE:
<223> OTHER INFORMATION: Synthetic

<400> SEQUENCE: 226

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Val Leu Ile
        35                  40                  45

Tyr Lys Ala Ser Asn Leu Glu Gly Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Arg
            100                 105

<210> SEQ ID NO 227
<211> LENGTH: 18
<212> TYPE: DNA
<213> ORGANISM: Artificial Sequence
<220> FEATURE:
<223> OTHER INFORMATION: Synthetic

<400> SEQUENCE: 227

```
cagagtatta gtaactgg                                                       18

<210> SEQ ID NO 228
<211> LENGTH: 6
<212> TYPE: PRT
<213> ORGANISM: Artificial Sequence
<220> FEATURE:
<223> OTHER INFORMATION: Synthetic

<400> SEQUENCE: 228

Gln Ser Ile Ser Asn Trp
 1               5

<210> SEQ ID NO 229
<211> LENGTH: 9
<212> TYPE: DNA
<213> ORGANISM: Artificial Sequence
<220> FEATURE:
<223> OTHER INFORMATION: Synthetic

<400> SEQUENCE: 229 aaggcgtct                                                                  9

<210> SEQ ID NO 230
<211> LENGTH: 3
<212> TYPE: PRT
<213> ORGANISM: Artificial Sequence
<220> FEATURE:
<223> OTHER INFORMATION: Synthetic

<400> SEQUENCE: 230

Lys Ala Ser
 1

<210> SEQ ID NO 231
<211> LENGTH: 27
<212> TYPE: DNA
<213> ORGANISM: Artificial Sequence
<220> FEATURE:
<223> OTHER INFORMATION: Synthetic

<400> SEQUENCE: 231
caacagtata atagttattc tcggacg                                             27

<210> SEQ ID NO 232
<211> LENGTH: 9
<212> TYPE: PRT
<213> ORGANISM: Artificial Sequence
<220> FEATURE:
<223> OTHER INFORMATION: Synthetic

<400> SEQUENCE: 232

Gln Gln Tyr Asn Ser Tyr Ser Arg Thr
 1               5

<210> SEQ ID NO 233
<211> LENGTH: 366
<212> TYPE: DNA
<213> ORGANISM: Artificial Sequence
<220> FEATURE:
<223> OTHER INFORMATION: Synthetic

<400> SEQUENCE: 233
gaggtgcagc tggtggagtc tgggggagac ttggtacagt ctggggggtc cctgagactc         60
tcctgtgcag cctctggatt caccttcagt tcctacgaca tgcactgggt ccgccaagtt        120
aaaggaaaag gtctggagtg ggtctcagct attggaactg ctggtgacac atactatcaa        180
```

```
ggctccgtga agggccgatt caccatctcc agagaaaatg ccaagaactc cttgtttctt      240
caaatgaaca gcctgagagc cggggacacg gctgtatatt actgtgcaag aggagatagt      300
agaaactact tcgttgggga ctactttgac tactggggcc agggaaccct ggtcaccgtc      360
tcctca                                                                 366
```

<210> SEQ ID NO 234
<211> LENGTH: 122
<212> TYPE: PRT
<213> ORGANISM: Artificial Sequence
<220> FEATURE:
<223> OTHER INFORMATION: Synthetic

<400> SEQUENCE: 234

```
Glu Val Gln Leu Val Glu Ser Gly Gly Asp Leu Val Gln Ser Gly Gly
 1               5                  10                  15

Ser Leu Arg Leu Ser Cys Ala Ala Ser Gly Phe Thr Phe Ser Ser Tyr
             20                  25                  30

Asp Met His Trp Val Arg Gln Val Lys Gly Lys Gly Leu Glu Trp Val
         35                  40                  45

Ser Ala Ile Gly Thr Ala Gly Asp Thr Tyr Tyr Gln Gly Ser Val Lys
     50                  55                  60

Gly Arg Phe Thr Ile Ser Arg Glu Asn Ala Lys Asn Ser Leu Phe Leu
 65                  70                  75                  80

Gln Met Asn Ser Leu Arg Ala Gly Asp Thr Ala Val Tyr Tyr Cys Ala
                 85                  90                  95

Arg Gly Asp Ser Arg Asn Tyr Phe Val Gly Asp Tyr Phe Asp Tyr Trp
            100                 105                 110

Gly Gln Gly Thr Leu Val Thr Val Ser Ser
        115                 120
```

<210> SEQ ID NO 235
<211> LENGTH: 321
<212> TYPE: DNA
<213> ORGANISM: Artificial Sequence
<220> FEATURE:
<223> OTHER INFORMATION: Synthetic

<400> SEQUENCE: 235

```
gacatccaga tgacccagtc tccttccacc ctgtctgcat ctgtaggaga cagagtcacc       60
atcacttgcc gggccagtca gagtattagt aactggttgg cctggtatca gcagaaacca      120
gggaaagccc ctaaggtcct gatctataag gcgtctaatt tagaaggtgg ggtcccatca      180
aggttcagcg gcagtggatc tgggacagaa ttcactctca ccataagcaa cctgcagcct      240
gatgattttg caacttatta ctgccaacag tataatagtt attctcggac gttcggccaa      300
gggaccaagg tggaaatcaa a                                                321
```

<210> SEQ ID NO 236
<211> LENGTH: 107
<212> TYPE: PRT
<213> ORGANISM: Artificial Sequence
<220> FEATURE:
<223> OTHER INFORMATION: Synthetic

<400> SEQUENCE: 236

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Trp
             20                  25                  30
```

Leu Ala Trp Tyr Gln Gln Lys Pro Gly Lys Ala Pro Lys Val Leu Ile
            35                  40                  45

Tyr Lys Ala Ser Asn Leu Glu Gly Gly Val Pro Ser Arg Phe Ser Gly
        50                  55                  60

Ser Gly Ser Gly Thr Glu Phe Thr Leu Thr Ile Ser Asn Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 237
<211> LENGTH: 366
<212> TYPE: DNA
<213> ORGANISM: Artificial Sequence
<220> FEATURE:
<223> OTHER INFORMATION: Synthetic

<400> SEQUENCE: 237
gaggtgcagc tggtggagtc tgggggaggc ttggtacagc ctgggggtc cctgagactc    60 tcctgtgcag cctctggatt caccttcagt tcctacgaca tgcactgggt ccgccaagct   120
acaggaaaag gtctggagtg ggtctcagct attggaactg ctggtgacac atactatcca   180
ggctccgtga agggccgatt caccatctcc agagaaaatg ccaagaactc cttgtatctt   240
caaatgaaca gcctgagagc cggggacacg gctgtgtatt actgtgcaag aggagatagt   300
agaaactact tcgttgggga ctactttgac tactggggcc agggaaccct ggtcaccgtc   360
tcctca                                                              366

<210> SEQ ID NO 238
<211> LENGTH: 122
<212> TYPE: PRT
<213> ORGANISM: Artificial Sequence
<220> FEATURE:
<223> OTHER INFORMATION: Synthetic

<400> SEQUENCE: 238

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Ser Arg Asn Tyr Phe Val Gly Asp Tyr Phe Asp Tyr Trp
            100                 105                 110

Gly Gln Gly Thr Leu Val Thr Val Ser Ser
        115                 120

<210> SEQ ID NO 239
<211> LENGTH: 322
<212> TYPE: DNA
<213> ORGANISM: Artificial Sequence
<220> FEATURE:

<210> SEQ ID NO 239 (continued)
<223> OTHER INFORMATION: Synthetic

<400> SEQUENCE: 239

```
gacatccaga tgacccagtc tccttccacc ctgtctgcat ctgtaggaga cagagtcacc     60
atcacttgcc gggccagtca gagtattagt aactggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attctcggac gttcggccaa    300
gggaccaagg tggaaatcaa ac                                              322
```

<210> SEQ ID NO 240
<211> LENGTH: 107
<212> TYPE: PRT
<213> ORGANISM: Artificial Sequence
<220> FEATURE:
<223> OTHER INFORMATION: Synthetic

<400> SEQUENCE: 240

```
Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105
```

<210> SEQ ID NO 241
<211> LENGTH: 366
<212> TYPE: DNA
<213> ORGANISM: Artificial Sequence
<220> FEATURE:
<223> OTHER INFORMATION: Synthetic

<400> SEQUENCE: 241

```
caggtgcagc tggtgcagtc tggggggaggc ttggtgcagc ctggggggtc cctgagactc     60
tcctgtgtag cctctggatt caccttcagt agctacgaca tgcactgggt ccgccaagtt    120
gcaggaaaag gtctggagtg ggtcgcagcc attggtactg ctggtgacac atactatcca    180
gtctccgtga agggccgatt caccatctct agagaaaatg ccaagaactc cttgtctctt    240
cacatgaaca gcctgagagc cggggacacg gctgtgtatt actgtgcaag aggagacagt    300
agaaactact acgttgggga ctactttgac tactggggcc agggaaccac ggtcaccgtc    360
tcctca                                                                366
```

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Gln Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Asp Met His Trp Val Arg Gln Val Ala Gly Lys Gly Leu Glu Trp Val
        35                  40                  45

Ala Ala Ile Gly Thr Ala Gly Asp Thr Tyr Tyr Pro Val Ser Val Lys
    50                  55                  60

Gly Arg Phe Thr Ile Ser Arg Glu Asn Ala Lys Asn Ser Leu Ser Leu
65              70                  75                  80

His Met Asn Ser Leu Arg Ala Gly Asp Thr Ala Val Tyr Tyr Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Thr Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagtagcta cgac                                    24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Ser Tyr Asp
1               5

<210> SEQ ID NO 245
<211> LENGTH: 21
<212> TYPE: DNA
<213> ORGANISM: Artificial Sequence
<220> FEATURE:
<223> OTHER INFORMATION: Synthetic

<400> SEQUENCE: 245
attggtactg ctggtgacac a                                       21

<210> SEQ ID NO 246
<211> LENGTH: 7
<212> TYPE: PRT
<213> ORGANISM: Artificial Sequence
<220> FEATURE:
<223> OTHER INFORMATION: Synthetic

<400> SEQUENCE: 246

Ile Gly Thr Ala Gly Asp Thr
1               5

<210> SEQ ID NO 247
<211> LENGTH: 48
<212> TYPE: DNA
<213> ORGANISM: Artificial Sequence

```
<220> FEATURE:
<223> OTHER INFORMATION: Synthetic

<400> SEQUENCE: 247
gcaagaggag acagtagaaa ctactacgtt ggggactact ttgactac          48

<210> SEQ ID NO 248
<211> LENGTH: 16
<212> TYPE: PRT
<213> ORGANISM: Artificial Sequence
<220> FEATURE:
<223> OTHER INFORMATION: Synthetic

<400> SEQUENCE: 248

Ala Arg Gly Asp Ser Arg Asn Tyr Tyr Val Gly Asp Tyr Phe Asp Tyr
 1               5                  10                  15

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccttccacc ctgtctgcat ctgtaggaga cagagtcacc     60
atcacttgcc gggccagtca gagtattagt aggtggttgg cctggtatca gcaaaaacca   120
gggaaagccc ctaaggtcct gatctataag gcgtctagtt taaaaagtgg ggtcccatca   180
aggttcagcg gcagtggatc tgggacagaa ttcactctca ccatcagcag cctgcagtct   240
gatgattttg caacttatta ctgccaacag tataatagtt attctcggac gttcggccaa   300
gggaccaagg tggagatcaa acga                                          324

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Arg Trp
                20                  25                  30

Leu Ala Trp Tyr Gln Gln Lys Pro Gly Lys Ala Pro Lys Val Leu Ile
            35                  40                  45

Tyr Lys Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys Arg
            100                 105

<210> SEQ ID NO 251
<211> LENGTH: 18
<212> TYPE: DNA
<213> ORGANISM: Artificial Sequence
<220> FEATURE:
<223> OTHER INFORMATION: Synthetic
```

<400> SEQUENCE: 251
cagagtatta gtaggtgg                                             18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Ser Ile Ser Arg Trp
 1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 aaggcgtct                                                        9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Lys Ala Ser
 1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacagtata atagttattc tcggacg                                   27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Tyr Asn Ser Tyr Ser Arg Thr
 1               5

<210> SEQ ID NO 257
<211> LENGTH: 366
<212> TYPE: DNA
<213> ORGANISM: Artificial Sequence
<220> FEATURE:
<223> OTHER INFORMATION: Synthetic

<400> SEQUENCE: 257
gaggtgcagc tggtggagtc tgggggaggc ttggtgcagc ctggggggtc cctgagactc     60

-continued

```
tcctgtgtag cctctggatt caccttcagt agctacgaca tgcactgggt ccgccaagtt      120
gcaggaaaag gtctggagtg ggtcgcagcc attggtactg ctggtgacac atactatcca      180
gtctccgtga agggccgatt caccatctct agagaaaatg ccaagaactc cttgtctctt      240
cacatgaaca gcctgagagc cggggacacg gctgtgtatt actgtgcaag aggagacagt      300
agaaactact acgttgggga ctactttgac tactggggcc agggaaccct ggtcaccgtc      360
tcctca                                                                 366
```

<210> SEQ ID NO 258
<211> LENGTH: 122
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Val Glu Ser Gly Gly Gly Leu Val Gln Pro Gly Gly
 1               5                  10                  15

Ser Leu Arg Leu Ser Cys Val Ala Ser Gly Phe Thr Phe Ser Ser Tyr
            20                  25                  30

Asp Met His Trp Val Arg Gln Val Ala Gly Lys Gly Leu Glu Trp Val
        35                  40                  45

Ala Ala Ile Gly Thr Ala Gly Asp Thr Tyr Tyr Pro Val Ser Val Lys
    50                  55                  60

Gly Arg Phe Thr Ile Ser Arg Glu Asn Ala Lys Asn Ser Leu Ser Leu
65                  70                  75                  80

His Met Asn Ser Leu Arg Ala Gly Asp Thr Ala Val Tyr Tyr Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Leu Val Thr Val Ser Ser
        115                 120
```

<210> SEQ ID NO 259
<211> LENGTH: 321
<212> TYPE: DNA
<213> ORGANISM: Artificial Sequence
<220> FEATURE:
<223> OTHER INFORMATION: Synthetic

<400> SEQUENCE: 259

```
gacatccaga tgacccagtc tccttccacc ctgtctgcat ctgtaggaga cagagtcacc       60
atcacttgcc gggccagtca gagtattagt aggtggttgg cctggtatca gcaaaaacca      120
gggaaagccc ctaaggtcct gatctataag gcgtctagtt taaaaagtgg ggtcccatca      180
aggttcagcg gcagtggatc tgggacagaa ttcactctca ccatcagcag cctgcagtct      240
gatgattttg caacttatta ctgccaacag tataatagtt attctcggac gttcggccaa      300
gggaccaagg tggaaatcaa a                                                321
```

<210> SEQ ID NO 260
<211> LENGTH: 107
<212> TYPE: PRT
<213> ORGANISM: Artificial Sequence
<220> FEATURE:
<223> OTHER INFORMATION: Synthetic

<400> SEQUENCE: 260

```
Asp Ile Gln Met Thr Gln Ser Pro Ser Thr Leu Ser Ala Ser Val Gly
 1               5                  10                  15
```

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Val Leu Ile
        35                  40                  45

Tyr Lys Ala Ser Ser Leu Lys Ser Gly Val Pro Ser Arg Phe Ser Gly
    50                  55                  60

Ser Gly Ser Gly Thr Glu Phe Thr Leu Thr Ile Ser Ser Leu Gln Ser
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 261
<211> LENGTH: 366
<212> TYPE: DNA
<213> ORGANISM: Artificial Sequence
<220> FEATURE:
<223> OTHER INFORMATION: Synthetic

<400> SEQUENCE: 261
gaggtgcagc tggtggagtc tgggggaggc ttggtacagc ctggggggtc cctgagactc      60
tcctgtgcag cctctggatt caccttcagt agctacgaca tgcactgggt ccgccaagct     120
acaggaaaag gtctggagtg ggtctcagct attggtactg ctggtgacac atactatcca     180
ggctccgtga aggccgatt caccatctcc agagaaaatg ccaagaactc cttgtatctt     240
caaatgaaca gcctgagagc cggggacacg gctgtgtatt actgtgcaag aggagacagt     300
agaaactact acgttgggga ctactttgac tactggggcc agggaaccct ggtcaccgtc     360
tcctca                                                                366

<210> SEQ ID NO 262
<211> LENGTH: 122
<212> TYPE: PRT
<213> ORGANISM: Artificial Sequence
<220> FEATURE:
<223> OTHER INFORMATION: Synthetic

<400> SEQUENCE: 262

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Leu Val Thr Val Ser Ser
        115                 120

<210> SEQ ID NO 263
<211> LENGTH: 322

<212> TYPE: DNA
<213> ORGANISM: Artificial Sequence
<220> FEATURE:
<223> OTHER INFORMATION: Synthetic

<400> SEQUENCE: 263

```
gacatccaga tgacccagtc tccttccacc ctgtctgcat ctgtaggaga cagagtcacc      60
atcacttgcc gggccagtca gagtattagt aggtggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt attctcggac gttcggccaa     300
gggaccaagg tggaaatcaa ac                                              322
```

<210> SEQ ID NO 264
<211> LENGTH: 107
<212> TYPE: PRT
<213> ORGANISM: Artificial Sequence
<220> FEATURE:
<223> OTHER INFORMATION: Synthetic

<400> SEQUENCE: 264

```
Asp Ile Gln Met Thr Gln Ser Pro Ser Thr Leu Ser Ala Ser Val Gly
  1               5                  10                  15
Asp Arg Val Thr Ile Thr Cys Arg Ala Ser Gln Ser Ile Ser Arg Trp
             20                  25                  30
Leu Ala Trp Tyr Gln Gln Lys Pro Gly Lys Ala Pro Lys Leu Leu Ile
         35                  40                  45
Tyr Lys Ala Ser Ser Leu Glu Ser Gly Val Pro Ser Arg Phe Ser Gly
     50                  55                  60
Ser Gly Ser Gly Thr Glu Phe Thr Leu Thr Ile Ser Ser Leu Gln Pro
 65                  70                  75                  80
Asp Asp Phe Ala Thr Tyr Tyr Cys Gln Gln Tyr Asn Ser Tyr Ser Arg
                 85                  90                  95
Thr Phe Gly Gln Gly Thr Lys Val Glu Ile Lys
            100                 105
```

<210> SEQ ID NO 265
<211> LENGTH: 366
<212> TYPE: DNA
<213> ORGANISM: Artificial Sequence
<220> FEATURE:
<223> OTHER INFORMATION: Synthetic

<400> SEQUENCE: 265

```
caggtgcagc tggtacagtc tgggggaggc ttggtgcagc ctgggggtc cctgagactc       60
tcctgtgcag cctctggatt caccttcagt agctacgaca tgcactgggt ccgccaagtt    120
gcaggaaaag gtctggagtg ggtctcagcc attggtactg ctggtgacac atactatcca    180
gtctccgtga agggccgatt caccatctct agagaaaatg ccaagaactc cttgtatctt    240
cacatgaaca gcctgagagc cggggatacg gctgtgtatt actgtgcaag aggagacagt    300
agaaactact acgttgggga ctactttgac tactggggcc agggaaccac ggtcaccgtc    360
tcctca                                                               366
```

<210> SEQ ID NO 266
<211> LENGTH: 122
<212> TYPE: PRT
<213> ORGANISM: Artificial Sequence
<220> FEATURE:

<223> OTHER INFORMATION: Synthetic

<400> SEQUENCE: 266

Gln Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Val Ala Gly Lys Gly Leu Glu Trp Val
        35                  40                  45

Ser Ala Ile Gly Thr Ala Gly Asp Thr Tyr Tyr Pro Val Ser Val Lys
    50                  55                  60

Gly Arg Phe Thr Ile Ser Arg Glu Asn Ala Lys Asn Ser Leu Tyr Leu
65                  70                  75                  80

His Met Asn Ser Leu Arg Ala Gly Asp Thr Ala Val Tyr Tyr Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Thr Val Thr Val Ser Ser
        115                 120

<210> SEQ ID NO 267
<211> LENGTH: 24
<212> TYPE: DNA
<213> ORGANISM: Artificial Sequence
<220> FEATURE:
<223> OTHER INFORMATION: Synthetic

<400> SEQUENCE: 267
ggattcacct tcagtagcta cgac                                          24

<210> SEQ ID NO 268
<211> LENGTH: 8
<212> TYPE: PRT
<213> ORGANISM: Artificial Sequence
<220> FEATURE:
<223> OTHER INFORMATION: Synthetic

<400> SEQUENCE: 268

Gly Phe Thr Phe Ser Ser Tyr Asp
1               5

<210> SEQ ID NO 269
<211> LENGTH: 21
<212> TYPE: DNA
<213> ORGANISM: Artificial Sequence
<220> FEATURE:
<223> OTHER INFORMATION: Synthetic

<400> SEQUENCE: 269
attggtactg ctggtgacac a                                             21

<210> SEQ ID NO 270
<211> LENGTH: 7
<212> TYPE: PRT
<213> ORGANISM: Artificial Sequence
<220> FEATURE:
<223> OTHER INFORMATION: Synthetic

<400> SEQUENCE: 270

Ile Gly Thr Ala Gly Asp Thr
1               5

<210> SEQ ID NO 271

```
<211> LENGTH: 48
<212> TYPE: DNA
<213> ORGANISM: Artificial Sequence
<220> FEATURE:
<223> OTHER INFORMATION: Synthetic

<400> SEQUENCE: 271
gcaagaggag acagtagaaa ctactacgtt ggggactact ttgactac          48

<210> SEQ ID NO 272
<211> LENGTH: 16
<212> TYPE: PRT
<213> ORGANISM: Artificial Sequence
<220> FEATURE:
<223> OTHER INFORMATION: Synthetic

<400> SEQUENCE: 272

Ala Arg Gly Asp Ser Arg Asn Tyr Tyr Val Gly Asp Tyr Phe Asp Tyr
 1               5                  10                  15

<210> SEQ ID NO 273
<211> LENGTH: 324
<212> TYPE: DNA
<213> ORGANISM: Artificial Sequence
<220> FEATURE:
<223> OTHER INFORMATION: Synthetic

<400> SEQUENCE: 273
gacatccagt tgacccagtc tccttccacc ctgtctgcat ctgtaggaga cagagtcacc    60
atcacttgcc gggccagtca gagtattagt aggtggttgg cctggtatca gcaaaaacca   120
gggaaagccc ctaaggtcct gatctataag gcgtctaatt tagaaagtgg ggtcccatca   180
aggttcagcg gcagtggatc tgggacagaa ttcactctca ccatcagcag cctgcagcct   240
gatgattttg caacttatta ctgccaacag tataatactt attctcggac gttcggccaa   300
gggaccaagg tggaaatcaa acga                                          324

<210> SEQ ID NO 274
<211> LENGTH: 108
<212> TYPE: PRT
<213> ORGANISM: Artificial Sequence
<220> FEATURE:
<223> OTHER INFORMATION: Synthetic

<400> SEQUENCE: 274

Asp Ile Gln Leu Thr Gln Ser Pro Ser Thr Leu Ser Ala Ser Val Gly
 1               5                  10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Val Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Ser Arg
                85                  90                  95

Thr Phe Gly Gln Gly Thr Lys Val Glu Ile Lys Arg
            100                 105

<210> SEQ ID NO 275
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 275
cagagtatta gtaggtgg                                                 18

<210> SEQ ID NO 276
<211> LENGTH: 6
<212> TYPE: PRT
<213> ORGANISM: Artificial Sequence
<220> FEATURE:
<223> OTHER INFORMATION: Synthetic

<400> SEQUENCE: 276

Gln Ser Ile Ser Arg Trp
 1               5

<210> SEQ ID NO 277
<211> LENGTH: 9
<212> TYPE: DNA
<213> ORGANISM: Artificial Sequence
<220> FEATURE:
<223> OTHER INFORMATION: Synthetic

<400> SEQUENCE: 277 aaggcgtct                                                            9

<210> SEQ ID NO 278
<211> LENGTH: 3
<212> TYPE: PRT
<213> ORGANISM: Artificial Sequence
<220> FEATURE:
<223> OTHER INFORMATION: Synthetic

<400> SEQUENCE: 278

Lys Ala Ser
 1

<210> SEQ ID NO 279
<211> LENGTH: 27
<212> TYPE: DNA
<213> ORGANISM: Artificial Sequence
<220> FEATURE:
<223> OTHER INFORMATION: Synthetic

<400> SEQUENCE: 279
caacagtata atacttattc tcggacg                                       27

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Gln Gln Tyr Asn Thr Tyr Ser Arg Thr
 1               5

<210> SEQ ID NO 281
<211> LENGTH: 366
<212> TYPE: DNA
<213> ORGANISM: Artificial Sequence
<220> FEATURE:
<223> OTHER INFORMATION: Synthetic

<400> SEQUENCE: 281
```

```
gaggtgcagc tggtggagtc tggggggaggc ttggtgcagc ctgggggggtc cctgagactc    60 tcctgtgcag cctctggatt caccttcagt agctacgaca tgcactgggt ccgccaagtt   120
gcaggaaaag gtctggagtg gtctcagcc attggtactg ctggtgacac atactatcca    180
gtctccgtga agggccgatt caccatctct agagaaaatg ccaagaactc cttgtatctt   240
cacatgaaca gcctgagagc cggggatacg gctgtgtatt actgtgcaag aggagacagt   300
agaaactact acgttgggga ctactttgac tactggggcc agggaaccct ggtcaccgtc   360
tcctca                                                               366
```

<210> SEQ ID NO 282
<211> LENGTH: 122
<212> TYPE: PRT
<213> ORGANISM: Artificial Sequence
<220> FEATURE:
<223> OTHER INFORMATION: Synthetic

<400> SEQUENCE: 282

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Asp Met His Trp Val Arg Gln Val Ala Gly Lys Gly Leu Glu Trp Val
        35                  40                  45

Ser Ala Ile Gly Thr Ala Gly Asp Thr Tyr Tyr Pro Val Ser Val Lys
    50                  55                  60

Gly Arg Phe Thr Ile Ser Arg Glu Asn Ala Lys Asn Ser Leu Tyr Leu
65                  70                  75                  80

His Met Asn Ser Leu Arg Ala Gly Asp Thr Ala Val Tyr Tyr Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Leu Val Thr Val Ser Ser
        115                 120
```

<210> SEQ ID NO 283
<211> LENGTH: 321
<212> TYPE: DNA
<213> ORGANISM: Artificial Sequence
<220> FEATURE:
<223> OTHER INFORMATION: Synthetic

<400> SEQUENCE: 283

```
gacatccaga tgacccagtc tccttccacc ctgtctgcat ctgtaggaga cagagtcacc    60
atcacttgcc gggccagtca gagtattagt aggtggttgg cctggtatca gcaaaaacca   120
gggaaagccc ctaaggtcct gatctataag gcgtctaatt tagaaagtgg ggtcccatca   180
aggttcagcg gcagtggatc tgggacagaa ttcactctca ccatcagcag cctgcagcct   240
gatgattttg caacttatta ctgccaacag tataatactt attctcggac gttcggccaa   300
gggaccaagg tggaaatcaa a                                              321
```

<210> SEQ ID NO 284
<211> LENGTH: 107
<212> TYPE: PRT
<213> ORGANISM: Artificial Sequence
<220> FEATURE:
<223> OTHER INFORMATION: Synthetic

<400> SEQUENCE: 284

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Val Leu Ile
        35                  40                  45

Tyr Lys Ala Ser Asn Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65              70                  75                  80

Asp Asp Phe Ala Thr Tyr Tyr Cys Gln Gln Tyr Asn Thr Tyr Ser Arg
                85                  90                  95

Thr Phe Gly Gln Gly Thr Lys Val Glu Ile Lys
            100                 105

<210> SEQ ID NO 285
<211> LENGTH: 366
<212> TYPE: DNA
<213> ORGANISM: Artificial Sequence
<220> FEATURE:
<223> OTHER INFORMATION: Synthetic

<400> SEQUENCE: 285
gaggtgcagc tggtggagtc tgggggaggc ttggtacagc ctggggggtc cctgagactc     60
tcctgtgcag cctctggatt caccttcagt agctacgaca tgcactgggt ccgccaagct    120
acaggaaaag gtctggagtg ggtctcagct attggtactg ctggtgacac atactatcca    180
ggctccgtga agggccgatt caccatctcc agagaaaatg ccaagaactc cttgtatctt    240
caaatgaaca gcctgagagc cggggacacg gctgtgtatt actgtgcaag aggagacagt    300
agaaactact acgttgggga ctactttgac tactggggcc agggaaccct ggtcaccgtc    360
tcctca                                                               366

<210> SEQ ID NO 286
<211> LENGTH: 122
<212> TYPE: PRT
<213> ORGANISM: Artificial Sequence
<220> FEATURE:
<223> OTHER INFORMATION: Synthetic

<400> SEQUENCE: 286

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Asp Thr Tyr Tyr Pro Gly Ser Val Lys
50                  55                  60

Gly Arg Phe Thr Ile Ser Arg Glu Asn Ala Lys Asn Ser Leu Tyr Leu
65              70                  75                  80

Gln Met Asn Ser Leu Arg Ala Gly Asp Thr Ala Val Tyr Tyr Cys Ala
                85                  90                  95

Arg Gly Asp Ser Arg Asn Tyr Tyr Val Gly Asp Tyr Phe Asp Tyr Trp
            100                 105                 110

Gly Gln Gly Thr Leu Val Thr Val Ser Ser
        115                 120

<210> SEQ ID NO 287
<211> LENGTH: 322
<212> TYPE: DNA
<213> ORGANISM: Artificial Sequence
<220> FEATURE:
<223> OTHER INFORMATION: Synthetic

<400> SEQUENCE: 287

```
gacatccaga tgacccagtc tccttccacc ctgtctgcat ctgtaggaga cagagtcacc      60
atcacttgcc gggccagtca gagtattagt aggtggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatactt attctcggac gttcggccaa     300
gggaccaagg tggaaatcaa ac                                              322
```

<210> SEQ ID NO 288
<211> LENGTH: 107
<212> TYPE: PRT
<213> ORGANISM: Artificial Sequence
<220> FEATURE:
<223> OTHER INFORMATION: Synthetic

<400> SEQUENCE: 288

```
Asp Ile Gln Met Thr Gln Ser Pro Ser Thr Leu Ser Ala Ser Val Gly
 1               5                  10                  15
Asp Arg Val Thr Ile Thr Cys Arg Ala Ser Gln Ser Ile Ser Arg Trp
            20                  25                  30
Leu Ala Trp Tyr Gln Gln Lys Pro Gly Lys Ala Pro Lys Leu Leu Ile
        35                  40                  45
Tyr Lys Ala Ser Ser Leu Glu Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asn Thr Tyr Ser Arg
                85                  90                  95
Thr Phe Gly Gln Gly Thr Lys Val Glu Ile Lys
            100                 105
```

<210> SEQ ID NO 289
<211> LENGTH: 363
<212> TYPE: DNA
<213> ORGANISM: Artificial Sequence
<220> FEATURE:
<223> OTHER INFORMATION: Synthetic

<400> SEQUENCE: 289

```
caggtgcagc tgcaggagtc tgggggaggc gtggtccagc ctggagggtc cctgagactc      60
tcctgtgtag cgtctggatt caccttcagc agctatggca tgcactgggt ccgccaggct     120
ccaggcaagg ggctggagtg gatggcagtt atttggtatg atggaagtaa taagtacttt     180
gcagactccg tgaaggaccg attcaccatc tccagagaca attccaagaa cacgctgtat     240
ctgcaaatga acactctgag acctgacgac acggctgtgt attactgtgt gaaggcggac     300
gcccccctcc tgatctatgg tgtggacgtc tggggccaag ggaccacggt caccgtctcc     360
tca                                                                  363
```

<210> SEQ ID NO 290
<211> LENGTH: 121

```
<212> TYPE: PRT
<213> ORGANISM: Artificial Sequence
<220> FEATURE:
<223> OTHER INFORMATION: Synthetic

<400> SEQUENCE: 290

Gln Val Gln Leu Gln Glu Ser Gly Gly Val Val Gln Pro Gly Arg
 1               5                  10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Met
        35                  40                  45

Ala Val Ile Trp Tyr Asp Gly Ser Asn Lys Tyr Phe Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Thr Leu Arg Pro Asp Asp Thr Ala Val Tyr Tyr Cys
                85                  90                  95

Val Lys Ala Asp Ala Pro Leu Leu Ile Tyr Gly Val Asp Val Trp Gly
            100                 105                 110

Gln Gly Thr Thr Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct tcagcagcta tggc                                            24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ser Tyr Gly
 1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
atttggtatg atggaagtaa taag                                            24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Trp Tyr Asp Gly Ser Asn Lys
 1               5
```

<210> SEQ ID NO 295
<211> LENGTH: 42
<212> TYPE: DNA
<213> ORGANISM: Artificial Sequence
<220> FEATURE:
<223> OTHER INFORMATION: Synthetic

<400> SEQUENCE: 295
gtgaaggcgg acgccccct cctgatctat ggtgtggacg tc         42

<210> SEQ ID NO 296
<211> LENGTH: 14
<212> TYPE: PRT
<213> ORGANISM: Artificial Sequence
<220> FEATURE:
<223> OTHER INFORMATION: Synthetic

<400> SEQUENCE: 296

Val Lys Ala Asp Ala Pro Leu Leu Ile Tyr Gly Val Asp Val
 1               5                  10

<210> SEQ ID NO 297
<211> LENGTH: 324
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcctcc ctgtctgcat ctgtaggaga cagagtcacc    60
atcacttgcc gggcaagtca gggcattaga aatgatttag ctggtatcaa agagaaacca   120
ggaaaagccc ctaagcgcct gatctatttt gcatccagtt tgcaaagtgg ggtcccatca   180
aggttcagcg gcagtggatc tgggacagaa ttcactctca caatcagcag cctgcagcct   240
gaagattttg caacgtatta ctgtctacag cataatagtt acccttacac ttttggccag   300
gggaccaagc tggagatcaa acga                                         324

<210> SEQ ID NO 298
<211> LENGTH: 108
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Glu Lys Pro Gly Lys Ala Pro Lys Arg Leu Ile
         35                  40                  45

Tyr Phe Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Tyr
                 85                  90                  95

Thr Phe Gly Gln Gly Thr Lys Leu Glu Ile Lys Arg
                100                 105

```
<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggcatta gaaatgat                                                     18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Gly Ile Arg Asn Asp
 1               5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 tttgcatcc                                                                9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Phe Ala Ser
 1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
ctacagcata atagttaccc ttacact                                            27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Leu Gln His Asn Ser Tyr Pro Tyr Thr
 1               5

<210> SEQ ID NO 305
<211> LENGTH: 360
<212> TYPE: DNA
<213> ORGANISM: Artificial Sequence
<220> FEATURE:
```

<223> OTHER INFORMATION: Synthetic

<400> SEQUENCE: 305

```
caggtgcagc tggtggagtc tgggggaggc gtggtccagc ctggaggtc cctgagactc      60
tcctgtgtag cgtctggatt caccttcagc agctatggca tgcactgggt ccgccaggct    120
ccaggcaagg ggctggagtg gatggcagtt atttggtatg atggaagtaa taagtacttt    180
gcagactccg tgaaggaccg attcaccatc tccagagaca attccaagaa cacgctgtat    240
ctgcaaatga acactctgag acctgacgac acggctgtgt attactgtgt gaaggcggac    300
gcccccctcc tgatctatgg tgtggacgtc tggggccaag gaccacggt caccgtctcc    360
```

<210> SEQ ID NO 306
<211> LENGTH: 120
<212> TYPE: PRT
<213> ORGANISM: Artificial Sequence
<220> FEATURE:
<223> OTHER INFORMATION: Synthetic

<400> SEQUENCE: 306

```
Gln Val Gln Leu Val Glu Ser Gly Gly Gly Val Val Gln Pro Gly Arg
 1               5                  10                  15
Ser Leu Arg Leu Ser Cys Val Ala Ser Gly Phe Thr Phe Ser Ser Tyr
             20                  25                  30
Gly Met His Trp Val Arg Gln Ala Pro Gly Lys Gly Leu Glu Trp Met
         35                  40                  45
Ala Val Ile Trp Tyr Asp Gly Ser Asn Lys Tyr Phe Ala Asp Ser Val
     50                  55                  60
Lys Asp Arg Phe Thr Ile Ser Arg Asp Asn Ser Lys Asn Thr Leu Tyr
 65                  70                  75                  80
Leu Gln Met Asn Thr Leu Arg Pro Asp Asp Thr Ala Val Tyr Tyr Cys
                 85                  90                  95
Val Lys Ala Asp Ala Pro Leu Leu Ile Tyr Gly Val Asp Val Trp Gly
            100                 105                 110
Gln Gly Thr Thr Val Thr Val Ser
        115                 120
```

<210> SEQ ID NO 307
<211> LENGTH: 321
<212> TYPE: DNA
<213> ORGANISM: Artificial Sequence
<220> FEATURE:
<223> OTHER INFORMATION: Synthetic

<400> SEQUENCE: 307

```
gacatccaga tgacccagtc tccatcctcc ctgtctgcat ctgtaggaga cagagtcacc      60
atcacttgcc gggcaagtca gggcattaga aatgatttag gctggtatca gagaaaacca    120
ggaaaagccc ctaagcgcct gatctatttt gcatccagtt tgcaaagtgg ggtcccatca    180
aggttcagcg gcagtggatc tgggacagaa ttcactctca caatcagcag cctgcagcct    240
gaagattttg caacgtatta ctgtctacag cataatagtt accccttcac ttttggccag    300
gggaccaagc tggagatcaa a                                              321
```

<210> SEQ ID NO 308
<211> LENGTH: 107
<212> TYPE: PRT
<213> ORGANISM: Artificial Sequence
<220> FEATURE:
<223> OTHER INFORMATION: Synthetic -continued

```
<400> SEQUENCE: 308

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Glu Lys Pro Gly Lys Ala Pro Lys Arg Leu Ile
         35                  40                  45

Tyr Phe Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Tyr
                 85                  90                  95

Thr Phe Gly Gln Gly Thr Lys Leu Glu Ile Lys
            100                 105

<210> SEQ ID NO 309
<211> LENGTH: 361
<212> TYPE: DNA
<213> ORGANISM: Artificial Sequence
<220> FEATURE:
<223> OTHER INFORMATION: Synthetic

<400> SEQUENCE: 309
caggtgcagc tggtggagtc tgggggaggc gtggtccagc ctggggaggtc cctgagactc    60 tcctgtgcag cgtctggatt caccttcagc agctatggca tgcactgggt ccgccaggct   120
ccaggcaagg ggctggagtg ggtggcagtt atttggtatg atggaagtaa taagtactat   180
gcagactccg tgaagggccg attcaccatc tccagagaca actccaagaa cacgctgtat   240
ctgcaaatga acagcctgag agccgaggac acggctgtgt attactgtgt gaaggcggac   300 gccccctcc tgatctatgg tgtggacgtc tggggccaag ggaccacggt caccgtctcc   360
t                                                                    361

<210> SEQ ID NO 310
<211> LENGTH: 120
<212> TYPE: PRT
<213> ORGANISM: Artificial Sequence
<220> FEATURE:
<223> OTHER INFORMATION: Synthetic

<400> SEQUENCE: 310

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Lys Ala Asp Ala Pro Leu Leu Ile Tyr Gly Val Asp Val Trp Gly
            100                 105                 110

Gln Gly Thr Thr Val Thr Val Ser
            115                 120
```

<210> SEQ ID NO 311
<211> LENGTH: 322
<212> TYPE: DNA
<213> ORGANISM: Artificial Sequence
<220> FEATURE:
<223> OTHER INFORMATION: Synthetic

<400> SEQUENCE: 311

```
gacatccaga tgacccagtc tccatcctcc ctgtctgcat ctgtaggaga cagagtcacc      60
atcacttgcc gggcaagtca gggcattaga aatgatttag ctggtatca gcagaaacca     120
gggaaagccc ctaagcgcct gatctatttt gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccttacac ttttggccag    300
gggaccaagc tggagatcaa ac                                              322
```

<210> SEQ ID NO 312
<211> LENGTH: 107
<212> TYPE: PRT
<213> ORGANISM: Artificial Sequence
<220> FEATURE:
<223> OTHER INFORMATION: Synthetic

<400> SEQUENCE: 312

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Phe Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105
```

<210> SEQ ID NO 313
<211> LENGTH: 357
<212> TYPE: DNA
<213> ORGANISM: Artificial Sequence
<220> FEATURE:
<223> OTHER INFORMATION: Synthetic

<400> SEQUENCE: 313

```
caggtgcagc tggtggagtc tggggaggc gtggtccagc ctggggaggtc cctgagactc      60
tcctgtgcag cgtctggatt caccttcagg agttatggca tacactgggt ccgccaggct    120
ccaggcaagg gactggagtg gtggcactt atattatatg atggaagtag tgaggactat     180
gcagactccg tgaagggccg attcaccatc tccagagaca attccaagaa tatggtgttt    240
ctgcaaatga acagcctgag agtcgaggac acggctgtct attactgtgc gagagattta    300
ttggcaattg gctggttcga ccgctggggc cagggaaccc tggtcaccgt ctcctca       357
```

<210> SEQ ID NO 314
<211> LENGTH: 119
<212> TYPE: PRT

```
<213> ORGANISM: Artificial Sequence
<220> FEATURE:
<223> OTHER INFORMATION: Synthetic

<400> SEQUENCE: 314

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Arg Ser Tyr
                 20                  25                  30

Gly Ile His Trp Val Arg Gln Ala Pro Gly Lys Gly Leu Glu Trp Val
             35                  40                  45

Ala Leu Ile Leu Tyr Asp Gly Ser Ser Glu Asp Tyr Ala Asp Ser Val
         50                  55                  60

Lys Gly Arg Phe Thr Ile Ser Arg Asp Asn Ser Lys Asn Met Val Phe
 65                  70                  75                  80

Leu Gln Met Asn Ser Leu Arg Val Glu Asp Thr Ala Val Tyr Tyr Cys
                 85                  90                  95

Ala Arg Asp Leu Leu Ala Ile Gly Trp Phe Asp Arg Trp Gly Gln Gly
            100                 105                 110

Thr Leu Val Thr Val Ser Ser
            115

<210> SEQ ID NO 315
<211> LENGTH: 24
<212> TYPE: DNA
<213> ORGANISM: Artificial Sequence
<220> FEATURE:
<223> OTHER INFORMATION: Synthetic

<400> SEQUENCE: 315
ggattcacct tcaggagtta tggc                                          24

<210> SEQ ID NO 316
<211> LENGTH: 8
<212> TYPE: PRT
<213> ORGANISM: Artificial Sequence
<220> FEATURE:
<223> OTHER INFORMATION: Synthetic

<400> SEQUENCE: 316

Gly Phe Thr Phe Arg Ser Tyr Gly
  1               5

<210> SEQ ID NO 317
<211> LENGTH: 24
<212> TYPE: DNA
<213> ORGANISM: Artificial Sequence
<220> FEATURE:
<223> OTHER INFORMATION: Synthetic

<400> SEQUENCE: 317
atattatatg atggaagtag tgag                                          24

<210> SEQ ID NO 318
<211> LENGTH: 8
<212> TYPE: PRT
<213> ORGANISM: Artificial Sequence
<220> FEATURE:
<223> OTHER INFORMATION: Synthetic

<400> SEQUENCE: 318

Ile Leu Tyr Asp Gly Ser Ser Glu
  1               5
```

<210> SEQ ID NO 319
<211> LENGTH: 36
<212> TYPE: DNA
<213> ORGANISM: Artificial Sequence
<220> FEATURE:
<223> OTHER INFORMATION: Synthetic

<400> SEQUENCE: 319
gcgagagatt tattggcaat tggctggttc gaccgc    36

<210> SEQ ID NO 320
<211> LENGTH: 12
<212> TYPE: PRT
<213> ORGANISM: Artificial Sequence
<220> FEATURE:
<223> OTHER INFORMATION: Synthetic

<400> SEQUENCE: 320

Ala Arg Asp Leu Leu Ala Ile Gly Trp Phe Asp Arg
 1               5                  10

<210> SEQ ID NO 321
<211> LENGTH: 324
<212> TYPE: DNA
<213> ORGANISM: Artificial Sequence
<220> FEATURE:
<223> OTHER INFORMATION: Synthetic

<400> SEQUENCE: 321
gaaattgtgt tgacgcagtc tccaggcacc ctgactttgt ctccagggga aagagccacc    60
ctctcctgta gggccagtca gagtcttagt agttataact tagcctggta ccagcagaag   120
cctggccagg ctcccaggct cctcatctat ggtacatcca gcagggccac tggcatccca   180
gacaggttca gtggcagtgg gtctgggaca gacttcactc tcaccatcag cagacttgag   240
cctgaagatt ttacagtgta ttattgtcag caatatggta gctcacctct cactttcggc   300
ggagggacca cggtggagat caaa                                          324

<210> SEQ ID NO 322
<211> LENGTH: 108
<212> TYPE: PRT
<213> ORGANISM: Artificial Sequence
<220> FEATURE:
<223> OTHER INFORMATION: Synthetic

<400> SEQUENCE: 322

Glu Ile Val Leu Thr Gln Ser Pro Gly Thr Leu Thr Leu Ser Pro Gly
 1               5                  10                  15

Glu Arg Ala Thr Leu Ser Cys Arg Ala Ser Gln Ser Leu Ser Ser Tyr
                20                  25                  30

Asn Leu Ala Trp Tyr Gln Gln Lys Pro Gly Gln Ala Pro Arg Leu Leu
            35                  40                  45

Ile Tyr Gly Thr Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Thr Val Tyr Tyr Cys Gln Gln Tyr Gly Ser Ser Pro
                85                  90                  95

Leu Thr Phe Gly Gly Gly Thr Thr Val Glu Ile Lys
            100                 105

<210> SEQ ID NO 323

```
<211> LENGTH: 21
<212> TYPE: DNA
<213> ORGANISM: Artificial Sequence
<220> FEATURE:
<223> OTHER INFORMATION: Synthetic

<400> SEQUENCE: 323
cagagtctta gtagttataa c                                              21

<210> SEQ ID NO 324
<211> LENGTH: 7
<212> TYPE: PRT
<213> ORGANISM: Artificial Sequence
<220> FEATURE:
<223> OTHER INFORMATION: Synthetic

<400> SEQUENCE: 324

Gln Ser Leu Ser Ser Tyr Asn
 1               5

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 ggtacatcc                                                             9

<210> SEQ ID NO 326
<211> LENGTH: 3
<212> TYPE: PRT
<213> ORGANISM: Artificial Sequence
<220> FEATURE:
<223> OTHER INFORMATION: Synthetic

<400> SEQUENCE: 326

Gly Thr Ser
 1

<210> SEQ ID NO 327
<211> LENGTH: 27
<212> TYPE: DNA
<213> ORGANISM: Artificial Sequence
<220> FEATURE:
<223> OTHER INFORMATION: Synthetic

<400> SEQUENCE: 327
cagcaatatg gtagctcacc tctcact                                        27

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Gln Gln Tyr Gly Ser Ser Pro Leu Thr
 1               5

<210> SEQ ID NO 329
<211> LENGTH: 357
<212> TYPE: DNA
<213> ORGANISM: Artificial Sequence
<220> FEATURE:
<223> OTHER INFORMATION: Synthetic
```

<400> SEQUENCE: 329

```
caggtgcagc tggtggagtc tgggggaggc gtggtccagc ctgggaggtc cctgagactc    60
tcctgtgcag cgtctggatt caccttcagg agttatggca tacactgggt ccgccaggct   120
ccaggcaagg gactggagtg gtggcactt atattatatg atggaagtag tgaggactat   180
gcagactccg tgaagggccg attcaccatc tccagagaca attccaagaa tatggtgttt   240
ctgcaaatga acagcctgag agtcgaggac acggctgtct attactgtgc gagagattta   300
ttggcaattg gctggttcga ccgctggggc cagggaaccc tggtcaccgt ctcctca      357
```

<210> SEQ ID NO 330
<211> LENGTH: 119
<212> TYPE: PRT
<213> ORGANISM: Artificial Sequence
<220> FEATURE:
<223> OTHER INFORMATION: Synthetic

<400> SEQUENCE: 330

```
Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Arg Ser Tyr
            20                  25                  30

Gly Ile His Trp Val Arg Gln Ala Pro Gly Lys Gly Leu Glu Trp Val
        35                  40                  45

Ala Leu Ile Leu Tyr Asp Gly Ser Ser Glu Asp Tyr Ala Asp Ser Val
    50                  55                  60

Lys Gly Arg Phe Thr Ile Ser Arg Asp Asn Ser Lys Asn Met Val Phe
65                  70                  75                  80

Leu Gln Met Asn Ser Leu Arg Val Glu Asp Thr Ala Val Tyr Tyr Cys
                85                  90                  95

Ala Arg Asp Leu Leu Ala Ile Gly Trp Phe Asp Arg Trp Gly Gln Gly
            100                 105                 110

Thr Leu Val Thr Val Ser Ser
        115
```

<210> SEQ ID NO 331
<211> LENGTH: 324
<212> TYPE: DNA
<213> ORGANISM: Artificial Sequence
<220> FEATURE:
<223> OTHER INFORMATION: Synthetic

<400> SEQUENCE: 331

```
gaaattgtgt tgacgcagtc tccaggcacc ctgactttgt ctccagggga aagagccacc    60
ctctcctgta gggccagtca gagtcttagt agttataact tagcctggta ccagcagaag   120
cctggccagg ctcccaggct cctcatctat ggtacatcca gcagggccac tggcatccca   180
gacaggttca gtggcagtgg gtctgggaca gacttcactc tcaccatcag cagacttgag   240
cctgaagatt ttacagtgta ttattgtcag caatatggta gctcacctct cactttcggc   300
ggagggacca aggtggagat caaa                                          324
```

<210> SEQ ID NO 332
<211> LENGTH: 108
<212> TYPE: PRT
<213> ORGANISM: Artificial Sequence
<220> FEATURE:
<223> OTHER INFORMATION: Synthetic

<400> SEQUENCE: 332

Glu Ile Val Leu Thr Gln Ser Pro Thr Leu Thr Leu Ser Pro Gly
1               5                   10                  15

Glu Arg Ala Thr Leu Ser Cys Arg Ala Ser Gln Ser Leu Ser Ser Tyr
            20                  25                  30

Asn Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Thr Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 333
<211> LENGTH: 357
<212> TYPE: DNA
<213> ORGANISM: Artificial Sequence
<220> FEATURE:
<223> OTHER INFORMATION: Synthetic

<400> SEQUENCE: 333
caggtgcagc tggtggagtc tgggggaggc gtggtccagc ctggggaggtc cctgagactc      60 tcctgtgcag cctctggatt caccttcagg agttatggca tgcactgggt ccgccaggct     120
ccaggcaagg ggctggagtg ggtggcagtt atattatatg atggaagtag tgagtactat     180
gcagactccg tgaagggccg attcaccatc tccagagaca attccaagaa cacgctgtat     240
ctgcaaatga acagcctgag agctgaggac acggctgtgt attactgtgc gagagattta     300
ttggcaattg gctggttcga ccgctggggc cagggaaccc tggtcaccgt ctcctca       357

<210> SEQ ID NO 334
<211> LENGTH: 119
<212> TYPE: PRT
<213> ORGANISM: Artificial Sequence
<220> FEATURE:
<223> OTHER INFORMATION: Synthetic

<400> SEQUENCE: 334

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Ser Glu Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Ala Ile Gly Trp Phe Asp Arg Trp Gly Gln Gly
            100                 105                 110

Thr Leu Val Thr Val Ser Ser
        115

<210> SEQ ID NO 335

<211> LENGTH: 325
<212> TYPE: DNA
<213> ORGANISM: Artificial Sequence
<220> FEATURE:
<223> OTHER INFORMATION: Synthetic

<400> SEQUENCE: 335

```
gaaattgtgt tgacgcagtc tccaggcacc ctgtctttgt ctccagggga aagagccacc    60
ctctcctgca gggccagtca gagtcttagt agttataact tagcctggta ccagcagaaa   120
cctggccagg ctcccaggct cctcatctat ggtacatcca gcagggccac tggcatccca   180
gacaggttca gtggcagtgg gtctgggaca gacttcactc tcaccatcag cagactggag   240
cctgaagatt ttgcagtgta ttactgtcag caatatggta gctcacctct cactttcggc   300
ggagggacca aggtggagat caaac                                         325
```

<210> SEQ ID NO 336
<211> LENGTH: 108
<212> TYPE: PRT
<213> ORGANISM: Artificial Sequence
<220> FEATURE:
<223> OTHER INFORMATION: Synthetic

<400> SEQUENCE: 336

```
Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Leu Ser Ser Tyr
            20                  25                  30
Asn Leu Ala Trp Tyr Gln Gln Lys Pro Gly Gln Ala Pro Arg Leu Leu
        35                  40                  45
Ile Tyr Gly Thr Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
Pro Glu Asp Phe Ala Val Tyr Tyr Cys Gln Gln Tyr Gly Ser Ser Pro
                85                  90                  95
Leu Thr Phe Gly Gly Gly Thr Lys Val Glu Ile Lys
            100                 105
```

<210> SEQ ID NO 337
<211> LENGTH: 354
<212> TYPE: DNA
<213> ORGANISM: Artificial Sequence
<220> FEATURE:
<223> OTHER INFORMATION: Synthetic

<400> SEQUENCE: 337

```
gaggtgcagc tggtggagtc tgggggaggc ttggtacagc ctggggggtc cctgagactc    60
tcctgtgcag cctctggatt caccttcagt acctacgaca tgaactgggt ccgccaagct   120
acaggaaaag gtctggaatg ggtctcaggt attgatactc tggtgacaca atactatcca   180
gactccgtga agggccgttt caccatctcc agagaaaatg ccaagaactc cttgtatctt   240
caaatgaaca gcctgagagt cggggacacg gctgtgtatt actgtgcaag aggggcgat   300
ttttggagtg gtccagacta ctggggccag ggaaccctgg tcaccgtctc ctca         354
```

<210> SEQ ID NO 338
<211> LENGTH: 118
<212> TYPE: PRT
<213> ORGANISM: Artificial Sequence
<220> FEATURE:
<223> OTHER INFORMATION: Synthetic

<400> SEQUENCE: 338

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Asp Met Asn Trp Val Arg Gln Ala Thr Gly Lys Gly Leu Glu Trp Val
        35                  40                  45

Ser Gly Ile Asp Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Gly Asp Phe Trp Ser Gly Pro Asp Tyr Trp Gly Gln Gly Thr
            100                 105                 110

Leu Val Thr Val Ser Ser
            115

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggattcacct tcagtaccta cgac                                       24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Phe Thr Phe Ser Thr Tyr Asp
1               5

<210> SEQ ID NO 341
<211> LENGTH: 21
<212> TYPE: DNA
<213> ORGANISM: Artificial Sequence
<220> FEATURE:
<223> OTHER INFORMATION: Synthetic

<400> SEQUENCE: 341
attgatactg ctggtgacac a                                          21

<210> SEQ ID NO 342
<211> LENGTH: 7
<212> TYPE: PRT
<213> ORGANISM: Artificial Sequence
<220> FEATURE:
<223> OTHER INFORMATION: Synthetic

<400> SEQUENCE: 342

Ile Asp Thr Ala Gly Asp Thr
1               5

<210> SEQ ID NO 343
<211> LENGTH: 36

<212> TYPE: DNA
<213> ORGANISM: Artificial Sequence
<220> FEATURE:
<223> OTHER INFORMATION: Synthetic

<400> SEQUENCE: 343
gcaagagggg gcgattttg gagtggtcca gactac                                    36

<210> SEQ ID NO 344
<211> LENGTH: 12
<212> TYPE: PRT
<213> ORGANISM: Artificial Sequence
<220> FEATURE:
<223> OTHER INFORMATION: Synthetic

<400> SEQUENCE: 344

Ala Arg Gly Gly Asp Phe Trp Ser Gly Pro Asp Tyr
 1               5                  10

<210> SEQ ID NO 345
<211> LENGTH: 321
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccatcatca ctgtctgcat ctgtcggaga cagagtcacc        60
atcacttgtc gggcgagtca ggacattagc aattatttag cctggtttca gcagaaacca       120
gggaaagccc ctaagtccct gatctatgct gcattcagtt tgcaaagtgg ggtcccatca       180
aagttcagcg gcagtgtatc tgggacagat ttcactctca ccatcagcag cctgcagcct       240
gaagattttg caacttatta ttgccaacag tatattactt acccattcac tttcggccct       300
gggaccaaag tggatatcaa a                                                 321

<210> SEQ ID NO 346
<211> LENGTH: 107
<212> TYPE: PRT
<213> ORGANISM: Artificial Sequence
<220> FEATURE:
<223> OTHER INFORMATION: Synthetic

<400> SEQUENCE: 346

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Phe Ser Leu Gln Ser Gly Val Pro Ser Lys Phe Ser Gly
    50                  55                  60

Ser Val Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Thr Tyr Pro Phe
                85                  90                  95

Thr Phe Gly Pro Gly Thr Lys Val Asp Ile Lys
            100                 105

<210> SEQ ID NO 347
<211> LENGTH: 18
<212> TYPE: DNA
<213> ORGANISM: Artificial Sequence

```
<220> FEATURE:
<223> OTHER INFORMATION: Synthetic

<400> SEQUENCE: 347
caggacatta gcaattat                                                    18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348

Gln Asp Ile Ser Asn Tyr
 1               5

<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 gctgcattc                                                               9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350

Ala Ala Phe
 1

<210> SEQ ID NO 351
<211> LENGTH: 27
<212> TYPE: DNA
<213> ORGANISM: Artificial Sequence
<220> FEATURE:
<223> OTHER INFORMATION: Synthetic

<400> SEQUENCE: 351
caacagtata ttacttaccc attcact                                           27

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Tyr Ile Thr Tyr Pro Phe Thr
 1               5

<210> SEQ ID NO 353
<211> LENGTH: 354
<212> TYPE: DNA
<213> ORGANISM: Artificial Sequence
<220> FEATURE:
<223> OTHER INFORMATION: Synthetic

<400> SEQUENCE: 353
```

```
gaggtgcagc tggtggagtc tgggggaggc ttggtacagc ctgggggtc cctgagactc      60 tcctgtgcag cctctggatt caccttcagt acctacgaca tgaactgggt ccgccaagct    120
acaggaaaag gtctggaatg ggtctcaggt attgatactg ctggtgacac atactatcca    180
gactccgtga agggccgttt caccatctcc agagaaaatg ccaagaactc cttgtatctt    240
caaatgaaca gcctgagagt cggggacacg gctgtgtatt actgtgcaag agggggcgat    300
ttttggagtg gtccagacta ctggggccag ggaaccctgg tcaccgtctc ctca          354
```

<210> SEQ ID NO 354
<211> LENGTH: 118
<212> TYPE: PRT
<213> ORGANISM: Artificial Sequence
<220> FEATURE:
<223> OTHER INFORMATION: Synthetic

<400> SEQUENCE: 354

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Asp Met Asn Trp Val Arg Gln Ala Thr Gly Lys Gly Leu Glu Trp Val
        35                  40                  45

Ser Gly Ile Asp Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Ala
                85                  90                  95

Arg Gly Gly Asp Phe Trp Ser Gly Pro Asp Tyr Trp Gly Gln Gly Thr
            100                 105                 110

Leu Val Thr Val Ser Ser
        115
```

<210> SEQ ID NO 355
<211> LENGTH: 321
<212> TYPE: DNA
<213> ORGANISM: Artificial Sequence
<220> FEATURE:
<223> OTHER INFORMATION: Synthetic

<400> SEQUENCE: 355

```
gacatccaga tgacccagtc tccatcatca ctgtctgcat ctgtcggaga cagagtcacc     60
atcacttgtc gggcgagtca ggacattagc aattatttag cctggtttca gcagaaacca    120
gggaaagccc ctaagtccct gatctatgct gcattcagtt tgcaaagtgg ggtcccatca    180 agttcagcg gcagtgtatc tgggacagat ttcactctca ccatcagcag cctgcagcct    240
gaagattttg caactattat tgccaacag tatattactt acccattcac tttcggccct    300
gggaccaaag tggatatcaa a                                              321
```

<210> SEQ ID NO 356
<211> LENGTH: 107
<212> TYPE: PRT
<213> ORGANISM: Artificial Sequence
<220> FEATURE:
<223> OTHER INFORMATION: Synthetic

<400> SEQUENCE: 356

```
Asp Ile Gln Met Thr Gln Ser Pro Ser Ser Leu Ser Ala Ser Val Gly
 1               5                  10                  15
```

Asp Arg Val Thr Ile Thr Cys Arg Ala Ser Gln Asp Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Phe Ser Leu Gln Ser Gly Val Pro Ser Lys Phe Ser Gly
 50                  55                  60

Ser Val Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ile Thr Tyr Pro Phe
                85                  90                  95

Thr Phe Gly Pro Gly Thr Lys Val Asp Ile Lys
            100                 105

<210> SEQ ID NO 357
<211> LENGTH: 354
<212> TYPE: DNA
<213> ORGANISM: Artificial Sequence
<220> FEATURE:
<223> OTHER INFORMATION: Synthetic

<400> SEQUENCE: 357
gaggtgcagc tggtggagtc tgggggaggc ttggtacagc ctggggggtc cctgagactc      60
tcctgtgcag cctctggatt caccttcagt acctacgaca tgcactgggt ccgccaagct     120
acaggaaaag gtctggagtg ggtctcagct attgatactg ctggtgacac atactatcca     180
ggctccgtga aggccgatt caccatctcc agagaaaatg ccaagaactc cttgtatctt     240
caaatgaaca gcctgagagc cggggacacg gctgtgtatt actgtgcaag agggggcgat     300
ttttggagtg gtccagacta ctggggccag ggaaccctgg tcaccgtctc ctca           354

<210> SEQ ID NO 358
<211> LENGTH: 118
<212> TYPE: PRT
<213> ORGANISM: Artificial Sequence
<220> FEATURE:
<223> OTHER INFORMATION: Synthetic

<400> SEQUENCE: 358

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Asp Met His Trp Val Arg Gln Ala Thr Gly Lys Gly Leu Glu Trp Val
        35                  40                  45

Ser Ala Ile Asp Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
 65                  70                  75                  80

Gln Met Asn Ser Leu Arg Ala Gly Asp Thr Ala Val Tyr Tyr Cys Ala
                85                  90                  95

Arg Gly Gly Asp Phe Trp Ser Gly Pro Asp Tyr Trp Gly Gln Gly Thr
            100                 105                 110

Leu Val Thr Val Ser Ser
        115

<210> SEQ ID NO 359
<211> LENGTH: 322
<212> TYPE: DNA
<213> ORGANISM: Artificial Sequence

```
<220> FEATURE:
<223> OTHER INFORMATION: Synthetic

<400> SEQUENCE: 359
gacatccaga tgacccagtc tccatcctca ctgtctgcat ctgtaggaga cagagtcacc      60
atcacttgtc gggcgagtca ggacattagc aattatttag cctggtttca gcagaaacca     120
gggaaagccc ctaagtccct gatctatgct gcattcagtt tgcaaagtgg ggtcccatca     180
aggttcagcg gcagtggatc tgggacagat ttcactctca ccatcagcag cctgcagcct     240
gaagattttg caacttatta ctgccaacag tatattactt acccattcac tttcggccct     300
gggaccaaag tggatatcaa ac                                              322

<210> SEQ ID NO 360
<211> LENGTH: 107
<212> TYPE: PRT
<213> ORGANISM: Artificial Sequence
<220> FEATURE:
<223> OTHER INFORMATION: Synthetic

<400> SEQUENCE: 360

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
                 20                  25                  30

Leu Ala Trp Phe Gln Gln Lys Pro Gly Lys Ala Pro Lys Ser Leu Ile
             35                  40                  45

Tyr Ala Ala Phe Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ile Thr Tyr Pro Phe
                 85                  90                  95

Thr Phe Gly Pro Gly Thr Lys Val Asp Ile Lys
            100                 105

<210> SEQ ID NO 361
<211> LENGTH: 363
<212> TYPE: DNA
<213> ORGANISM: Artificial Sequence
<220> FEATURE:
<223> OTHER INFORMATION: Synthetic

<400> SEQUENCE: 361
gaagtggaac tggtggagtc tgggggaggc ttggtacagc ctggcaggtc cctgagactc      60
tcctgtgcag cctctggatt caccttttgat gattatgcca tgcactgggt ccggcaagct    120
ccagggaagg gcctggagtg ggtctcaggt attagttgga atagtggtag catagaatat     180
gcggactctg tgaagggccg attcaccatc tccagagaca cgccaagaa ctccctgtat      240 ctgcaaatga acagtctgag agctgaggac acggccttgt attactgtgc aaaagatcac     300
tgggactacg actttgaata cttccaccac tggggccagg gcaccctggt caccgtctcc     360
tca                                                                   363

<210> SEQ ID NO 362
<211> LENGTH: 121
<212> TYPE: PRT
<213> ORGANISM: Artificial Sequence
<220> FEATURE:
<223> OTHER INFORMATION: Synthetic
```

<400> SEQUENCE: 362

Glu Val Glu Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp His Trp Asp Tyr Asp Phe Glu Tyr Phe His His Trp Gly
            100                 105                 110

Gln Gly Thr Leu Val Thr Val Ser Ser
        115                 120

<210> SEQ ID NO 363
<211> LENGTH: 24
<212> TYPE: DNA
<213> ORGANISM: Artificial Sequence
<220> FEATURE:
<223> OTHER INFORMATION: Synthetic

<400> SEQUENCE: 363
ggattcacct ttgatgatta tgcc                                          24

<210> SEQ ID NO 364
<211> LENGTH: 8
<212> TYPE: PRT
<213> ORGANISM: Artificial Sequence
<220> FEATURE:
<223> OTHER INFORMATION: Synthetic

<400> SEQUENCE: 364

Gly Phe Thr Phe Asp Asp Tyr Ala
1               5

<210> SEQ ID NO 365
<211> LENGTH: 24
<212> TYPE: DNA
<213> ORGANISM: Artificial Sequence
<220> FEATURE:
<223> OTHER INFORMATION: Synthetic

<400> SEQUENCE: 365
attagttgga atagtggtag cata                                          24

<210> SEQ ID NO 366
<211> LENGTH: 8
<212> TYPE: PRT
<213> ORGANISM: Artificial Sequence
<220> FEATURE:
<223> OTHER INFORMATION: Synthetic

<400> SEQUENCE: 366

Ile Ser Trp Asn Ser Gly Ser Ile
1               5

<210> SEQ ID NO 367
<211> LENGTH: 42
<212> TYPE: DNA

```
<213> ORGANISM: Artificial Sequence
<220> FEATURE:
<223> OTHER INFORMATION: Synthetic

<400> SEQUENCE: 367
gcaaaagatc actgggacta cgactttgaa tacttccacc ac                         42

<210> SEQ ID NO 368
<211> LENGTH: 14
<212> TYPE: PRT
<213> ORGANISM: Artificial Sequence
<220> FEATURE:
<223> OTHER INFORMATION: Synthetic

<400> SEQUENCE: 368

Ala Lys Asp His Trp Asp Tyr Asp Phe Glu Tyr Phe His His
 1               5                  10

<210> SEQ ID NO 369
<211> LENGTH: 318
<212> TYPE: DNA
<213> ORGANISM: Artificial Sequence
<220> FEATURE:
<223> OTHER INFORMATION: Synthetic

<400> SEQUENCE: 369
gacatccaga tgacccagtc tccttccacc ctgtctgcat ctgtaggaga cagagtcacc       60
atcacttgcc gggccagtca gagtattagt agctggttgg cctggtatca gcagaaacca      120
gggaaggccc ctaacctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tataatagtt attacacttt tggccagggg      300
accaagctgg agatcaaa                                                    318

<210> SEQ ID NO 370
<211> LENGTH: 106
<212> TYPE: PRT
<213> ORGANISM: Artificial Sequence
<220> FEATURE:
<223> OTHER INFORMATION: Synthetic

<400> SEQUENCE: 370

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105

<210> SEQ ID NO 371
<211> LENGTH: 18
<212> TYPE: DNA
<213> ORGANISM: Artificial Sequence
<220> FEATURE:
```

```
<223> OTHER INFORMATION: Synthetic

<400> SEQUENCE: 371
cagagtatta gtagctgg                                                   18

<210> SEQ ID NO 372
<211> LENGTH: 6
<212> TYPE: PRT
<213> ORGANISM: Artificial Sequence
<220> FEATURE:
<223> OTHER INFORMATION: Synthetic

<400> SEQUENCE: 372

Gln Ser Ile Ser Ser Trp
 1               5

<210> SEQ ID NO 373
<211> LENGTH: 9
<212> TYPE: DNA
<213> ORGANISM: Artificial Sequence
<220> FEATURE:
<223> OTHER INFORMATION: Synthetic

<400> SEQUENCE: 373 aaggcgtct                                                              9

<210> SEQ ID NO 374
<211> LENGTH: 3
<212> TYPE: PRT
<213> ORGANISM: Artificial Sequence
<220> FEATURE:
<223> OTHER INFORMATION: Synthetic

<400> SEQUENCE: 374

Lys Ala Ser
 1

<210> SEQ ID NO 375
<211> LENGTH: 24
<212> TYPE: DNA
<213> ORGANISM: Artificial Sequence
<220> FEATURE:
<223> OTHER INFORMATION: Synthetic

<400> SEQUENCE: 375
caacagtata atagttatta cact                                            24

<210> SEQ ID NO 376
<211> LENGTH: 8
<212> TYPE: PRT
<213> ORGANISM: Artificial Sequence
<220> FEATURE:
<223> OTHER INFORMATION: Synthetic

<400> SEQUENCE: 376

Gln Gln Tyr Asn Ser Tyr Tyr Thr
 1               5

<210> SEQ ID NO 377
<211> LENGTH: 363
<212> TYPE: DNA
<213> ORGANISM: Artificial Sequence
<220> FEATURE:
<223> OTHER INFORMATION: Synthetic

<400> SEQUENCE: 377
gaagtgcagc tggtggagtc tgggggaggc ttggtacagc ctggcaggtc cctgagactc     60
```

```
tcctgtgcag cctctggatt caccttTgat gattatgcca tgcactgggt ccggcaagct    120
ccagggaagg gcctggagtg ggtctcaggt attagttgga atagtggtag catagaatat    180
gcggactctg tgaagggccg attcaccatc tccagagaca acgccaagaa ctccctgtat    240
ctgcaaatga acagtctgag agctgaggac acggccttgt attactgtgc aaaagatcac    300
tgggactacg actttgaata cttccaccac tggggccagg caccctggt caccgtctcc    360 tca                                                                  363
```

<210> SEQ ID NO 378
<211> LENGTH: 121
<212> TYPE: PRT
<213> ORGANISM: Artificial Sequence
<220> FEATURE:
<223> OTHER INFORMATION: Synthetic

<400> SEQUENCE: 378

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Glu Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp His Trp Asp Tyr Asp Phe Glu Tyr Phe His His Trp Gly
            100                 105                 110

Gln Gly Thr Leu Val Thr Val Ser Ser
        115                 120
```

<210> SEQ ID NO 379
<211> LENGTH: 318
<212> TYPE: DNA
<213> ORGANISM: Artificial Sequence
<220> FEATURE:
<223> OTHER INFORMATION: Synthetic

<400> SEQUENCE: 379

```
gacatccaga tgacccagtc tccttccacc ctgtctgcat ctgtaggaga cagagtcacc     60
atcacttgcc gggccagtca gagtattagt agctggttgg cctggtatca gcagaaacca    120
gggaaggccc ctaacctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attacacttt tggccagggg    300
accaagctgg agatcaaa                                                  318
```

<210> SEQ ID NO 380
<211> LENGTH: 106
<212> TYPE: PRT
<213> ORGANISM: Artificial Sequence
<220> FEATURE:
<223> OTHER INFORMATION: Synthetic

<400> SEQUENCE: 380

```
Asp Ile Gln Met Thr Gln Ser Pro Ser Thr Leu Ser Ala Ser Val Gly
  1               5                  10                  15
```

```
                1               5                  10                 15
Asp Arg Val Thr Ile Thr Cys Arg Ala Ser Gln Ser Ile Ser Ser Trp
                    20                  25                  30

Leu Ala Trp Tyr Gln Gln Lys Pro Gly Lys Ala Pro Asn Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Tyr Thr
                85                  90                  95

Phe Gly Gln Gly Thr Lys Leu Glu Ile Lys
            100                 105

<210> SEQ ID NO 381
<211> LENGTH: 363
<212> TYPE: DNA
<213> ORGANISM: Artificial Sequence
<220> FEATURE:
<223> OTHER INFORMATION: Synthetic

<400> SEQUENCE: 381
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg gtctcaggt attagttgga atagtggtag catagggctat  180 gcggactctg tgaagggccg attcaccatc tccagagaca cgccaagaa ctccctgtat    240 ctgcaaatga acagtctgag agctgaggac acggccttgt attactgtgc aaaagatcac   300
tgggactacg actttgaata cttccaccac tggggccagg gcaccctggt caccgtctcc   360
tca                                                                  363

<210> SEQ ID NO 382
<211> LENGTH: 121
<212> TYPE: PRT
<213> ORGANISM: Artificial Sequence
<220> FEATURE:
<223> OTHER INFORMATION: Synthetic

<400> SEQUENCE: 382

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp His Trp Asp Tyr Asp Phe Glu Tyr Phe His His Trp Gly
            100                 105                 110

Gln Gly Thr Leu Val Thr Val Ser Ser
        115                 120

<210> SEQ ID NO 383
```

<211> LENGTH: 319
<212> TYPE: DNA
<213> ORGANISM: Artificial Sequence
<220> FEATURE:
<223> OTHER INFORMATION: Synthetic

<400> SEQUENCE: 383

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tataatagtt attacacttt tggccagggg   300
accaagctgg agatcaaac                                                319
```

<210> SEQ ID NO 384
<211> LENGTH: 106
<212> TYPE: PRT
<213> ORGANISM: Artificial Sequence
<220> FEATURE:
<223> OTHER INFORMATION: Synthetic

<400> SEQUENCE: 384

```
Asp Ile Gln Met Thr Gln Ser Pro Ser Thr Leu Ser Ala Ser Val Gly
 1               5                  10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Leu Leu Ile
        35                  40                  45
Tyr Lys Ala Ser Ser Leu Glu Ser Gly Val Pro Ser Arg Phe Ser Gly
 50                  55                  60
Ser Gly Ser Gly Thr Glu Phe Thr Leu Thr Ile Ser Ser Leu Gln Pro
 65                  70                  75                  80
Asp Asp Phe Ala Thr Tyr Tyr Cys Gln Gln Tyr Asn Ser Tyr Tyr Thr
                85                  90                  95
Phe Gly Gln Gly Thr Lys Leu Glu Ile Lys
            100                 105
```

<210> SEQ ID NO 385
<211> LENGTH: 363
<212> TYPE: DNA
<213> ORGANISM: Artificial Sequence
<220> FEATURE:
<223> OTHER INFORMATION: Synthetic

<400> SEQUENCE: 385

```
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtag catagtctat   180
gcggactctg tgaagggccg attcaccatc tccagagaca acgccaagaa ctccctgtat   240
ctgcaaatga acagtctaat atctgaggac acggccttgt attactgtgc aaaagatgaa   300
aacagctcgt cggggaactg gttcgacccc tggggccagg gaaccctggt caccgtctcc   360
tca                                                                 363
```

<210> SEQ ID NO 386
<211> LENGTH: 121
<212> TYPE: PRT
<213> ORGANISM: Artificial Sequence

```
<220> FEATURE:
<223> OTHER INFORMATION: Synthetic

<400> SEQUENCE: 386

Glu Val Gln Leu Val Glu Ser Gly Gly Leu Val Gln Pro Gly Arg
 1               5                  10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
             35                  40                  45

Ser Gly Ile Ser Trp Asn Ser Gly Ser Ile Val Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Ile Ser Glu Asp Thr Ala Leu Tyr Tyr Cys
                 85                  90                  95

Ala Lys Asp Glu Asn Ser Ser Ser Gly Asn Trp Phe Asp Pro Trp Gly
            100                 105                 110

Gln Gly Thr Leu Val Thr Val Ser Ser
        115                 120

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct ttgatgatta tgcc                                          24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Asp Asp Tyr Ala
 1               5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attagttgga atagtggtag cata                                          24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Ser Trp Asn Ser Gly Ser Ile
 1               5
```

<210> SEQ ID NO 391
<211> LENGTH: 42
<212> TYPE: DNA
<213> ORGANISM: Artificial Sequence
<220> FEATURE:
<223> OTHER INFORMATION: Synthetic

<400> SEQUENCE: 391
gcaaaagatg aaaacagctc gtcggggaac tggttcgacc cc    42

<210> SEQ ID NO 392
<211> LENGTH: 14
<212> TYPE: PRT
<213> ORGANISM: Artificial Sequence
<220> FEATURE:
<223> OTHER INFORMATION: Synthetic

<400> SEQUENCE: 392

Ala Lys Asp Glu Asn Ser Ser Gly Asn Trp Phe Asp Pro
 1               5                  10

<210> SEQ ID NO 393
<211> LENGTH: 318
<212> TYPE: DNA
<213> ORGANISM: Artificial Sequence
<220> FEATURE:
<223> OTHER INFORMATION: Synthetic

<400> SEQUENCE: 393
gaagtagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcaggaa tataataatt ggatcacctt cggccaaggg   300
acacgactgg agattaaa                                                 318

<210> SEQ ID NO 394
<211> LENGTH: 106
<212> TYPE: PRT
<213> ORGANISM: Artificial Sequence
<220> FEATURE:
<223> OTHER INFORMATION: Synthetic

<400> SEQUENCE: 394

Glu Val Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Glu Tyr Asn Asn Trp Ile Thr
                 85                  90                  95

Phe Gly Gln Gly Thr Arg Leu Glu Ile Lys
            100                 105

<210> SEQ ID NO 395
<211> LENGTH: 18

```
<212> TYPE: DNA
<213> ORGANISM: Artificial Sequence
<220> FEATURE:
<223> OTHER INFORMATION: Synthetic

<400> SEQUENCE: 395
cagagtgtta gcagcaac                                                   18

<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396

Gln Ser Val Ser Ser Asn
 1               5

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 ggtgcatcc                                                              9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

Gly Ala Ser
 1

<210> SEQ ID NO 399
<211> LENGTH: 24
<212> TYPE: DNA
<213> ORGANISM: Artificial Sequence
<220> FEATURE:
<223> OTHER INFORMATION: Synthetic

<400> SEQUENCE: 399
caggaatata ataattggat cacc                                            24

<210> SEQ ID NO 400
<211> LENGTH: 8
<212> TYPE: PRT
<213> ORGANISM: Artificial Sequence
<220> FEATURE:
<223> OTHER INFORMATION: Synthetic

<400> SEQUENCE: 400

Gln Glu Tyr Asn Asn Trp Ile Thr
 1               5

<210> SEQ ID NO 401
<211> LENGTH: 363
<212> TYPE: DNA
<213> ORGANISM: Artificial Sequence
<220> FEATURE:
<223> OTHER INFORMATION: Synthetic
```

<400> SEQUENCE: 401

```
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg gtctcaggt attagttgga atagtggtag catagtctat   180
gcggactctg tgaagggccg attcaccatc tccagagaca acgccaagaa ctccctgtat   240
ctgcaaatga acagtctaat atctgaggac acggccttgt attactgtgc aaaagatgaa   300
aacagctcgt cggggaactg gttcgacccc tggggccagg gaaccctggt caccgtctcc   360
tca                                                                  363
```

<210> SEQ ID NO 402
<211> LENGTH: 121
<212> TYPE: PRT
<213> ORGANISM: Artificial Sequence
<220> FEATURE:
<223> OTHER INFORMATION: Synthetic

<400> SEQUENCE: 402

```
Glu Val Gln Leu Val Glu Ser Gly Gly Gly Leu Val Gln Pro Gly Arg
 1               5                  10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
Ser Gly Ile Ser Trp Asn Ser Gly Ser Ile Val Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Ile Ser Glu Asp Thr Ala Leu Tyr Tyr Cys
                85                  90                  95
Ala Lys Asp Glu Asn Ser Ser Ser Gly Asn Trp Phe Asp Pro Trp Gly
            100                 105                 110
Gln Gly Thr Leu Val Thr Val Ser Ser
        115                 120
```

<210> SEQ ID NO 403
<211> LENGTH: 318
<212> TYPE: DNA
<213> ORGANISM: Artificial Sequence
<220> FEATURE:
<223> OTHER INFORMATION: Synthetic

<400> SEQUENCE: 403

```
gaaatagtga tgacgcagtc tccagccacc ctgtctgtgt ctccagggga aagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcaggaa tataataatt ggatcacctt cggccaaggg   300
acacgactgg agattaaa                                                  318
```

<210> SEQ ID NO 404
<211> LENGTH: 106
<212> TYPE: PRT
<213> ORGANISM: Artificial Sequence
<220> FEATURE:
<223> OTHER INFORMATION: Synthetic

<400> SEQUENCE: 404

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Glu Tyr Asn Asn Trp Ile Thr
                85                  90                  95

Phe Gly Gln Gly Thr Arg Leu Glu Ile Lys
            100                 105

<210> SEQ ID NO 405
<211> LENGTH: 363
<212> TYPE: DNA
<213> ORGANISM: Artificial Sequence
<220> FEATURE:
<223> OTHER INFORMATION: Synthetic

<400> SEQUENCE: 405
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca cgccaagaa ctccctgtat      240 ctgcaaatga acagtctgag agctgaggac acggccttgt attactgtgc aaaagatgaa     300
aacagctcgt cggggaactg gttcgacccc tggggccagg gaaccctggt caccgtctcc     360
tca                                                                    363

<210> SEQ ID NO 406
<211> LENGTH: 121
<212> TYPE: PRT
<213> ORGANISM: Artificial Sequence
<220> FEATURE:
<223> OTHER INFORMATION: Synthetic

<400> SEQUENCE: 406

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Glu Asn Ser Ser Ser Gly Asn Trp Phe Asp Pro Trp Gly
            100                 105                 110

Gln Gly Thr Leu Val Thr Val Ser Ser
        115                 120

<210> SEQ ID NO 407
<211> LENGTH: 319
<212> TYPE: DNA
<213> ORGANISM: Artificial Sequence
<220> FEATURE:
<223> OTHER INFORMATION: Synthetic

<400> SEQUENCE: 407

```
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcaggaa tataataatt ggatcacctt cggccaaggg     300
acacgactgg agattaaac                                                  319
```

<210> SEQ ID NO 408
<211> LENGTH: 106
<212> TYPE: PRT
<213> ORGANISM: Artificial Sequence
<220> FEATURE:
<223> OTHER INFORMATION: Synthetic

<400> SEQUENCE: 408

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Glu Tyr Asn Asn Trp Ile Thr
                85                  90                  95

Phe Gly Gln Gly Thr Arg Leu Glu Ile Lys
            100                 105

<210> SEQ ID NO 409
<211> LENGTH: 366
<212> TYPE: DNA
<213> ORGANISM: Artificial Sequence
<220> FEATURE:
<223> OTHER INFORMATION: Synthetic

<400> SEQUENCE: 409

```
gaggtgcagc tggtggagtc tgggggaggc ttggtaaagc ctggggggtc ccttagactc      60
tcctgtgcag cctctggatt cactttcagt aacgcctgga tgagctgggt ccgccaggct     120
ccagggaagg ggctggagtg ggttggccat attcaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtacaaca     300
gcagattacg attttggag tggggttgac tactggggcc agggaaccct ggtcaccgtc     360
tcttca                                                                366
```

<210> SEQ ID NO 410

```
<211> LENGTH: 122
<212> TYPE: PRT
<213> ORGANISM: Artificial Sequence
<220> FEATURE:
<223> OTHER INFORMATION: Synthetic

<400> SEQUENCE: 410

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly His Ile Gln Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ala Asp Tyr Asp Phe Trp Ser Gly Val Asp Tyr Trp
            100                 105                 110

Gly Gln Gly Thr Leu Val Thr Val Ser Ser
        115                 120

<210> SEQ ID NO 411
<211> LENGTH: 24
<212> TYPE: DNA
<213> ORGANISM: Artificial Sequence
<220> FEATURE:
<223> OTHER INFORMATION: Synthetic

<400> SEQUENCE: 411
ggattcactt tcagtaacgc ctgg                                          24

<210> SEQ ID NO 412
<211> LENGTH: 8
<212> TYPE: PRT
<213> ORGANISM: Artificial Sequence
<220> FEATURE:
<223> OTHER INFORMATION: Synthetic

<400> SEQUENCE: 412

Gly Phe Thr Phe Ser Asn Ala Trp
 1               5

<210> SEQ ID NO 413
<211> LENGTH: 30
<212> TYPE: DNA
<213> ORGANISM: Artificial Sequence
<220> FEATURE:
<223> OTHER INFORMATION: Synthetic

<400> SEQUENCE: 413
attcaaagca aaactgatgg tgggacaaca                                    30

<210> SEQ ID NO 414
<211> LENGTH: 10
<212> TYPE: PRT
<213> ORGANISM: Artificial Sequence
<220> FEATURE:
<223> OTHER INFORMATION: Synthetic

<400> SEQUENCE: 414

Ile Gln Ser Lys Thr Asp Gly Gly Thr Thr
 1               5                  10
```

<210> SEQ ID NO 415
<211> LENGTH: 39
<212> TYPE: DNA
<213> ORGANISM: Artificial Sequence
<220> FEATURE:
<223> OTHER INFORMATION: Synthetic

<400> SEQUENCE: 415
acaacagcag attacgattt ttggagtggg gttgactac                                    39

<210> SEQ ID NO 416
<211> LENGTH: 13
<212> TYPE: PRT
<213> ORGANISM: Artificial Sequence
<220> FEATURE:
<223> OTHER INFORMATION: Synthetic

<400> SEQUENCE: 416

Thr Thr Ala Asp Tyr Asp Phe Trp Ser Gly Val Asp Tyr
 1               5                  10

<210> SEQ ID NO 417
<211> LENGTH: 321
<212> TYPE: DNA
<213> ORGANISM: Artificial Sequence
<220> FEATURE:
<223> OTHER INFORMATION: Synthetic

<400> SEQUENCE: 417
gacatccaga tgacccagtc tccatcttcc gtgtctgcat ctgtaggaga cagagtcacc            60
atcacttgtc gggcgagtca gggtattagc agctggttag tctggtatca gcagaaacca          120
gggaaggccc ctaagctcct gatttatgct gcatccagtt tacaaagtgg ggtcccatca          180
agattcagcg gcagtggatc tgggacagat ttcactctca ccatcagcag cctgcagcct          240
gaagattttg caacttacta ttgtcaacag gctaacagtt tcccattcac tttcggccct          300
gggaccaaag tggatgtcaa a                                                    321

<210> SEQ ID NO 418
<211> LENGTH: 107
<212> TYPE: PRT
<213> ORGANISM: Artificial Sequence
<220> FEATURE:
<223> OTHER INFORMATION: Synthetic

<400> SEQUENCE: 418

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Val Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Val Lys
            100                 105

```
<210> SEQ ID NO 419
<211> LENGTH: 18
<212> TYPE: DNA
<213> ORGANISM: Artificial Sequence
<220> FEATURE:
<223> OTHER INFORMATION: Synthetic

<400> SEQUENCE: 419
cagggtatta gcagctgg                                                 18

<210> SEQ ID NO 420
<211> LENGTH: 6
<212> TYPE: PRT
<213> ORGANISM: Artificial Sequence
<220> FEATURE:
<223> OTHER INFORMATION: Synthetic

<400> SEQUENCE: 420

Gln Gly Ile Ser Ser Trp
 1               5

<210> SEQ ID NO 421
<211> LENGTH: 9
<212> TYPE: DNA
<213> ORGANISM: Artificial Sequence
<220> FEATURE:
<223> OTHER INFORMATION: Synthetic

<400> SEQUENCE: 421 gctgcatcc                                                            9

<210> SEQ ID NO 422
<211> LENGTH: 3
<212> TYPE: PRT
<213> ORGANISM: Artificial Sequence
<220> FEATURE:
<223> OTHER INFORMATION: Synthetic

<400> SEQUENCE: 422

Ala Ala Ser
 1

<210> SEQ ID NO 423
<211> LENGTH: 27
<212> TYPE: DNA
<213> ORGANISM: Artificial Sequence
<220> FEATURE:
<223> OTHER INFORMATION: Synthetic

<400> SEQUENCE: 423
caacaggcta acagtttccc attcact                                       27

<210> SEQ ID NO 424
<211> LENGTH: 9
<212> TYPE: PRT
<213> ORGANISM: Artificial Sequence
<220> FEATURE:
<223> OTHER INFORMATION: Synthetic

<400> SEQUENCE: 424

Gln Gln Ala Asn Ser Phe Pro Phe Thr
 1               5

<210> SEQ ID NO 425
<211> LENGTH: 366
<212> TYPE: DNA
<213> ORGANISM: Artificial Sequence
```

```
<220> FEATURE:
<223> OTHER INFORMATION: Synthetic

<400> SEQUENCE: 425
gaggtgcagc tggtggagtc tgggggaggc ttggtaaagc ctgggggtc ccttagactc    60 tcctgtgcag cctctggatt cactttcagt aacgcctgga tgagctgggt ccgccaggct   120
ccagggaagg ggctggagtg ggttggccat attcaaagca aaactgatgg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtacaaca   300
gcagattacg attttggag tggggttgac tactggggcc agggaaccct ggtcaccgtc   360
tcctca                                                              366

<210> SEQ ID NO 426
<211> LENGTH: 122
<212> TYPE: PRT
<213> ORGANISM: Artificial Sequence
<220> FEATURE:
<223> OTHER INFORMATION: Synthetic

<400> SEQUENCE: 426

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly His Ile Gln Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ala Asp Tyr Asp Phe Trp Ser Gly Val Asp Tyr Trp
            100                 105                 110

Gly Gln Gly Thr Leu Val Thr Val Ser Ser
        115                 120

<210> SEQ ID NO 427
<211> LENGTH: 321
<212> TYPE: DNA
<213> ORGANISM: Artificial Sequence
<220> FEATURE:
<223> OTHER INFORMATION: Synthetic

<400> SEQUENCE: 427
gacatccaga tgacccagtc tccatcttcc gtgtctgcat ctgtaggaga cagagtcacc    60
atcacttgtc gggcgagtca gggtattagc agctggttag tctggtatca gcagaaacca   120
gggaaggccc ctaagctcct gatttatgct gcatccagtt tacaaagtgg ggtcccatca   180
agattcagcg gcagtggatc tgggacagat ttcactctca ccatcagcag cctgcagcct   240
gaagattttg caacttacta ttgtcaacag gctaacagtt tcccattcac tttcggccct   300
gggaccaaag tggatatcaa a                                             321

<210> SEQ ID NO 428
<211> LENGTH: 107
<212> TYPE: PRT
<213> ORGANISM: Artificial Sequence
```

<220> FEATURE:
<223> OTHER INFORMATION: Synthetic

<400> SEQUENCE: 428

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 429
<211> LENGTH: 366
<212> TYPE: DNA
<213> ORGANISM: Artificial Sequence
<220> FEATURE:
<223> OTHER INFORMATION: Synthetic

<400> SEQUENCE: 429
gaggtgcagc tggtggagtc tgggggaggc ttggtaaagc ctggggggtc ccttagactc      60
tcctgtgcag cctctggatt cactttcagt aacgcctgga tgagctgggt ccgccaggct     120
ccagggaagg ggctggagtg ggttggccgt attcaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtacaaca     300
gcagattacg atttttggag tggggttgac tactggggcc agggaaccct ggtcaccgtc     360
tcctca                                                                366

<210> SEQ ID NO 430
<211> LENGTH: 122
<212> TYPE: PRT
<213> ORGANISM: Artificial Sequence
<220> FEATURE:
<223> OTHER INFORMATION: Synthetic

<400> SEQUENCE: 430

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Gln Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ala Asp Tyr Asp Phe Trp Ser Gly Val Asp Tyr Trp
            100                 105                 110

Gly Gln Gly Thr Leu Val Thr Val Ser Ser
        115                 120

<210> SEQ ID NO 431
<211> LENGTH: 322
<212> TYPE: DNA
<213> ORGANISM: Artificial Sequence
<220> FEATURE:
<223> OTHER INFORMATION: Synthetic

<400> SEQUENCE: 431

```
gacatccaga tgacccagtc tccatcttct gtgtctgcat ctgtaggaga cagagtcacc      60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ctatcagcag cctgcagcct    240
gaagattttg caacttacta ttgtcaacag gctaacagtt tcccattcac tttcggccct    300
gggaccaaag tggatatcaa ac                                              322
```

<210> SEQ ID NO 432
<211> LENGTH: 107
<212> TYPE: PRT
<213> ORGANISM: Artificial Sequence
<220> FEATURE:
<223> OTHER INFORMATION: Synthetic

<400> SEQUENCE: 432

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Phe
                 85                  90                  95

Thr Phe Gly Pro Gly Thr Lys Val Asp Ile Lys
            100                 105

<210> SEQ ID NO 433
<211> LENGTH: 366
<212> TYPE: DNA
<213> ORGANISM: Artificial Sequence
<220> FEATURE:
<223> OTHER INFORMATION: Synthetic

<400> SEQUENCE: 433

```
gaggtgcagc tggtggagtc tgggggaggc ttggtaaagc ctggggggtc ccttagactc      60
tcctgtgcag cctctggatt cactttcagt aacgcctgga tgagctgggt ccgccaggct    120
ccagggaagg ggctgagtg gttggccgt attaaaagca aaactgatgg tgggacaaca    180
gactacgctg cacccgtgaa aggcagattc accatctcaa gagatgattc aaaaacacg    240
ctgtatctgc aaatgaacag cctgaaaacc gaggacacag ccgtgtatta ctgtatcaca    300
gcagattacg attttggag tggggttgac tactggggcc agggaaccct ggtcaccgtc    360
tcctca                                                               366
```

<210> SEQ ID NO 434
<211> LENGTH: 122
<212> TYPE: PRT
<213> ORGANISM: Artificial Sequence
<220> FEATURE:
<223> OTHER INFORMATION: Synthetic

<400> SEQUENCE: 434

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ile Thr Ala Asp Tyr Asp Phe Trp Ser Gly Val Asp Tyr Trp
            100                 105                 110

Gly Gln Gly Thr Leu Val Thr Val Ser Ser
        115                 120

<210> SEQ ID NO 435
<211> LENGTH: 24
<212> TYPE: DNA
<213> ORGANISM: Artificial Sequence
<220> FEATURE:
<223> OTHER INFORMATION: Synthetic

<400> SEQUENCE: 435
ggattcactt tcagtaacgc ctgg                                          24

<210> SEQ ID NO 436
<211> LENGTH: 8
<212> TYPE: PRT
<213> ORGANISM: Artificial Sequence
<220> FEATURE:
<223> OTHER INFORMATION: Synthetic

<400> SEQUENCE: 436

Gly Phe Thr Phe Ser Asn Ala Trp
 1               5

<210> SEQ ID NO 437
<211> LENGTH: 30
<212> TYPE: DNA
<213> ORGANISM: Artificial Sequence
<220> FEATURE:
<223> OTHER INFORMATION: Synthetic

<400> SEQUENCE: 437
attaaaagca aaactgatgg tgggacaaca                                    30

<210> SEQ ID NO 438
<211> LENGTH: 10
<212> TYPE: PRT
<213> ORGANISM: Artificial Sequence
<220> FEATURE:
<223> OTHER INFORMATION: Synthetic

<400> SEQUENCE: 438

Ile Lys Ser Lys Thr Asp Gly Gly Thr Thr
1               5                   10

<210> SEQ ID NO 439
<211> LENGTH: 39
<212> TYPE: DNA
<213> ORGANISM: Artificial Sequence
<220> FEATURE:
<223> OTHER INFORMATION: Synthetic

<400> SEQUENCE: 439
atcacagcag attacgattt ttggagtggg gttgactac         39

<210> SEQ ID NO 440
<211> LENGTH: 13
<212> TYPE: PRT
<213> ORGANISM: Artificial Sequence
<220> FEATURE:
<223> OTHER INFORMATION: Synthetic

<400> SEQUENCE: 440

Ile Thr Ala Asp Tyr Asp Phe Trp Ser Gly Val Asp Tyr
1               5                   10

<210> SEQ ID NO 441
<211> LENGTH: 321
<212> TYPE: DNA
<213> ORGANISM: Artificial Sequence
<220> FEATURE:
<223> OTHER INFORMATION: Synthetic

<400> SEQUENCE: 441
gacatccaga tgacccagtc tccatcttcc gtgtctgcat ctgtaggaga cagagtcacc         60
atcacttgtc gggcgagtca gggtattagc agctggttag cctggtatca gcagaaacca        120
gggaaagccc ctaaactcct gatctatgct gcatccagtt tgcaaagtgg ggtcccatca        180
aggttcagcg gcagtggatc tgggacagat tcactctcca ccatcagcag cctgcagcct        240
gaagattttg caacttacta ttgtcaacag gctaacagtt tcccattcac tttcggccct        300
gggaccaaag tggatatcaa a                                                  321

<210> SEQ ID NO 442
<211> LENGTH: 107
<212> TYPE: PRT
<213> ORGANISM: Artificial Sequence
<220> FEATURE:
<223> OTHER INFORMATION: Synthetic

<400> SEQUENCE: 442

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100             105

<210> SEQ ID NO 443
<211> LENGTH: 18
<212> TYPE: DNA
<213> ORGANISM: Artificial Sequence
<220> FEATURE:
<223> OTHER INFORMATION: Synthetic

<400> SEQUENCE: 443
cagggtatta gcagctgg                                                18

<210> SEQ ID NO 444
<211> LENGTH: 6
<212> TYPE: PRT
<213> ORGANISM: Artificial Sequence
<220> FEATURE:
<223> OTHER INFORMATION: Synthetic

<400> SEQUENCE: 444

Gln Gly Ile Ser Ser Trp
 1               5

<210> SEQ ID NO 445
<211> LENGTH: 9
<212> TYPE: DNA
<213> ORGANISM: Artificial Sequence
<220> FEATURE:
<223> OTHER INFORMATION: Synthetic

<400> SEQUENCE: 445 gctgcatcc                                                          9

<210> SEQ ID NO 446
<211> LENGTH: 3
<212> TYPE: PRT
<213> ORGANISM: Artificial Sequence
<220> FEATURE:
<223> OTHER INFORMATION: Synthetic

<400> SEQUENCE: 446

Ala Ala Ser
 1

<210> SEQ ID NO 447
<211> LENGTH: 27
<212> TYPE: DNA
<213> ORGANISM: Artificial Sequence
<220> FEATURE:
<223> OTHER INFORMATION: Synthetic

<400> SEQUENCE: 447
caacaggcta acagtttccc attcact                                      27

<210> SEQ ID NO 448
<211> LENGTH: 9
<212> TYPE: PRT
<213> ORGANISM: Artificial Sequence
<220> FEATURE:
<223> OTHER INFORMATION: Synthetic

<400> SEQUENCE: 448

Gln Gln Ala Asn Ser Phe Pro Phe Thr
 1               5

<210> SEQ ID NO 449

<211> LENGTH: 366
<212> TYPE: DNA
<213> ORGANISM: Artificial Sequence
<220> FEATURE:
<223> OTHER INFORMATION: Synthetic

<400> SEQUENCE: 449

```
gaggtgcagc tggtggagtc tgggggaggc ttggtaaagc ctggggggtc ccttagactc      60
tcctgtgcag cctctggatt cactttcagt aacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
ctgtatctgc aaatgaacag cctgaaaacc gaggacacag ccgtgtatta ctgtatcaca     300
gcagattacg attttggag tggggttgac tactggggcc agggaaccct ggtcaccgtc     360
tcctca                                                               366
```

<210> SEQ ID NO 450
<211> LENGTH: 122
<212> TYPE: PRT
<213> ORGANISM: Artificial Sequence
<220> FEATURE:
<223> OTHER INFORMATION: Synthetic

<400> SEQUENCE: 450

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asn Ala
            20                  25                  30
Trp Met Ser Trp Val Arg Gln Ala Pro Gly Lys Gly Leu Glu Trp Val
        35                  40                  45
Gly Arg Ile Lys Ser Lys Thr Asp Gly Gly Thr Thr Asp Tyr Ala Ala
    50                  55                  60
Pro Val Lys Gly Arg Phe Thr Ile Ser Arg Asp Asp Ser Lys Asn Thr
65                  70                  75                  80
Leu Tyr Leu Gln Met Asn Ser Leu Lys Thr Glu Asp Thr Ala Val Tyr
                85                  90                  95
Tyr Cys Ile Thr Ala Asp Tyr Asp Phe Trp Ser Gly Val Asp Tyr Trp
            100                 105                 110
Gly Gln Gly Thr Leu Val Thr Val Ser Ser
        115                 120

<210> SEQ ID NO 451
<211> LENGTH: 321
<212> TYPE: DNA
<213> ORGANISM: Artificial Sequence
<220> FEATURE:
<223> OTHER INFORMATION: Synthetic

<400> SEQUENCE: 451

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaaactcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt tcccattcac tttcggccct     300
gggaccaaag tggatatcaa a                                              321
```

<210> SEQ ID NO 452

```
<211> LENGTH: 107
<212> TYPE: PRT
<213> ORGANISM: Artificial Sequence
<220> FEATURE:
<223> OTHER INFORMATION: Synthetic

<400> SEQUENCE: 452

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Phe
                 85                  90                  95

Thr Phe Gly Pro Gly Thr Lys Val Asp Ile Lys
            100                 105

<210> SEQ ID NO 453
<211> LENGTH: 366
<212> TYPE: DNA
<213> ORGANISM: Artificial Sequence
<220> FEATURE:
<223> OTHER INFORMATION: Synthetic

<400> SEQUENCE: 453
gaggtgcagc tggtggagtc tgggggaggc ttggtaaagc ctgggggtc ccttagactc      60 tcctgtgcag cctctggatt cactttcagt aacgcctgga tgagctgggt ccgccaggct    120
ccagggaagg gctggagtg gttggccgt attaaaagca aaactgatgg tgggacaaca     180
gactacgctg cacccgtgaa aggcagattc accatctcaa gagatgattc aaaaaacacg    240
ctgtatctgc aaatgaacag cctgaaaacc gaggacacag ccgtgtatta ctgtatcaca    300
gcagattacg attttggag tggggttgac tactgggggcc agggaaccct ggtcaccgtc    360
tcctca                                                               366

<210> SEQ ID NO 454
<211> LENGTH: 122
<212> TYPE: PRT
<213> ORGANISM: Artificial Sequence
<220> FEATURE:
<223> OTHER INFORMATION: Synthetic

<400> SEQUENCE: 454

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Ser Lys Thr Asp Gly Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95
```

Tyr Cys Ile Thr Ala Asp Tyr Asp Phe Trp Ser Gly Val Asp Tyr Trp
                100                 105                 110

Gly Gln Gly Thr Leu Val Thr Val Ser Ser
        115                 120

<210> SEQ ID NO 455
<211> LENGTH: 322
<212> TYPE: DNA
<213> ORGANISM: Artificial Sequence
<220> FEATURE:
<223> OTHER INFORMATION: Synthetic

<400> SEQUENCE: 455
gacatccaga tgacccagtc tccatcttct gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ctatcagcag cctgcagcct     240
gaagattttg caacttacta ttgtcaacag gctaacagtt tcccattcac tttcggccct     300
gggaccaaag tggatatcaa ac                                              322

<210> SEQ ID NO 456
<211> LENGTH: 107
<212> TYPE: PRT
<213> ORGANISM: Artificial Sequence
<220> FEATURE:
<223> OTHER INFORMATION: Synthetic

<400> SEQUENCE: 456

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 457
<211> LENGTH: 363
<212> TYPE: DNA
<213> ORGANISM: Artificial Sequence
<220> FEATURE:
<223> OTHER INFORMATION: Synthetic

<400> SEQUENCE: 457
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg gtctcaggt attagttgga atagtggtag catagtctat      180
gcggactctg tgaagggccg attcaccatc tccagagaca cgccaagaa ctccctgtat      240 ctgcaaatga acagtctaat atctgaggac acggccttgt attactgtgc aaaagatgaa     300

```
agcagctcgt cggggaactg gttcgacccc tgggccagg gaaccctggt caccgtctcc    360
tca                                                                 363
```

<210> SEQ ID NO 458
<211> LENGTH: 121
<212> TYPE: PRT
<213> ORGANISM: Artificial Sequence
<220> FEATURE:
<223> OTHER INFORMATION: Synthetic

<400> SEQUENCE: 458

```
Glu Val Gln Leu Val Glu Ser Gly Gly Gly Leu Val Gln Pro Gly Arg
 1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Ile Ser Glu Asp Thr Ala Leu Tyr Tyr Cys
                85                  90                  95

Ala Lys Asp Glu Ser Ser Ser Ser Gly Asn Trp Phe Asp Pro Trp Gly
            100                 105                 110

Gln Gly Thr Leu Val Thr Val Ser Ser
        115                 120
```

<210> SEQ ID NO 459
<211> LENGTH: 24
<212> TYPE: DNA
<213> ORGANISM: Artificial Sequence
<220> FEATURE:
<223> OTHER INFORMATION: Synthetic

<400> SEQUENCE: 459

```
ggattcacct ttgatgatta tgcc                                           24
```

<210> SEQ ID NO 460
<211> LENGTH: 8
<212> TYPE: PRT
<213> ORGANISM: Artificial Sequence
<220> FEATURE:
<223> OTHER INFORMATION: Synthetic

<400> SEQUENCE: 460

```
Gly Phe Thr Phe Asp Asp Tyr Ala
 1               5
```

<210> SEQ ID NO 461
<211> LENGTH: 24
<212> TYPE: DNA
<213> ORGANISM: Artificial Sequence
<220> FEATURE:
<223> OTHER INFORMATION: Synthetic

<400> SEQUENCE: 461

```
attagttgga atagtggtag cata                                           24
```

<210> SEQ ID NO 462
<211> LENGTH: 8
<212> TYPE: PRT
<213> ORGANISM: Artificial Sequence

```
<220> FEATURE:
<223> OTHER INFORMATION: Synthetic

<400> SEQUENCE: 462

Ile Ser Trp Asn Ser Gly Ser Ile
1               5

<210> SEQ ID NO 463
<211> LENGTH: 42
<212> TYPE: DNA
<213> ORGANISM: Artificial Sequence
<220> FEATURE:
<223> OTHER INFORMATION: Synthetic

<400> SEQUENCE: 463
gcaaaagatg aaagcagctc gtcggggaac tggttcgacc cc                    42

<210> SEQ ID NO 464
<211> LENGTH: 14
<212> TYPE: PRT
<213> ORGANISM: Artificial Sequence
<220> FEATURE:
<223> OTHER INFORMATION: Synthetic

<400> SEQUENCE: 464

Ala Lys Asp Glu Ser Ser Ser Gly Asn Trp Phe Asp Pro
1               5                   10

<210> SEQ ID NO 465
<211> LENGTH: 363
<212> TYPE: DNA
<213> ORGANISM: Artificial Sequence
<220> FEATURE:
<223> OTHER INFORMATION: Synthetic

<400> SEQUENCE: 465
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtag catagtctat   180
gcggactctg tgaagggccg attcaccatc tccagagaca cgccaagaa ctccctgtat    240 ctgcaaatga acagtctaat atctgaggac acggccttgt attactgtgc aaaagatgaa   300
agcagctcgt cggggaactg gttcgacccc tggggccagg gaaccctggt caccgtctcc   360
tca                                                                363

<210> SEQ ID NO 466
<211> LENGTH: 121
<212> TYPE: PRT
<213> ORGANISM: Artificial Sequence
<220> FEATURE:
<223> OTHER INFORMATION: Synthetic

<400> SEQUENCE: 466

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Val Tyr Ala Asp Ser Val
    50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Ile Ser Glu Asp Thr Ala Leu Tyr Tyr Cys
                    85                  90                  95

Ala Lys Asp Glu Ser Ser Ser Gly Asn Trp Phe Asp Pro Trp Gly
                100                 105                 110

Gln Gly Thr Leu Val Thr Val Ser Ser
                115                 120
```

<210> SEQ ID NO 467
<211> LENGTH: 363
<212> TYPE: DNA
<213> ORGANISM: Artificial Sequence
<220> FEATURE:
<223> OTHER INFORMATION: Synthetic

<400> SEQUENCE: 467

```
gaagtgcagc tggtggagtc tgggggaggc ttggtacagc ctggcaggtc cctgagactc    60
tcctgtgcag cctctggatt cacctttgat gattatgcca tgcactgggt ccggcaagct   120
ccagggaagg gcctggagtg ggtctcaggt attagttgga atagtggtag cataggctat   180
gcggactctg tgaagggccg attcaccatc tccagagaca acgccaagaa ctccctgtat   240
ctgcaaatga acagtctgag agctgaggac acggccttgt attactgtgc aaaagatgaa   300
agcagctcgt cggggaactg gttcgacccc tggggccagg aaccctggt caccgtctcc   360 tca                                                                 363
```

<210> SEQ ID NO 468
<211> LENGTH: 121
<212> TYPE: PRT
<213> ORGANISM: Artificial Sequence
<220> FEATURE:
<223> OTHER INFORMATION: Synthetic

<400> SEQUENCE: 468

```
Glu Val Gln Leu Val Glu Ser Gly Gly Gly Leu Val Gln Pro Gly Arg
  1               5                  10                  15

Ser Leu Arg Leu Ser Cys Ala Ala Ser Gly Phe Thr Phe Asp Asp Tyr
             20                  25                  30

Ala Met His Trp Val Arg Gln Ala Pro Gly Lys Gly Leu Glu Trp Val
         35                  40                  45

Ser Gly Ile Ser Trp Asn Ser Gly Ser Ile Gly Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                    85                  90                  95

Ala Lys Asp Glu Ser Ser Ser Gly Asn Trp Phe Asp Pro Trp Gly
                100                 105                 110

Gln Gly Thr Leu Val Thr Val Ser Ser
                115                 120
```

<210> SEQ ID NO 469
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly

```
<220> FEATURE:
<221> NAME/KEY: VARIANT
<222> LOCATION: (2)...(2)
<223> OTHER INFORMATION: Xaa = Gly or Phe
<220> FEATURE:
<221> NAME/KEY: VARIANT
<222> LOCATION: (3)...(3)
<223> OTHER INFORMATION: Xaa = Ser or Thr
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Ser
<220> FEATURE:
<221> NAME/KEY: VARIANT
<222> LOCATION: (6)...(6)
<223> OTHER INFORMATION: Xaa = Ile, Ser, or Thr
<220> FEATURE:
<221> NAME/KEY: VARIANT
<222> LOCATION: (7)...(7)
<223> OTHER INFORMATION: Xaa = His or Tyr
<220> FEATURE:
<221> NAME/KEY: VARIANT
<222> LOCATION: (8)...(8)
<223> OTHER INFORMATION: Xaa = His, Gly, or Asp

<400> SEQUENCE: 469

Xaa Xaa Xaa Xaa Xaa Xaa Xaa Xaa
 1               5

<210> SEQ ID NO 470
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Asn, Ser, or Gly
<220> FEATURE:
<221> NAME/KEY: VARIANT
<222> LOCATION: (3)...(3)
<223> OTHER INFORMATION: Xaa = His, Phe, Ser, or Val
<220> FEATURE:
<221> NAME/KEY: VARIANT
<222> LOCATION: (4)...(4)
<223> OTHER INFORMATION: Xaa = Arg, Asp, or Ala
<220> FEATURE:
<221> NAME/KEY: VARIANT
<222> LOCATION: (5)...(5)
<223> OTHER INFORMATION: Xaa = Gly
<220> FEATURE:
<221> NAME/KEY: VARIANT
<222> LOCATION: (6)...(6)
<223> OTHER INFORMATION: Xaa = Gly or absent
<220> FEATURE:
<221> NAME/KEY: VARIANT
<222> LOCATION: (7)...(7)
<223> OTHER INFORMATION: Xaa = Ser, Asn, or Asp
<220> FEATURE:
<221> NAME/KEY: VARIANT
<222> LOCATION: (8)...(8)
<223> OTHER INFORMATION: Xaa = Thr or Lys

<400> SEQUENCE: 470

Xaa Xaa Xaa Xaa Xaa Xaa Xaa Xaa
 1               5
```

```
<210> SEQ ID NO 471
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala
<220> FEATURE:
<221> NAME/KEY: VARIANT
<222> LOCATION: (2)...(2)
<223> OTHER INFORMATION: Xaa = Arg or Lys
<220> FEATURE:
<221> NAME/KEY: VARIANT
<222> LOCATION: (3)...(3)
<223> OTHER INFORMATION: Xaa = Gly or Glu
<220> FEATURE:
<221> NAME/KEY: VARIANT
<222> LOCATION: (4)...(4)
<223> OTHER INFORMATION: Xaa = Gly, Asp, or absent
<220> FEATURE:
<221> NAME/KEY: VARIANT
<222> LOCATION: (5)...(5)
<223> OTHER INFORMATION: Xaa = Asp or absent
<220> FEATURE:
<221> NAME/KEY: VARIANT
<222> LOCATION: (6)...(6)
<223> OTHER INFORMATION: Xaa = Leu, Arg, or absent
<220> FEATURE:
<221> NAME/KEY: VARIANT
<222> LOCATION: (7)...(7)
<223> OTHER INFORMATION: Xaa = Arg or Ser
<220> FEATURE:
<221> NAME/KEY: VARIANT
<222> LOCATION: (8)...(8)
<223> OTHER INFORMATION: Xaa = Phe, Gly, or Arg
<220> FEATURE:
<221> NAME/KEY: VARIANT
<222> LOCATION: (9)...(9)
<223> OTHER INFORMATION: Xaa = Leu, His, or Asn
<220> FEATURE:
<221> NAME/KEY: VARIANT
<222> LOCATION: (10)...(10)
<223> OTHER INFORMATION: Xaa = Asp, Pro, or Tyr
<220> FEATURE:
<221> NAME/KEY: VARIANT
<222> LOCATION: (11)...(11)
<223> OTHER INFORMATION: Xaa = Trp, Tyr, or Phe
<220> FEATURE:
<221> NAME/KEY: VARIANT
<222> LOCATION: (12)...(12)
<223> OTHER INFORMATION: Xaa = Leu, Phe, Val, or Asp
<220> FEATURE:
<221> NAME/KEY: VARIANT
<222> LOCATION: (13)...(13)
<223> OTHER INFORMATION: Xaa = Ser, Tyr, or Gly
<220> FEATURE:
<221> NAME/KEY: VARIANT
<222> LOCATION: (14)...(14)
<223> OTHER INFORMATION: Xaa = Ser, Tyr, or Asp
<220> FEATURE:
<221> NAME/KEY: VARIANT
<222> LOCATION: (15)...(15)
<223> OTHER INFORMATION: Xaa = Tyr
<220> FEATURE:
<221> NAME/KEY: VARIANT
<222> LOCATION: (16)...(16)
<223> OTHER INFORMATION: Xaa = Phe or Gly
<220> FEATURE:
<221> NAME/KEY: VARIANT
<222> LOCATION: (17)...(17)
<223> OTHER INFORMATION: Xaa = Leu or absent
<220> FEATURE:
<221> NAME/KEY: VARIANT
<222> LOCATION: (18)...(18)
<223> OTHER INFORMATION: Xaa = Asp
<220> FEATURE:
<221> NAME/KEY: VARIANT
```

```
<222> LOCATION: (19)...(19)
<223> OTHER INFORMATION: Xaa = Tyr, Val, or Phe
<220> FEATURE:
<221> NAME/KEY: VARIANT
<222> LOCATION: (20)...(20)
<223> OTHER INFORMATION: Xaa = Trp

<400> SEQUENCE: 471

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa
            20

<210> SEQ ID NO 472
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gly or Ser
<220> FEATURE:
<221> NAME/KEY: VARIANT
<222> LOCATION: (3)...(3)
<223> OTHER INFORMATION: Xaa = Ile
<220> FEATURE:
<221> NAME/KEY: VARIANT
<222> LOCATION: (4)...(4)
<223> OTHER INFORMATION: Xaa = Ser or Asn
<220> FEATURE:
<221> NAME/KEY: VARIANT
<222> LOCATION: (5)...(5)
<223> OTHER INFORMATION: Xaa = Asp, Ser, or Arg
<220> FEATURE:
<221> NAME/KEY: VARIANT
<222> LOCATION: (6)...(6)
<223> OTHER INFORMATION: Xaa = Tyr or Trp

<400> SEQUENCE: 472

Xaa Xaa Xaa Xaa Xaa Xaa
 1               5

<210> SEQ ID NO 473
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala or Lys
<220> FEATURE:
<221> NAME/KEY: VARIANT
<222> LOCATION: (2)...(2)
<223> OTHER INFORMATION: Xaa = Ala
<220> FEATURE:
<221> NAME/KEY: VARIANT
<222> LOCATION: (3)...(3)
<223> OTHER INFORMATION: Xaa = Ser

<400> SEQUENCE: 473

Xaa Xaa Xaa
 1

<210> SEQ ID NO 474
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Asn or Gln
<220> FEATURE:
<221> NAME/KEY: VARIANT
<222> LOCATION: (3)...(3)
<223> OTHER INFORMATION: Xaa = Tyr or Leu
<220> FEATURE:
<221> NAME/KEY: VARIANT
<222> LOCATION: (4)...(4)
<223> OTHER INFORMATION: Xaa = Asn, His, Ser, or Asp
<220> FEATURE:
<221> NAME/KEY: VARIANT
<222> LOCATION: (5)...(5)
<223> OTHER INFORMATION: Xaa = Thr or Ser
<220> FEATURE:
<221> NAME/KEY: VARIANT
<222> LOCATION: (6)...(6)
<223> OTHER INFORMATION: Xaa = Ala or Tyr
<220> FEATURE:
<221> NAME/KEY: VARIANT
<222> LOCATION: (7)...(7)
<223> OTHER INFORMATION: Xaa = Pro, Ser, or Phe
<220> FEATURE:
<221> NAME/KEY: VARIANT
<222> LOCATION: (8)...(8)
<223> OTHER INFORMATION: Xaa = Leu or Arg
<220> FEATURE:
<221> NAME/KEY: VARIANT
<222> LOCATION: (9)...(9)
<223> OTHER INFORMATION: Xaa = Thr
<220> FEATURE:
<221> NAME/KEY: VARIANT
<222> LOCATION: (10)...(10)
<223> OTHER INFORMATION: Xaa = Phe

<400> SEQUENCE: 474

Xaa Xaa Xaa Xaa Xaa Xaa Xaa Xaa Xaa Xaa
 1               5                   10

<210> SEQ ID NO 475
<211> LENGTH: 1221
<212> TYPE: DNA
<213> ORGANISM: Homo sapiens

<400> SEQUENCE: 475
atgagcggtg ctccgacggc cggggcagcc ctgatgctct gcgccgccac cgccgtgcta      60
ctgagcgctc agggcggacc cgtgcagtcc aagtcgccgc gctttgcgtc ctgggacgag     120
atgaatgtcc tggcgcacgg actcctgcag ctcggccagg ggctgcgcga acacgcggag     180
cgcacccgca gtcagctgag cgcgctggag cggcgcctga gcgcgtgcgg gtccgcctgt     240
cagggaaccg aggggtccac cgacctcccg ttagccctg agagccgggt ggaccctgag      300
gtccttcaca gcctgcagac acaactcaag gctcagaaca gcaggatcca gcaactcttc     360
cacaaggtgg cccagcagca gcggcacctg gagaagcagc acctgcgaat tcagcatctg     420
caaagccagt ttggcctcct ggaccacaag cacctagacc atgaggtggc caagcctgcc     480
cgaagaaaga ggctgcccga gatggcccag ccagttgacc cggctcacaa tgtcagccgc     540
ctgcaccggc tgcccaggga ttgccaggag ctgttccagg ttggggagag cagagtggac     600
ctatttgaaa tccagcctca ggggtctccg ccatttttgg tgaactgcaa gatgacctca     660
```

-continued

```
gatggaggct ggacagtaat tcagaggcgc cacgatggct cagtggactt caaccggccc    720
tgggaagcct acaaggcggg gtttggggat ccccacggcg agttctggct gggtctggag    780
aaggtgcata gcatcacggg ggaccgcaac agccgcctgg ccgtgcagct gcgggactgg    840
gatggcaacg ccgagttgct gcagttctcc gtgcacctgg gtggcgagga cacggcctat    900
agcctgcagc tcactgcacc cgtggccggc cagctgggcg ccaccaccgt cccacccagc    960
ggcctctccg tacccttctc cacttgggac caggatcacg acctccgcag ggacaagaac   1020
tgcgccaaga gcctctctgg aggctggtgg tttggcacct gcagccattc aacctcaac    1080 ggccagtact ccgctccat cccacagcag cggcagaagc ttaagaaggg aatcttctgg    1140
aagacctggc ggggccgcta ctacccgctg caggccacca ccatgttgat ccagcccatg   1200
gcagcagagg cagcctccta g                                              1221
```

<210> SEQ ID NO 476
<211> LENGTH: 406
<212> TYPE: PRT
<213> ORGANISM: Homo sapiens

<400> SEQUENCE: 476

```
Met Ser Gly Ala Pro Thr Ala Gly Ala Ala Leu Met Leu Cys Ala Ala
 1               5                  10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
```

```
                  275                 280                 285
Phe Ser Val His Leu Gly Gly Glu Asp Thr Ala Tyr Ser Leu Gln Leu
290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Trp Trp Phe Gly
                340                 345                 350

Thr Cys Ser His Ser Asn Leu Asn Gly Gln Tyr Phe Arg Ser Ile Pro
                355                 360                 365

Gln Gln Arg Gln Lys Leu Lys Lys Gly Ile Phe Trp Lys Thr Trp Arg
370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 477
<211> LENGTH: 1233
<212> TYPE: DNA
<213> ORGANISM: Mus muscular

<400> SEQUENCE: 477
atgcgctgcg ctccgacagc aggcgctgcc ctggtgctat gcgcggctac tgcggggctt      60
ttgagcgcgc aagggcgccc tgcacagcca gagccaccgc gctttgcatc ctgggacgag     120
atgaacttgc tggctcacgg gctgctacag ctcggccatg gctgcgcgcga acacgtggag     180 cgcacccgtg ggcagctggg cgcgctggag cgccgcatgg ctgcctgtgg taacgcttgt     240
caggggccca aggaaaaga tgcacccttc aaagactccg aggatagagt ccctgaaggc     300
cagactcctg agactctgca gagtttgcag actcagctca aggctcaaaa cagcaagatc     360
cagcaattgt tccagaaggt ggcccagcag cagagatacc tatcaaagca gaatctgaga     420
atacagaatc ttcagagcca gatagacctc ttggcccccca cgcacctaga caatggagta     480
gacaagactt cgaggggaaa gaggcttccc aagatgaccc agctcattgg cttgactccc     540
aacgccaccc acttacacag gccgccccgg gactgccagg aactcttcca agaaggggag     600
cggcacagtg acttttcca gatccagcct ctggggtctc caccattttt ggtcaactgt     660
gagatgactt cagatggagg ctggacagtg attcagagac gcctgaacgg ctctgtggac     720
ttcaaccagt cctgggaagc ctacaaggat ggcttcggag atccccaagg cgagttctgg     780
ctgggcctgg aaaagatgca cagcatcaca gggaaccgag aagccaatt ggctgtgcag     840 ctccaggact gggatggcaa tgccaaattg ctccaatttc ccatccattt ggggggtgag     900
gacacagcct acagcctgca gctcactgag cccacggcca atgagctggg tgccaccaat     960 gtttcccccca atggccttc cctgcccttc tctacttggg accaagacca tgacctccgt    1020 ggggaccctta actgtgccaa gagcctctct ggtggctggt ggtttggtac ctgtagccat    1080
tccaatctca atggacaata cttccactct atcccacggc aacggcagga gcgtaaaaag    1140
ggtatcttct ggaaaacatg gaagggccgc tactatcctc tgcaggctac caccctgctg    1200
atccagccca tggaggctac agcagcctct tag                                  1233

<210> SEQ ID NO 478
<211> LENGTH: 410
<212> TYPE: PRT
```

<213> ORGANISM: Mus muscular

<400> SEQUENCE: 478

```
Met Arg Cys Ala Pro Thr Ala Gly Ala Ala Leu Val Leu Cys Ala Ala
 1               5                  10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly Pro Lys Gly Lys Asp Ala Pro Phe Lys Asp Ser Glu Asp Arg
                85                  90                  95

Val Pro Glu Gly Gln Thr Pro Glu Thr Leu Gln Ser Leu Gln Thr Gln
            100                 105                 110

Leu Lys Ala Gln Asn Ser Lys Ile Gln Gln Leu Phe Gln Lys Val Ala
        115                 120                 125

Gln Gln Gln Arg Tyr Leu Ser Lys Gln Asn Leu Arg Ile Gln Asn Leu
    130                 135                 140

Gln Ser Gln Ile Asp Leu Leu Ala Pro Thr His Leu Asp Asn Gly Val
145                 150                 155                 160

Asp Lys Thr Ser Arg Gly Lys Arg Leu Pro Lys Met Thr Gln Leu Ile
                165                 170                 175

Gly Leu Thr Pro Asn Ala Thr His Leu His Arg Pro Pro Arg Asp Cys
            180                 185                 190

Gln Glu Leu Phe Gln Glu Gly Glu Arg His Ser Gly Leu Phe Gln Ile
        195                 200                 205

Gln Pro Leu Gly Ser Pro Pro Phe Leu Val Asn Cys Glu Met Thr Ser
    210                 215                 220

Asp Gly Gly Trp Thr Val Ile Gln Arg Arg Leu Asn Gly Ser Val Asp
225                 230                 235                 240

Phe Asn Gln Ser Trp Glu Ala Tyr Lys Asp Gly Phe Gly Asp Pro Gln
                245                 250                 255

Gly Glu Phe Trp Leu Gly Leu Glu Lys Met His Ser Ile Thr Gly Asn
            260                 265                 270

Arg Gly Ser Gln Leu Ala Val Gln Leu Gln Asp Trp Asp Gly Asn Ala
        275                 280                 285

Lys Leu Leu Gln Phe Pro Ile His Leu Gly Gly Glu Asp Thr Ala Tyr
    290                 295                 300

Ser Leu Gln Leu Thr Glu Pro Thr Ala Asn Glu Leu Gly Ala Thr Asn
305                 310                 315                 320

Val Ser Pro Asn Gly Leu Ser Leu Pro Phe Ser Thr Trp Asp Gln Asp
                325                 330                 335

His Asp Leu Arg Gly Asp Leu Asn Cys Ala Lys Ser Leu Ser Gly Gly
            340                 345                 350

Trp Trp Phe Gly Thr Cys Ser His Ser Asn Leu Asn Gly Gln Tyr Phe
        355                 360                 365

His Ser Ile Pro Arg Gln Arg Gln Glu Arg Lys Lys Gly Ile Phe Trp
    370                 375                 380

Lys Thr Trp Lys Gly Arg Tyr Tyr Pro Leu Gln Ala Thr Thr Leu Leu
385                 390                 395                 400

Ile Gln Pro Met Glu Ala Thr Ala Ala Ser
```

<210> SEQ ID NO 479
<211> LENGTH: 1110
<212> TYPE: DNA
<213> ORGANISM: Artificial Sequence
<220> FEATURE:
<223> OTHER INFORMATION: Synthetic

<400> SEQUENCE: 479

```
ggacccgtgc agtccaagtc gccgcgcttt gcgtcctggg acgagatgaa tgtcctggcg      60
cacggactcc tgcagctcgg ccaggggctg cgcgaacacg cggagcgcac cgcagtcag     120
ctgagcgcgc tggagcggcg cctgagcgcg tgcgggtccg cctgtcaggg aaccgagggg    180
tccaccgacc tcccgttagc ccctgagagc cgggtggacc ctgaggtcct tcacagcctg    240
cagacacaac tcaaggctca gaacagcagg atccagcaac tcttccacaa ggtggcccag    300
cagcagcggc acctggagaa gcagcacctg cgaattcagc atctgcaaag ccagtttggc    360
ctcctggacc ccgggtctct cgaattcgcc cttgagagaa actccggaga gcccagaggg    420
cccacaatca gccctgtcc tccatgcaaa tgcccagcac ctaacctctt gggtggacca    480
tccgtcttca tcttccctcc aaagatcaag gatgtactca tgatctccct gagccccata    540
gtcacatgtg tggtggtgga tgtgagcgag gatgacccag atgtccagat cagctggttt    600
gtgaacaacg tggaagtaca cacagctcag acacaaaccc atagagagga ttacaacagt    660
actctccggg tggtcagtgc cctcccatc cagcaccagg actggatgag tggcaaggag    720
ttcaaatgca aggtcaacaa caaagaccttc ccagcgccca tcgagagaac catctcaaaa    780
cccaaagggt cagtaagagc tccacaggta tatgtcttgc ctccaccaga agaagagatg    840
actaagaaac aggtcactct gacctgcatg gtcacagact tcatgcctga agacatttac    900
gtggagtgga ccaacaacgg gaaaacagag ctaaactaca gaacactga accagtcctg    960
gactctgatg gttcttactt catgtacagc aagctgagag tggaaaagaa gaactgggtg   1020
gaaagaaata gctactcctg ttcagtggtc cacgagggtc tgcacaatca ccacacgact   1080
aagagcttct cccggactcc gggtaaatga                                    1110
```

<210> SEQ ID NO 480
<211> LENGTH: 369
<212> TYPE: PRT
<213> ORGANISM: Artificial Sequence
<220> FEATURE:
<223> OTHER INFORMATION: Synthetic

<400> SEQUENCE: 480

```
Gly Pro Val Gln Ser Lys Ser Pro Arg Phe Ala Ser Trp Asp Glu Met
  1               5                  10                  15

Asn Val Leu Ala His Gly Leu Leu Gln Leu Gly Gln Gly Leu Arg Glu
             20                  25                  30

His Ala Glu Arg Thr Arg Ser Gln Leu Ser Ala Leu Glu Arg Arg Leu
         35                  40                  45

Ser Ala Cys Gly Ser Ala Cys Gln Gly Thr Glu Gly Ser Thr Asp Leu
     50                  55                  60

Pro Leu Ala Pro Glu Ser Arg Val Asp Pro Glu Val Leu His Ser Leu
 65                  70                  75                  80

Gln Thr Gln Leu Lys Ala Gln Asn Ser Arg Ile Gln Gln Leu Phe His
                 85                  90                  95

Lys Val Ala Gln Gln Gln Arg His Leu Glu Lys Gln His Leu Arg Ile
            100                 105                 110
```

```
Gln His Leu Gln Ser Gln Phe Gly Leu Leu Asp Pro Gly Ser Leu Glu
        115                 120                 125

Phe Ala Leu Glu Arg Asn Ser Gly Glu Pro Arg Gly Pro Thr Ile Lys
        130                 135                 140

Pro Cys Pro Pro Cys Lys Cys Pro Ala Pro Asn Leu Leu Gly Gly Pro
145                 150                 155                 160

Ser Val Phe Ile Phe Pro Pro Lys Ile Lys Asp Val Leu Met Ile Ser
                165                 170                 175

Leu Ser Pro Ile Val Thr Cys Val Val Val Asp Val Ser Glu Asp Asp
            180                 185                 190

Pro Asp Val Gln Ile Ser Trp Phe Val Asn Asn Val Glu Val His Thr
        195                 200                 205

Ala Gln Thr Gln Thr His Arg Glu Asp Tyr Asn Ser Thr Leu Arg Val
        210                 215                 220

Val Ser Ala Leu Pro Ile Gln His Gln Asp Trp Met Ser Gly Lys Glu
225                 230                 235                 240

Phe Lys Cys Lys Val Asn Asn Lys Asp Leu Pro Ala Pro Ile Glu Arg
                245                 250                 255

Thr Ile Ser Lys Pro Lys Gly Ser Val Arg Ala Pro Gln Val Tyr Val
            260                 265                 270

Leu Pro Pro Pro Glu Glu Glu Met Thr Lys Lys Gln Val Thr Leu Thr
        275                 280                 285

Cys Met Val Thr Asp Phe Met Pro Glu Asp Ile Tyr Val Glu Trp Thr
290                 295                 300

Asn Asn Gly Lys Thr Glu Leu Asn Tyr Lys Asn Thr Glu Pro Val Leu
305                 310                 315                 320

Asp Ser Asp Gly Ser Tyr Phe Met Tyr Ser Lys Leu Arg Val Glu Lys
                325                 330                 335

Lys Asn Trp Val Glu Arg Asn Ser Tyr Ser Cys Ser Val Val His Glu
            340                 345                 350

Gly Leu His Asn His His Thr Thr Lys Ser Phe Ser Arg Thr Pro Gly
        355                 360                 365

Lys

<210> SEQ ID NO 481
<211> LENGTH: 330
<212> TYPE: PRT
<213> ORGANISM: Artificial Sequence
<220> FEATURE:
<223> OTHER INFORMATION: Synthetic

<400> SEQUENCE: 481

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
                    100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 482
<211> LENGTH: 327
<212> TYPE: PRT
<213> ORGANISM: Artificial Sequence
<220> FEATURE:
<223> OTHER INFORMATION: Synthetic

<400> SEQUENCE: 482

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Ser Cys Pro Ala Pro
            100                 105                 110
Glu Phe Leu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
```

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 483
<211> LENGTH: 327
<212> TYPE: PRT
<213> ORGANISM: Artificial Sequence
<220> FEATURE:
<223> OTHER INFORMATION: Synthetic

<400> SEQUENCE: 483

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

```
Asn Ser Thr Tyr Arg Val Val Ser Val Leu Thr Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 484
<211> LENGTH: 455
<212> TYPE: PRT
<213> ORGANISM: Mus muscular

<400> SEQUENCE: 484

Met His Thr Ile Lys Leu Phe Leu Phe Val Val Pro Leu Val Ile Ala
1               5                   10                  15

Ser Arg Val Asp Pro Asp Leu Ser Ser Phe Asp Ser Ala Pro Ser Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Arg Thr Asn Glu Ile Lys Glu Glu Glu
                85                  90                  95

Lys Glu Leu Arg Arg Thr Thr Ser Thr Leu Gln Val Lys Asn Glu Glu
            100                 105                 110

Val Lys Asn Met Ser Val Glu Leu Asn Ser Lys Leu Glu Ser Leu Leu
        115                 120                 125

Glu Glu Lys Thr Ala Leu Gln His Lys Val Arg Ala Leu Glu Glu Gln
    130                 135                 140

Leu Thr Asn Leu Ile Leu Ser Pro Ala Gly Ala Gln Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Glu Gln Tyr Lys Gln Leu Ser Gln Gln
            180                 185                 190

His Met Gln Ile Lys Glu Ile Glu Lys Gln Leu Arg Lys Thr Gly Ile
        195                 200                 205

Gln Glu Pro Ser Glu Asn Ser Leu Ser Ser Lys Ser Arg Ala Pro Arg
    210                 215                 220
```

```
Thr Thr Pro Pro Leu Gln Leu Asn Glu Thr Glu Asn Thr Glu Gln Asp
225                 230                 235                 240

Asp Leu Pro Ala Asp Cys Ser Ala Val Tyr Asn Arg Gly Glu His Thr
                245                 250                 255

Ser Gly Val Tyr Thr Ile Lys Pro Arg Asn Ser Gln Gly Phe Asn Val
            260                 265                 270

Tyr Cys Asp Thr Gln Ser Gly Ser Pro Trp Thr Leu Ile Gln His Arg
        275                 280                 285

Lys Asp Gly Ser Gln Asp Phe Asn Glu Thr Trp Glu Asn Tyr Glu Lys
    290                 295                 300

Gly Phe Gly Arg Leu Asp Gly Glu Phe Trp Leu Gly Leu Glu Lys Ile
305                 310                 315                 320

Tyr Ala Ile Val Gln Gln Ser Asn Tyr Ile Leu Arg Leu Glu Leu Gln
                325                 330                 335

Asp Trp Lys Asp Ser Lys His Tyr Val Glu Tyr Ser Phe His Leu Gly
                340                 345                 350

Ser His Glu Thr Asn Tyr Thr Leu His Val Ala Glu Ile Ala Gly Asn
        355                 360                 365

Ile Pro Gly Ala Leu Pro Glu His Thr Asp Leu Met Phe Ser Thr Trp
370                 375                 380

Asn His Arg Ala Lys Gly Gln Leu Tyr Cys Pro Glu Ser Tyr Ser Gly
385                 390                 395                 400

Gly Trp Trp Trp Asn Asp Ile Cys Gly Glu Asn Asn Leu Asn Gly Lys
                405                 410                 415

Tyr Asn Lys Pro Arg Thr Lys Ser Arg Pro Glu Arg Arg Arg Gly Ile
                420                 425                 430

Tyr Trp Arg Pro Gln Ser Arg Lys Leu Tyr Ala Ile Lys Ser Ser Lys
                435                 440                 445

Met Met Leu Gln Pro Thr Thr
    450                 455

<210> SEQ ID NO 485
<211> LENGTH: 460
<212> TYPE: PRT
<213> ORGANISM: Homo sapiens

<400> SEQUENCE: 485

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140
```

```
Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
            165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
            195                 200                 205

Gln Glu Pro Thr Glu Ile Ser Leu Ser Ser Lys Pro Arg Ala Pro Arg
210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
            245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
            275                 280                 285

Ile Asp Gly Ser Gln Asn Phe Asn Glu Thr Trp Glu Asn Tyr Lys Tyr
290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
            325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
            355                 360                 365

Val Pro Asn Ala Ile Pro Glu Asn Lys Asp Leu Val Phe Ser Thr Trp
370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
            405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
            435                 440                 445

Met Leu Ile His Pro Thr Asp Ser Glu Ser Phe Glu
            450                 455                 460

<210> SEQ ID NO 486
<211> LENGTH: 366
<212> TYPE: DNA
<213> ORGANISM: Artificial Sequence
<220> FEATURE:
<223> OTHER INFORMATION: Synthetic

<400> SEQUENCE: 486
caggtacagc tgcagcagtc gggcgcagga ctgttgaagc cttcggagac cctgtccctc      60
acctgcactg tctatggtgg atccttcagt attcatcact ggacctggat ccgccatccc     120
ccagggaagg ggctggagtg gattggggag atcaatcatc gtggaagcac caactacaac     180
ccgtccctca agagtcgagt caccatatca atagacacgt ccaagaacca gttctccctg     240
aagctgagcg ctgtgaccgc cgcggacacg gctgtatatt actgtgcgag aggcttacga     300
```
tttttggact ggttatcgtc ctactttgac tactggggcc agggaaccct ggtcaccgtc   360
tcctca                                                              366

<210> SEQ ID NO 487
<211> LENGTH: 122
<212> TYPE: PRT
<213> ORGANISM: Artificial Sequence
<220> FEATURE:
<223> OTHER INFORMATION: Synthetic

<400> SEQUENCE: 487

Gln Val Gln Leu Gln Gln Ser Gly Ala Gly Leu Leu Lys Pro Ser Glu
 1               5                  10                  15

Thr Leu Ser Leu Thr Cys Thr Val Tyr Gly Gly Ser Phe Ser Ile His
             20                  25                  30

His Trp Thr Trp Ile Arg His Pro Pro Gly Lys Gly Leu Glu Trp Ile
         35                  40                  45

Gly Glu Ile Asn His Arg Gly Ser Thr Asn Tyr Asn Pro Ser Leu Lys
     50                  55                  60

Ser Arg Val Thr Ile Ser Ile Asp Thr Ser Lys Asn Gln Phe Ser Leu
65                  70                  75                  80

Lys Leu Ser Ala Val Thr Ala Ala Asp Thr Ala Val Tyr Tyr Cys Ala
                 85                  90                  95

Arg Gly Leu Arg Phe Leu Asp Trp Leu Ser Ser Tyr Phe Asp Tyr Trp
            100                 105                 110

Gly Gln Gly Thr Leu Val Thr Val Ser Ser
        115                 120

<210> SEQ ID NO 488
<211> LENGTH: 130
<212> TYPE: PRT
<213> ORGANISM: Artificial Sequence
<220> FEATURE:
<223> OTHER INFORMATION: Synthetic

<400> SEQUENCE: 488

Met His His His His His Gly Pro Val Gln Ser Lys Ser Pro Arg
 1               5                  10                  15

Phe Ala Ser Trp Asp Glu Met Asn Val Leu Ala His Gly Leu Leu Gln
             20                  25                  30

Leu Gly Gln Gly Leu Arg Glu His Ala Glu Arg Thr Arg Ser Gln Leu
         35                  40                  45

Asn Ala Leu Glu Arg Arg Leu Ser Ala Cys Gly Ser Ala Cys Gln Gly
     50                  55                  60

Thr Glu Gly Ser Thr Ala Leu Pro Leu Ala Pro Glu Ser Arg Val Asp
65                  70                  75                  80

Pro Glu Val Leu His Ser Leu Gln Thr Gln Leu Lys Ala Gln Asn Ser
                 85                  90                  95

Arg Ile Gln Gln Leu Phe His Lys Val Ala Gln Gln Arg His Leu
            100                 105                 110

Glu Lys Gln His Leu Arg Ile Gln Arg Leu Gln Ser Gln Val Gly Leu
        115                 120                 125

Leu Asp
    130

<210> SEQ ID NO 489
<211> LENGTH: 444
<212> TYPE: DNA
<213> ORGANISM: Macaca fascicularis

<400> SEQUENCE: 489

```
atgcgcggtg ctccgacggc cggagcagcc ctgatgctct gcgtcgccac ggccgtgctg      60
ctgagagctc agggcggccc ggtgcagtcc aagtctccgc gctttgcgtc ctgggacgag     120
atgaatgtcc tggcgcacgg actcctgcag ctaggccagg ggctgcgcga acacgcggag     180
cgcacccgca gtcagctgaa cgcgctggag cggcgcctca cgcttgcgg gtctgcctgc     240
cagggaaccg aggggtccac cgccctcccg ttagcccctg agagccgggt ggaccctgag     300
gtccttcaca gcctgcagac acaactcaag gctcagaaca gcaggatcca gcaactcttc     360
cacaaggtgg cccagcagca gcggcacctg gagaagcagc acctgcgaat tcagcgtctg     420
caaagccagg ttggcctcct ggac                                            444
```

<210> SEQ ID NO 490
<211> LENGTH: 148
<212> TYPE: PRT
<213> ORGANISM: Macaca fascicularis

<400> SEQUENCE: 490

```
Met Arg Gly Ala Pro Thr Ala Gly Ala Ala Leu Met Leu Cys Val Ala
 1               5                  10                  15
Thr Ala Val Leu Leu Arg Ala Gln Gly Gly Pro Val Gln Ser Lys Ser
            20                  25                  30
Pro Arg Phe Ala Ser Trp Asp Glu Met Asn Val Leu Ala His Gly Leu
        35                  40                  45
Leu Gln Leu Gly Gln Gly Leu Arg Glu His Ala Glu Arg Thr Arg Ser
    50                  55                  60
Gln Leu Asn Ala Leu Glu Arg Arg Leu Ser Ala Cys Gly Ser Ala Cys
65                  70                  75                  80
Gln Gly Thr Glu Gly Ser Thr Ala Leu Pro Leu Ala Pro Glu Ser Arg
                85                  90                  95
Val Asp Pro Glu Val Leu His Ser Leu Gln Thr Gln Leu Lys Ala Gln
            100                 105                 110
Asn Ser Arg Ile Gln Gln Leu Phe His Lys Val Ala Gln Gln Gln Arg
        115                 120                 125
His Leu Glu Lys Gln His Leu Arg Ile Gln Arg Leu Gln Ser Gln Val
    130                 135                 140
Gly Leu Leu Asp
145
```

<210> SEQ ID NO 491
<211> LENGTH: 444
<212> TYPE: DNA
<213> ORGANISM: Macaca mulatta

<400> SEQUENCE: 491

```
atgcgcggtg ctccgacggc cggagcagcc ctgatgctct gcgtcgccac ggccgtgctg      60
ctgagagctc agggcggccc ggtgcagtcc aagtctccgc gcttcgcgtc ctgggacgag     120
atgaatgtcc tggcgcacgg actcctgcag ctaggccagg ggctgcgcga acacgcggag     180
cgcacccgca gtcagctgaa cgcgctggag cggcgcctca cgcttgcgg gtctgcctgc     240
cagggaaccg aggggtccac cgccctcccg ttagcccctg agagccgggt ggaccctgag     300
gtccttcaca gcctgcagac acaactcaag gctcagaaca gcaggatcca gcaactcttc     360
cacaaggtgg cccagcagca gcggcacctg gagaagcagc acctgcgaat tcagcgtctg     420
caaagccagg ttggcctcct ggac                                            444
```

<210> SEQ ID NO 492
<211> LENGTH: 148
<212> TYPE: PRT
<213> ORGANISM: Macaca mulatta

<400> SEQUENCE: 492

```
Met Arg Gly Ala Pro Thr Ala Gly Ala Leu Met Leu Cys Val Ala
 1               5                  10                  15

Thr Ala Val Leu Leu Arg Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Asn Ala Leu Glu Arg Arg Leu Ser Ala Cys Gly Ser Ala Cys
65                  70                  75                  80

Gln Gly Thr Glu Gly Ser Thr Ala Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln Arg Leu Gln Ser Gln Val
    130                 135                 140

Gly Leu Leu Asp
145
```

HUMAN ANTIBODIES TO HUMAN ANGIOPOIETIN-LIKE PROTEIN 4

CROSS-REFERENCE TO RELATED APPLICATIONS

This application claims the benefit under 35 U.S.C §119(e) of U.S. provisional application Nos. 61/290,092 filed Dec. 24, 2009; 61/306,359 filed Feb. 19, 2010; 61/328,316 filed Apr. 27, 2010; 61/349,273 filed May 28, 2010; and 61/356,126 filed Jun. 18, 2010, all of which are herein specifically incorporated by reference in their entirety.

FIELD OF THE INVENTION

The present invention is related to human antibodies and antigen-binding fragments of human antibodies that specifically bind human angiopoietin-like protein 4 (hANGPTL4), and therapeutic methods of using those antibodies.

STATEMENT OF RELATED ART

Lipoprotein lipase (LPL) has a central role in lipoprotein metabolism to maintain normal lipoprotein levels in blood and, through tissue specific regulation of its activity, to determine when and in what tissues triglycerides (TG) are unloaded. It has been reported that ANGPTL4 inhibits LPL and retards lipoprotein catabolism, in humans and rodents. ANGPTL4 null mice exhibit a significant decrease in serum TG. Conversely, ANGPTL4 injection into mice produces a rapid increase in circulating lipids and this is at a higher rate than the injection of angiopoietin-like protein 3 (ANGPTL3) (Yoshida et al., 2002, *J Lipid Res* 43:1770-1772). The N-terminal coiled-coil region, not the C-terminal fibrinogen-like domain, of ANGPTL4 is known to be important in the inhibition of LPL activity and, therefore, for the hypertriglyceridemia indication. These observations indicate that inhibition of ANGPTL4 could be beneficial in treating diseases characterized by elevated lipid levels, including primary dyslipidemia and hypertriglyceridemia associated with obesity, metabolic syndrome, type II diabetes, and the like. ANGPTL4 has also been implicated as having a role in angiogenesis and cancer (Galaup et al., 2006, *PNAS* 103(49): 18721-18726; Kim et al., 2000, *Biochem J* 346:603-610; and Ito et al., 2003, *Cancer Res* 63(20):6651-6657).

The nucleic acid and the amino acid sequences of human ANGPTL4 are shown in SEQ ID NOS: 475 and 476, respectively. Antibodies to ANGPTL4 are disclosed in, for example, WO 2006/074228 and WO 2007/109307.

BRIEF SUMMARY OF THE INVENTION

In a first aspect, the invention provides fully human monoclonal antibodies (mAbs) and antigen-binding fragments thereof that specifically bind and neutralize human ANGPTL4 (hANGPTL4) activity.

The antibodies (Abs) can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, *J. Immunol.* 164:1925-1933).

In one embodiment, the invention comprises an antibody or antigen-binding fragment of an antibody comprising a heavy chain variable region (HCVR) selected from the group consisting of SEQ ID NO:2, 18, 22, 26, 42, 46, 50, 66, 70, 74, 90, 94, 98, 114, 118, 122, 138, 142, 146, 162, 166, 170, 186, 190, 194, 210, 214, 218, 234, 238, 242, 258, 262, 266, 282, 286, 290, 306, 310, 314, 330, 334, 338, 354, 358, 362, 378, 382, 386, 402, 406, 410, 426, 430, 434, 450, 454, 458, 466, 468 and 487, or a substantially similar sequence thereof having at least 90%, at least 95%, at least 98% or at least 99% sequence identity. In another embodiment, the antibody or an antigen-binding fragment thereof comprises a HCVR having an amino acid sequence selected from the group consisting of SEQ ID NO:26, 42, 46, 487, 74, 90, 94, 122, 138, 142, 146, 162 and 166. In yet another embodiment, the antibody or fragment thereof comprises a HCVR comprising SEQ ID NO:42, 487, 90, 138 or 162.

In one embodiment, an antibody or antigen-binding fragment of an antibody comprises a light chain variable region (LCVR) selected from the group consisting of SEQ ID NO:10, 20, 24, 34, 44, 48, 58, 68, 72, 82, 92, 96, 106, 116, 120, 130, 140, 144, 154, 164, 168, 178, 188, 192, 202, 212, 216, 226, 236, 240, 250, 260, 264, 274, 284, 288, 298, 308, 312, 322, 332, 336, 346, 356, 360, 370, 380, 384, 394, 404, 408, 418, 428, 432, 442, 452 and 456, or a substantially similar sequence thereof having at least 90%, at least 95%, at least 98% or at least 99% sequence identity.

In another embodiment, the antibody or antigen-binding portion of an antibody comprises a LCVR having an amino acid sequence selected from the group consisting of SEQ ID NO: 34, 44, 48, 82, 92, 96, 130, 140, 144, 154, 164 and 168. In yet another embodiment, the antibody or fragment thereof comprises a LCVR comprising SEQ ID NO:44, 92, 140 or 164.

In further embodiments, the antibody or fragment thereof comprises a HCVR and LCVR (HCVR/LCVR) sequence pair selected from the group consisting of SEQ ID NO:2/10, 18/20, 22/24, 26/34, 42/44, 487/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/394, 466/404 and 468/408. In one embodiment, the antibody or fragment thereof comprises a HCVR and LCVR selected from the amino acid sequence pairs of SEQ ID NO:26/34, 42/44, 487/44, 46/48, 74/82, 90/92, 94/96, 122/130, 138/140, 142/144, 146/154, 162/164 and 166/168. In another embodiment, the antibody or fragment thereof comprises a HCVR/LCVR pair comprising SEQ ID NO:42/44, 487/44, 90/92, 138/140 or 162/164.

In a second aspect, the invention features an antibody or antigen-binding fragment of an antibody comprising a heavy chain complementarity determining region 3 (HCDR3) amino acid sequence selected from the group consisting of SEQ ID NO:8, 32, 56, 80, 104, 128, 152, 176, 200, 224, 248, 272, 296, 320, 344, 368, 392, 416, 440 and 464, or a substantially similar sequence thereof having at least 90%, at least 95%, at least 98% or at least 99% sequence identity; and a light chain CDR3 (LCDR3) amino acid sequence selected from the group consisting of SEQ ID NO:16, 40, 64, 88, 112, 136, 160, 184, 208, 232, 256, 280, 304, 328, 352, 376, 400, 424 and 448, or substantially similar sequences thereof having at least 90%, at least 95%, at least 98% or at least 99% sequence identity. In one embodiment, the antibody or fragment thereof comprises a HCDR3/LCDR3 amino acid sequence pair comprising SEQ ID NO:32/40, 80/88, 128/136 or 152/160. In another embodiment, the antibody or fragment thereof comprises a HCDR3/LCDR3 amino acid sequence pair comprising SEQ ID NO:32/40 or 80/88.

In a further embodiment, the antibody or fragment thereof further comprises a heavy chain CDR1 (HCDR1) amino acid sequence selected from the group consisting of SEQ ID NO:4, 28, 52, 76, 100, 124, 148, 172, 196, 220, 244, 268, 292, 316, 340, 364, 388, 412, 436 and 460, or a substantially similar sequence thereof having at least 90%, at least 95%, at least 98% or at least 99% sequence identity; and a heavy chain CDR2 (HCDR2) amino acid sequence selected from the group consisting of SEQ ID NO:6, 30, 54, 78, 102, 126, 150, 174, 198, 222, 246, 270, 294, 318, 342, 366, 390, 414, 438 and 462, or a substantially similar sequence thereof having at least 90%, at least 95%, at least 98% or at least 99% sequence identity; and optionally further comprises a light chain CDR1 (LCDR1) amino acid sequence selected from the group consisting of SEQ ID NO:12, 36, 60, 84, 108, 132, 156, 180, 204, 228, 252, 276, 300, 324, 348, 372, 396, 420 and 444, or a substantially similar sequence thereof having at least 90%, at least 95%, at least 98% or at least 99% sequence identity; and/or a light chain CDR2 (LCDR2) amino acid sequence selected from the group consisting of SEQ ID NO:14, 38, 62, 86, 110, 134, 158, 182, 206, 230, 254, 278, 302, 326, 350, 374, 398, 422 and 446, or a substantially similar sequence thereof having at least 90%, at least 95%, at least 98% or at least 99% sequence identity.

Alternatively, the invention features an antibody or antigen-binding fragment of an antibody comprising a HCDR1/HCDR2/HCDR3 combination selected from the group consisting of SEQ ID NO:4/6/8, 28/30/32, 52/54/56, 76/78/80, 100/102/104, 124/126/128, 148/150/152, 172/174/176, 196/198/200, 220/222/224, 244/246/248, 268/270/272, 292/294/296, 316/318/320, 340/342/344, 364/366/368, 388/390/392, 412/414/416, 436/438/440 and 460/462/464; and/or a LCDR1/LCDR2/LCDR3 combination selected from the group consisting of SEQ ID NO:12/14/16, 36/38/40, 60/62/64, 84/86/88, 108/110/112, 132/134/136, 156/158/160, 180/182/184, 204/206/208, 228/230/232, 252/254/256, 276/278/280, 300/302/304, 324/326/328, 348/350/352, 372/374/376, 396/398/400, 420/422/424 and 444/446/448.

In one embodiment, the HCDR1, HCDR2 and HCDR3 are selected from the group consisting of SEQ ID NO:28/30/32, 76/78/80, 124/126/128, and 148/150/152; and/or the LCDR1, LCDR2 and LCDR3 are selected from the group consisting of SEQ ID NO:36/38/40, 84/86/88, 132/134/136, and 156/158/160. In yet another embodiment, the heavy and light chain CDR amino acid sequences comprise a CDR sequence combination selected from the group consisting of SEQ ID NO:28/30/32/36/38/40, 76/78/80/84/86/88, 124/126/128/132/134/136, and 148/150/152/156/158/160. In yet another embodiment, the antibody or antigen-binding fragment thereof comprises heavy and light chain CDR sequences of SEQ ID NO: 28/30/32/36/38/40, or 76/78/80/84/86/88.

In a related embodiment, the invention comprises an antibody or antigen-binding fragment of an antibody which specifically binds hANGPTL4, wherein the antibody or fragment thereof comprises heavy and light chain CDR domains contained within HCVR/LCVR pairs selected from the group consisting of SEQ ID NO: 2/10, 18/20, 22/24, 26/34, 42/44, 487/44, 46/48, 50/58, 66/68, 70/72, 74/82, 90/92, 94/96, 98/106, 114/116, 118/120, 122/130, 138/140, 142/144, 146/154, 162/164, 166/168, 170/178, 186/188, 190/192, 194/202, 210/212, 214/216, 218/226, 234/236, 238/240, 242/250, 258/260, 262/264, 266/274, 282/284, 286/288, 290/298, 306/308, 310/312, 314/322, 330/332, 334/336, 338/346, 354/356, 358/360, 362/370, 378/380, 382/384, 386/394, 402/404, 406/408, 410/418, 426/428, 430/432, 434/442, 450/452, 454/456, 458/394, 466/404 and 468/408. Methods and techniques for identifying CDRs within HCVR and LCVR amino acid sequences are known in the art and can be applied to identify CDRs within the specified HCVR and/or LCVR amino acid sequences disclosed herein. Conventional definitions that can be applied to identify the boundaries of CDRs include the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody. In one embodiment, the antibody or fragment thereof comprises CDR sequences contained within a HCVR and LCVR pair selected from the group consisting of the amino acid sequence pairs of SEQ ID NO: 26/34, 42/44, 487/44, 46/48, 74/82, 90/92, 94/96, 122/130, 138/140, 142/144, 146/154, 162/164 and 166/168. In another embodiment, the antibody or fragment thereof comprises CDR sequences contained within the HCVR and LCVR sequence pair of SEQ ID NO: 42/44, 487/44, 90/92, 138/140 or 162/164.

In another related embodiment, the invention provides an antibody or antigen-binding fragment thereof that competes for specific binding to hANGPTL4 with an antibody or antigen-binding fragment comprising heavy and light chain CDR sequences of SEQ ID NO: 28/30/32/36/38/40, 76/78/80/84/86/88, 124/126/128/132/134/136, or 148/150/152/156/158/160. In one embodiment, the antibody or antigen-binding fragment of the invention competes for specific binding to hANGPTL4 with an antibody comprising a HCVR/LCVR sequence pair of SEQ ID NO:42/44, 487/44, 90/92, 138/140, or 162/164.

In another related embodiment, the invention provides an antibody or antigen-binding fragment thereof that binds the same epitope on hANGPTL4 that is recognized by an antibody or fragment thereof comprising heavy and light chain CDR sequences of SEQ ID NO: 28/30/32/36/38/40, 76/78/80/84/86/88, 124/126/128/132/134/136, or 148/150/152/156/158/160. In one embodiment, the antibody or antigen-binding fragment of the invention recognizes the epitope on hANGPTL4 that is recognized by an antibody comprising a HCVR/LCVR sequence pair of SEQ ID NO:42/44, 487/44, 90/92, 138/140, or 162/164.

In a third aspect, the invention provides nucleic acid molecules encoding anti-ANGPTL4 antibodies or fragments thereof, in particular, those described above. Recombinant expression vectors carrying the nucleic acids of the invention, and host cells, e.g., bacterial cells, such as *E. coli*, or mammalian cells, such as CHO cells, into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 21, 25, 41, 45, 49, 65, 69, 73, 89, 93, 97, 113, 117, 121, 137, 141, 145, 161, 165, 169, 185, 189, 193, 209, 213, 217, 233, 237, 241, 257, 261, 265, 281, 285, 289, 305, 309, 313, 329, 333, 337, 353, 357, 361, 377, 381, 385, 401, 405, 409, 425, 429, 433, 449, 453, 457, 465, 467 and 486, or a substantially identical sequence having at least 90%, at least 95%, at least 98%, or at least 99% homology thereof. In another embodiment, the antibody or fragment thereof comprises a HCVR encoded by a nucleic acid sequence selected from the group consisting of SEQ ID NO: 25, 41, 45, 73, 89, 93, 121, 137, 141, 145, 161, 165 and 486. In yet another embodiment, the antibody or fragment thereof comprises a HCVR encoded by the nucleic acid sequence of SEQ ID NO: 41, 89, 137, 161 or 486.

In one embodiment, an antibody or antigen-binding fragment thereof comprises a LCVR encoded by a nucleic acid sequence selected from the group consisting of SEQ ID NO: 9, 19, 23, 33, 43, 47, 57, 67, 71, 81, 91, 95, 105, 115, 119, 129, 139, 143, 153, 163, 167, 177, 187, 191, 201, 211, 215, 225, 235, 239, 249, 259, 263, 273, 283, 287, 297, 307, 311, 321, 331, 335, 345, 355, 359, 369, 379, 383, 393, 403, 407, 417, 427, 431, 441, 451 and 455, or a substantially identical sequence having at least 90%, at least 95%, at least 98%, or at least 99% homology thereof. In another embodiment, the antibody or fragment thereof comprises a LCVR encoded by a nucleic acid sequence selected from the group consisting of SEQ ID NO: 33, 43, 47, 81, 91, 95, 129, 139, 143, 153, 163 and 167. In yet another embodiment, the antibody or fragment thereof comprises a LCVR encoded by the nucleic acid sequence of SEQ ID NO: 43, 91, 139 or 163.

In further embodiments, the antibody or fragment thereof comprises a HCVR and LCVR (HCVR/LCVR) sequence pair encoded by a nucleic acid sequence pair selected from the group consisting of SEQ ID NO:1/9, 17/19, 21/23, 25/33, 41/43, 486/43, 45/47, 49/57, 65/67, 69/71, 73/81, 89/91, 93/95, 97/105, 113/115, 117/119, 121/129, 137/139, 141/143, 145/153, 161/163, 165/167, 169/177, 185/187, 189/191, 193/201, 209/211, 213/215, 217/225, 233/235, 237/239, 241/249, 257/259, 261/263, 265/273, 281/283, 285/287, 289/297, 305/307, 309/311, 313/321, 329/331, 333/335, 337/345, 353/355, 357/359, 361/369, 377/379, 381/383, 385/393, 401/403, 405/407, 409/417, 425/427, 429/431, 433/441, 449/451, 453/455, 457/393, 465/403 and 467/407. In one embodiment, the antibody or fragment thereof comprises a HCVR/LCVR sequence pair encoded by a nucleic acid sequence pair selected from the group consisting of SEQ ID NO: 25/33, 41/43, 486/43, 45/47, 73/81, 89/91, 93/95, 121/129, 137/139, 141/143, 145/153, 161/163 and 165/167. In yet another embodiment, the antibody or fragment thereof comprises a HCVR/LCVR pair encoded by a nucleic acid sequence pair of SEQ ID NO:41/43, 486/43, 89/91, 137/139 or 161/163.

In one embodiment, the invention features an antibody or antigen-binding fragment of an antibody comprising a HCDR3 domain encoded by a nucleotide sequence selected from the group consisting of SEQ ID NO:7, 31, 55, 79, 103, 127, 151, 175, 199, 223, 247, 271, 295, 319, 343, 367, 391, 415, 439 and 463, or a substantially identical sequence having at least 90%, at least 95%, at least 98%, or at least 99% homology thereof; and a LCDR3 domain encoded by a nucleotide sequence selected from the group consisting of SEQ ID NO: 15, 39, 63, 87, 111, 135, 159, 183, 207, 231, 255, 279, 303, 327, 351, 375, 399, 423 and 447, or a substantially identical sequence having at least 90%, at least 95%, at least 98%, or at least 99% homology thereof. In another embodiment, the antibody or fragment thereof comprises a HCDR3 and LCDR3 sequence pair encoded by the nucleic acid sequence pair of SEQ ID NO: 31/39, 79/87, 127/135 or 151/159. In yet another embodiment, the antibody or fragment thereof comprises a HCDR3 and LCDR3 sequence pair encoded by the nucleic acid sequence pair of SEQ ID NO:31/39 or 79/87.

In a further embodiment, the antibody or fragment thereof further comprises a HCDR1 domain encoded by a nucleotide sequence selected from the group consisting of SEQ ID NO: 3, 27, 51, 75, 99, 123, 147, 171, 195, 219, 243, 267, 291, 315, 339, 363, 387, 411, 435 and 459, or a substantially identical sequence having at least 90%, at least 95%, at least 98%, or at least 99% homology thereof; and a HCDR2 domain encoded by a nucleotide sequence selected from the group consisting of SEQ ID NO:5, 29, 53, 77, 101, 125, 149, 173, 197, 221, 245, 269, 293, 317, 341, 365, 389, 413, 437 and 461, or a substantially identical sequence having at least 90%, at least 95%, at least 98%, or at least 99% homology thereof; and optionally further comprises a LCDR1 domain encoded by a nucleotide sequence selected from the group consisting of SEQ ID NO: 11, 35, 59, 83, 107, 131, 155, 179, 203, 227, 251, 275, 299, 323, 347, 371, 395, 419 and 443, or a substantially identical sequence having at least 90%, at least 95%, at least 98%, or at least 99% homology thereof; and/or a LCDR2 domain encoded by a nucleotide sequence selected from the group consisting of SEQ ID NO: 13, 37, 61, 85, 109, 133, 157, 181, 205, 229, 253, 277, 301, 325, 349, 373, 397, 421 and 445, or a substantially identical sequence having at least 90%, at least 95%, at least 98%, or at least 99% homology thereof.

Alternatively, the invention features an antibody or antigen-binding fragment of an antibody comprising a HCDR1/HCDR2/HCDR3 combination encoded by a nucleotide sequence combination selected from the group consisting of SEQ ID NO:3/5/7, 27/29/31, 51/53/55, 75/77/79, 99/101/103, 123/125/127, 147/149/151, 171/173/175, 195/197/199, 219/221/223, 243/245/247, 267/269/271, 291/293/295, 315/317/319, 339/341/343, 363/365/367, 387/389/391, 411/413/415, 435/437/439 and 459/461/463; and/or a LCDR1/LCDR2/LCDR3 combination encoded by a nucleotide sequence combination selected from the group consisting of SEQ ID NO:11/13/15, 35/37/39, 59/61/63, 83/85/87, 107/109/111, 131/133/135, 155/157/159, 179/181/183, 203/205/207, 227/229/231, 251/253/255, 275/277/279, 299/301/303, 323/325/327, 347/349/351, 371/373/375, 395/397/399, 419/421/423 and 443/445/447.

In one embodiment, the HCDR1, HCDR2 and HCDR3 are encoded by a nucleotide sequence combination selected from the group consisting of SEQ ID NO:27/29/31, 75/77/79, 123/125/127, and 147/149/151; and/or the LCDR1, LCDR2 and LCDR3 are encoded by a nucleotide sequence combination selected from the group consisting of SEQ ID NO:35/37/39, 83/85/87, 131/133/135, and 155/157/159. In yet another embodiment, the antibody or fragment thereof comprises heavy and light chain CDR sequences encoded by a nucleotide sequence combination selected from the group consisting of SEQ ID NO: 27/29/31/35/37/39; 75/77/79/83/85/87; 123/125/127/131/133/135; and 147/149/151/155/157/159. In another embodiment, the antibody or antigen-binding portion thereof comprises heavy and light chain CDR sequences encoded by the nucleotide sequence combination of SEQ ID NO: 27/29/31/35/37/39; or 75/77/79/83/85/87.

In a fourth aspect, the invention features an isolated antibody or antigen-binding fragment of an antibody that specifically binds hANGPTL4, comprising a HCDR3 and a LCDR3, wherein the HCDR3 comprises an amino acid sequence of the formula $X^1$-$X^2$-$X^3$-$X^4$-$X^5$-$X^6$-$X^7$-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$ (SEQ ID NO:471) wherein $X^1$ is Ala, $X^2$ is Arg or Lys, $X^3$ is Gly or Glu, $X^4$ is Gly, Asp or absent, $X^5$ is Asp or absent, $X^6$ is Leu, Arg or absent, $X^7$ is Arg or Ser, $X^8$ is Phe, Gly or Arg, $X^9$ is Leu, His or Asn, $X^{19}$ is Asp, Pro or Tyr, X" is Trp, Tyr or Phe, $X^{12}$ is Leu, Phe, Val or Asp, $X^{13}$ is Ser, Tyr or Gly, $X^{14}$ is Ser, Tyr or Asp, $X^{15}$ is Tyr, $X^{16}$ is Phe or Gly, $X^{17}$ is Leu or absent, $X^{18}$ is Asp, $X^{19}$ is Tyr, Val or Phe, and $X^{20}$ is Trp; and the LCDR3 comprises an amino acid sequence of the formula $X^1$-$X^2$-$X^3$-$X^4$-$X^5$-$X^6$-$X^7$-$X^8$-$X^9$-$X^{10}$ (SEQ ID NO:474) wherein $X^1$ is Gln, $X^2$ is Asn or Gln, $X^3$ is Tyr or Leu, $X^4$ is Asn, His, Ser or Asp, $X^5$ is Thr or Ser, $X^6$ is Ala or Tyr, $X^7$ is Pro, Ser or Phe, $X^8$ is Leu or Arg, $X^9$ is Thr, and $X^{10}$ is Phe.

In a further embodiment, the antibody or fragment thereof further comprises a HCDR1 sequence comprising an amino acid sequence of the formula $X^1$-$X^2$-$X^3$-$X^4$-$X^5$-$X^6$-$X^7$-$X^8$ (SEQ ID NO:469), wherein $X^1$ is Gly, $X^2$ is Gly or Phe, $X^3$ is Ser or Thr, $X^4$ is Phe, $X^5$ is Ser, $X^6$ is Ile, Ser or Thr, $X^7$ is His or Tyr, and $X^8$ is His, Gly or Asp; a HCDR2 sequence comprising an amino acid sequence of the formula $X^1$-$X^2$-$X^3$-$X^4$-$X^5$-$X^6$-$X^7$-$X^8$ (SEQ ID NO:470), wherein $X^1$ is Ile, $X^2$ is Asn, Ser or Gly, $X^3$ is His, Phe, Ser or Val, $X^4$ is Arg, Asp or Ala, $X^5$ is Gly, $X^6$ is Gly or absent, $X^7$ is Ser, Asn or Asp, and $X^8$ is Thr or Lys; a LCDR1 sequence comprising an amino acid sequence of the formula $X^1$-$X^2$-$X^3$-$X^4$-$X^5$-$X^6$ (SEQ ID NO:472) wherein $X^1$ is Gln, $X^2$ is Gly or Ser, $X^3$ is Ile, $X^4$ is Ser or Asn, $X^5$ is Asp, Ser or Arg, and $X^6$ is Tyr or Trp; and a LCDR2 sequence comprising an amino acid sequence of the formula $X^1$-$X^2$-$X^3$ (SEQ ID NO:473) wherein $X^1$ is Ala or Lys, $X^2$ is Ala, and $X^3$ is Ser. The sequence alignments of H1H268P, H1H284P, H1H291P and H1H292P monoclonal antibodies are shown in FIG. 1 (HCVR) and FIG. 2 (LCVR).

In a fifth aspect, the invention features a human anti-ANGPTL4 antibody or antigen-binding fragment thereof comprising a heavy chain variable region (HCVR) encoded by nucleotide sequence segments derived from $V_H$, $D_H$ and $J_H$ germline sequences, and a light chain variable region (LCVR) encoded by nucleotide sequence segments derived from $V_K$ and $J_K$ germline sequences, wherein the HCVR and the LCVR are encoded by nucleotide sequence segments derived from a germline gene combination selected from the group consisting of: (i) $V_H$3-30, $D_H$5-12, $J_H$6, $V_K$1-9 and $J_K$4; (ii) $V_H$4-34, $D_H$3-3, $J_H$4, $V_K$1-27 and $J_K$4; and (iii) $V_H$3-13, $D_H$1-26, $J_H$4, $V_K$1-5 and $J_K$1.

In a sixth aspect, the invention features an antibody or antigen-binding fragment thereof that specifically binds to hANGPTL4 with an equilibrium dissociation constant ($K_D$) of about 1 nM or less, as measured by surface plasmon resonance assay (for example, BIACORE™). In certain embodiments, the antibody of the invention exhibits a $K_D$ of about 500 pM or less; about 400 pM or less; about 300 pM or less; about 200 pM or less; about 150 pM or less; about 100 pM or less; or about 50 pM or less.

In a seventh aspect, the present invention provides an anti-hANGPTL4 antibody or antigen-binding fragment thereof that binds hANGPTL4 protein of SEQ ID NO:476, but does not cross-react with a related protein, such as a human angiopoietin-like protein 3 (hANGPTL3; SEQ ID NO:485), as determined by, for example, ELISA, surface plasmon resonance assay, or LUMINEX® XMAP® Technology, as described herein. ANGPTL3 is another secreted protein that is known to reduce LPL activity and has an N-terminal coiled-coil region and a C-terminal fibrinogen-like domain (Ono et al., 2003, *J Biol Chem* 43:41804-41809). In related embodiments, the invention provides an anti-hANGPTL4 antibody or antigen binding fragment thereof that binds a hANGPTL4 protein and cross-reacts with a hANGPTL3 protein. In certain embodiments, the binding affinity of the hANGPTL4 antibody or fragment thereof to hANGPTL3 protein is about 75% or less, or about 50% or less, of the binding affinity of the antibody or fragment to the hANGPTL4 protein. In another related embodiment, the invention provides an anti-hANGPTL4 antibody or antigen binding fragment thereof that does not cross-react with mouse ANGPTL4 (mANGPTL4: SEQ ID NO:478) but does cross-react with cynomolgus monkey (*Macaca fascicularis*; the amino acid sequence of the N-terminal 1-148 residues and the encoding DNA sequences are shown as SEQ ID NOS:490 and 489, respectively) and/or rhesus monkey (*Macaca mulatta*; the amino acid sequence of the N-terminal 1-148 residues and the encoding DNA sequences are shown as SEQ ID NOS:492 and 491, respectively) ANGPTL4.

The invention encompasses anti-hANGPTL4 antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, removal of N-glycosylation site may reduce undesirable immune reactions against the therapeutic antibodies, or increase affinities of the antibodies. In yet other applications, modification of galactosylation can be made in order to modify complement dependent cytotoxicity (CDC).

In an eighth aspect, the invention features a pharmaceutical composition comprising a recombinant human antibody or fragment thereof which specifically binds hANGPTL4 and a pharmaceutically acceptable carrier. In one embodiment, the invention features a composition which is a combination of an antibody or antigen-binding fragment thereof of the invention, and a second therapeutic agent. The second therapeutic agent may be one or more of any agent such as (1) 3-hydroxy-3-methylglutaryl-coenzyme A (HMG-CoA) reductase inhibitors, such as cerivastatin, atorvastatin, simvastatin, pitavastatin, rosuvastatin, fluvastatin, lovastatin, pravastatin, and the like; (2) inhibitors of cholesterol uptake and/or bile acid re-absorption; (3) niacin, which increases lipoprotein catabolism; (4) fibrates or amphipathic carboxylic acids, which reduce low-density lipoprotein (LDL) level, improve high-density lipoprotein (HDL) and TG levels, and reduce the number of non-fatal heart attacks; and (5) activators of the LXR transcription factor that plays a role in cholesterol elimination such as 22-hydroxycholesterol, or fixed combinations such as ezetimibe plus simvastatin; a statin with a bile resin (e.g., cholestyramine, colestipol, colesevelam), a fixed combination of niacin plus a statin (e.g., niacin with lovastatin); or with other lipid lowering agents such as omega-3-fatty acid ethyl esters (for example, omacor). Furthermore, the second therapeutic agent can be one or more other inhibitors of ANGPTL4 as well as inhibitors of other molecules, such as ANGPTL3, ANGPTL5, ANGPTL6 and proprotein convertase subtilisin/kexin type 9 (PCSK9), which are involved in lipid metabolism, in particular, cholesterol and/or triglyceride homeostasis. Inhibitors of these molecules include small molecules and antibodies that specifically bind to these molecules and block their activity.

In related embodiments, the second therapeutic agent may be one or more anti-cancer agents, such as chemotherapeutic agents, anti-angiogenic agents, growth inhibitory agents, cytotoxic agents, apoptotic agents, and other agents well known in the art to treat cancer or other proliferative diseases or disorders, as well as other therapeutic agents, such as analgesics, anti-inflammatory agents, including non-steroidal anti-inflammatory drugs (NSAIDS), such as Cox-2 inhibitors, and the like, so as to ameliorate and/or reduce the symptoms accompanying the underlying cancer/tumor.

In a ninth aspect, the invention features methods for inhibiting hANGPTL4 activity using the anti-hANGPTL4 antibody or antigen-binding portion of the antibody of the invention, wherein the therapeutic methods comprise administering a therapeutically effective amount of a pharmaceutical composition comprising an antibody or antigen-binding fragment of an antibody of the invention and, optionally one or more additional therapeutic agents described above. The disease or disorder treated is any disease or condition which is improved, ameliorated, inhibited or prevented, or its occurrence rate reduced compared to that without anti-hANGPTL4 antibody treatment (e.g., ANGPTL4-mediated diseases or disorders), by removal, inhibition or reduction of ANGPTL4 activity. Examples of diseases or disorders treatable by the methods of the invention include, but are not limited to, those involving lipid metabolism, such as hyperlipidemia, hyperlipoproteinemia and dyslipidemia, including atherogenic dyslipidemia, diabetic dyslipidemia, hypertriglyceridemia, including severe hypertriglyceridemia with TG>1000 mg/dL, hypercholesterolemia, chylomicronemia, mixed dyslipidemia (obesity, metabolic syndrome, diabetes, etc.), lipodystrophy, lipoatrophy, and the like, which are caused by, for example, decreased LPL activity and/or LPL deficiency, decreased LDL receptor activity and/or LDL receptor deficiency, altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, life style, and the like. The methods of the invention can also prevent or treat diseases or disorders associated with or resulting from hyperlipidemia, hyperlipoproteinemia, and/or dyslipidemia, including, but not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes; obesity, and the like.

Other examples of diseases or disorders treatable by the methods of the invention include cancer/tumor as well as non-neoplastic angiogenesis-associated diseases or disorders, including ocular angiogenic diseases or disorders, such as age-related macular degeneration, central retinal vein occlusion or branch retinal vein occlusion, diabetic retinopathy, retinopathy of prematurity, and the like, inflammatory diseases or disorders, such as arthritis, rheumatoid arthritis (RA), psoriasis, and the like.

Other embodiments will become apparent from a review of the ensuing detailed description.

BRIEF DESCRIPTION OF THE FIGURE

FIG. 1 shows a sequence alignment of heavy chain variable regions (HCVR) of antibodies H1H268P, H1H284P, H1H291P AND H1H292P.

FIG. 2 shows a sequence alignment of light chain variable regions (LCVR) of antibodies H1H268P, H1H284P, H1H291P AND H1H292P.

Figure 3:
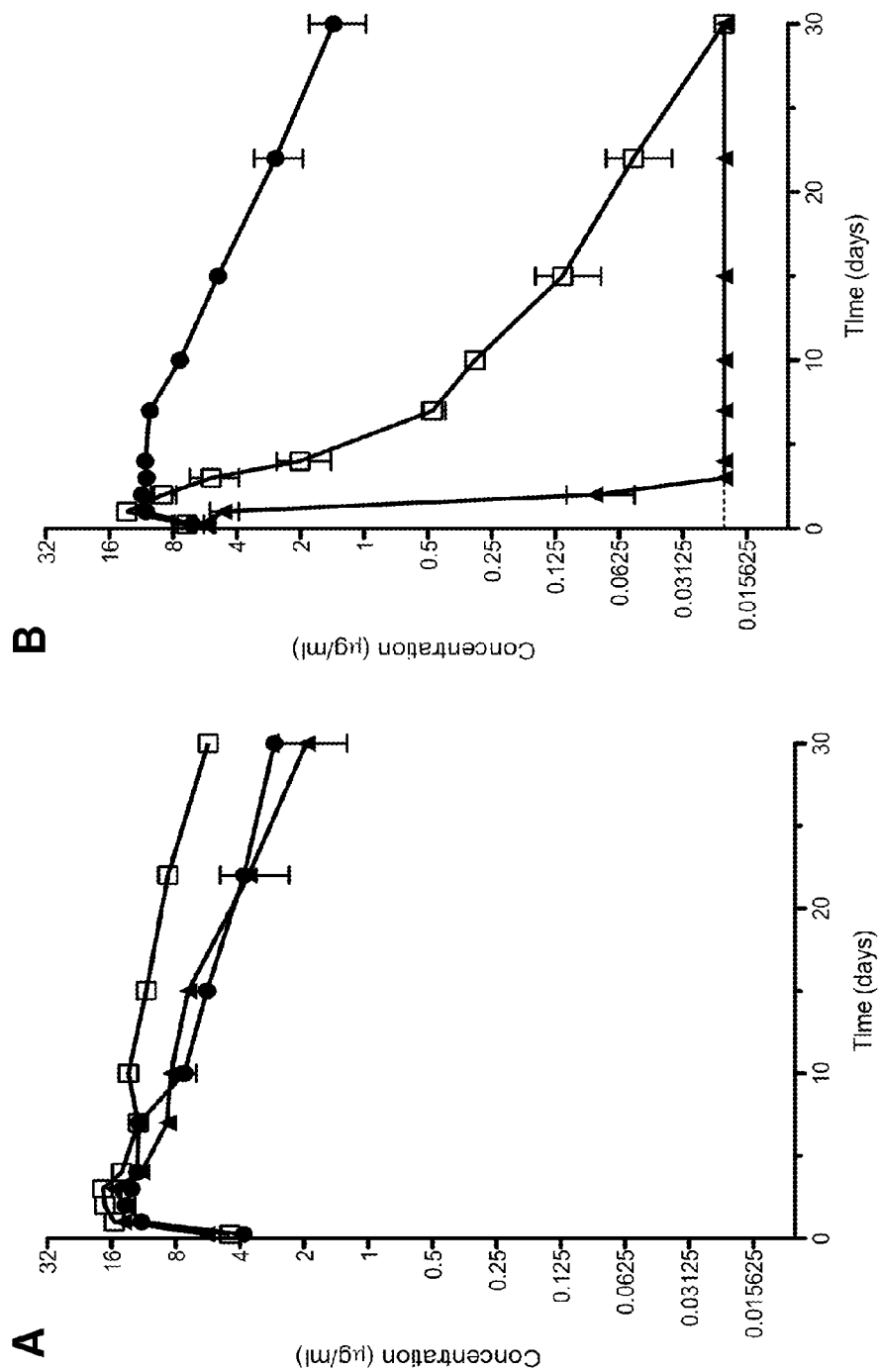
FIGS. 3A and 3B show the pharmacokinetic clearance of anti-ANGPTL4 antibodies in wild-type mice (FIG. 3A) and in transgenic mice expressing human ANGPTL4 [hAngptl4 (+/+) mice; or "humanized ANGPTL4 mice"] (FIG. 3B). H4H268P2 (□); H4H284P (▲); and hIgG4 control (●).

Error bars in all graphs indicate mean±SEM.

DETAILED DESCRIPTION

Before the present invention is described in detail, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

DEFINITIONS

The term "human angiopoietin-like protein 4" or "hANGPTL4", as used herein, refers to hANGPTL4 having the nucleic acid sequence shown in SEQ ID NO:475 and the amino acid sequence of SEQ ID NO:476, or a biologically active fragment thereof.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (HCVR) and a heavy chain constant region ($C_H$; comprised of domains $C_H1$, $C_H2$ and $C_H3$). Each light chain is comprised of a light chain variable region (LCVR) and a light chain constant region ($C_L$). The HCVR and LCVR can be further subdivided into regions of hypervariability, termed complementarity determining regions (CDR), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, and FR4.

Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example, residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The fully-human anti-hANGPTL4 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residues(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residues of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-ANGPTL4 antibodies comprising variants of any of the HCVR, LCVR, and/or CDR amino acid sequences disclosed herein having one or more conservative substitutions. For example, the present invention includes anti-ANGPTL4 antibodies having HCVR, LCVR, and/or CDR amino acid sequences with, e.g., 10 or fewer, 8 or fewer, 6 or fewer, 4 or fewer, 2 or 1, conservative amino acid substitution(s) relative to any of the HCVR, LCVR, and/or CDR amino acid sequences disclosed herein. In one embodiment, a HCVR comprises the amino acid sequence of SEQ ID NO:487 with 10 or fewer conservative amino acid substitutions therein. In another embodiment, a HCVR comprises the amino acid sequence of SEQ ID NO:487 with 8 or fewer conservative amino acid substitutions therein. In another embodiment, a HCVR comprises the amino acid sequence of SEQ ID NO:487 with 6 or fewer conservative amino acid substitutions therein. In another embodiment, a HCVR comprises the amino acid sequence of SEQ ID NO:487 with 4 or fewer conservative amino acid substitutions therein. In yet another embodiment, a HCVR comprises the amino acid sequence of SEQ ID NO:487 with 2 or 1 conservative amino acid substitution(s) therein. In one embodiment, a LCVR comprises the amino acid sequence of SEQ ID NO:44 with 10 or fewer conservative amino acid substitutions therein. In another embodiment, a LCVR comprises the amino acid sequence of SEQ ID NO:44 with 8 or fewer conservative amino acid substitutions therein. In another embodiment, a LCVR comprises the amino acid sequence of SEQ ID NO:44 with 6 or fewer conservative amino acid substitutions therein. In another embodiment, a LCVR comprises the amino acid sequence of SEQ ID NO:44 with 4 or fewer conservative amino acid substitutions therein. In yet another embodiment, a LCVR comprises the amino acid sequence of SEQ ID NO:44 with 2 or 1 conservative amino acid substitution(s) therein.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-display antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR)). Other engineered molecules, such as diabodies, triabodies, tetrabodies and minibodies, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (X) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments, antibody or antibody fragments of the invention may be conjugated to a therapeutic moiety ("immunoconjugate"), such as a cytotoxin, a chemotherapeutic drug, an immunosuppressant or a radioisotope.

The term "specifically binds," or the like, means that an antibody or antigen-binding fragment thereof forms a complex with an antigen that is relatively stable under physiological conditions. Specific binding can be characterized by an equilibrium dissociation constant ($K_D$) of about $1 \times 10^{-6}$ M or less (i.e., a smaller $K_D$ denotes a tighter binding). Methods for determining whether two molecules specifically bind are well known in the art and include, for example, equilibrium dialysis, surface plasmon resonance, and the like. An isolated antibody that specifically binds hANGPTL4 may, however, exhibit cross-reactivity to other antigens, such as ANGPTL4 molecules from other species, for example, cynomolgus monkey ANGPTL4, and/or hANGPTL3 having the amino acid sequence of SEQ ID NO:485. Moreover, multi-specific antibodies (e.g., bispecifics) that bind to hANGPTL4 and one or more additional antigens are nonetheless considered antibodies that "specifically bind" hANGPTL4, as used herein.

The term "high affinity" antibody refers to those antibodies having a binding affinity to hANGPTL4, expressed as $K_D$, of about $1 \times 10^{-9}$ M or less, about $0.5 \times 10^{-9}$ M or less, about $0.25 \times 10^{-9}$ M or less, about $1 \times 10^{-10}$ M or less, or about $0.5 \times 10^{-10}$ M or less, as measured by surface plasmon resonance, e.g., BIACORE™ or solution-affinity ELISA.

The term "$K_D$", as used herein, is intended to refer to the equilibrium dissociation constant of a particular antibody-antigen interaction.

By the term "slow off rate", "Koff" or "$k_d$" is meant an antibody that dissociates from hANGPTL4 with a rate constant of $1 \times 10^{-3}$ s$^{-1}$ or less, preferably $1 \times 10^{-4}$s$^{-1}$ or less, as determined by surface plasmon resonance, e.g., BIACORE™

By the term "intrinsic affinity constant" or "$k_a$" is meant an antibody that associates with hANGPTL4 at a rate constant of about $1 \times 10^{-3}$ M$^{-1}$s$^{-1}$ or higher, as determined by surface plasmon resonance, e.g., BIACORE™

An "isolated antibody", as used herein, is intended to refer to an antibody that is substantially free of other mAbs having different antigenic specificities (e.g., an isolated antibody that specifically binds hANGPTL4 is substantially free of mAbs that specifically bind antigens other than hANGPTL4). An isolated antibody that specifically binds hANGPTL4 may, however, have cross-reactivity to other antigens, such as ANGPTL4 molecules from other species, such as cynomolgus monkey, and/or other related proteins, such as human ANGPTL3.

A "neutralizing antibody", as used herein (or an "antibody that neutralizes ANGPTL4 activity"), is intended to refer to an antibody whose binding to ANGPTL4 results in inhibition of at least one biological activity of ANGPTL4. This inhibition of the biological activity of ANGPTL4 can be assessed by measuring one or more indicators of ANGPTL4 biological activity by one or more of several standard in vitro or in vivo assays known in the art (also see examples below).

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402.

By the phrase "therapeutically effective amount" is meant an amount that produces the desired effect for which it is administered. The exact amount will depend on the purpose of the treatment, the age and the size of a subject treated, the route of administration, and the like, and will be ascertainable by one skilled in the art using known techniques (see, for example, Lloyd (1999) The Art, Science and Technology of Pharmaceutical Compounding).

Preparation of Human Antibodies

Methods for generating human antibodies in transgenic mice are known in the art. Any such known methods can be used in the context of the present invention to make human antibodies that specifically bind to ANGPTL4.

Using VELOCIMMUNE™ technology or any other known method for generating monoclonal antibodies, high affinity chimeric antibodies to ANGPTL4 are initially isolated having a human variable region and a mouse constant region. As in the experimental section below, the antibodies are characterized and selected for desirable characteristics, including affinity, selectivity, epitope, and the like.

In general, the antibodies of the instant invention possess very high affinities, typically possessing $K_D$ of from about $10^{-12}$ M through about $10^{-9}$ M, when measured by binding to antigen either immobilized on solid phase or in solution phase. The mouse constant regions are replaced with desired human constant regions, for example, wild-type IgG1 (SEQ ID NO:481) or IgG4 (SEQ ID NO:482), or modified IgG1 or IgG4 (for example, SEQ ID NO:483), to generate the fully human antibodies of the invention. While the constant region selected may vary according to specific use, high affinity antigen-binding and target specificity characteristics of the antibodies reside in the variable region.

Epitope Mapping and Related Technologies

To screen for antibodies that bind to a particular epitope, a routine cross-blocking assay such as that described in *Antibodies*, Harlow and Lane (Cold Spring Harbor Press, Cold Spring Harb., N.Y.) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496).

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (US 2004/0101920). Each category may reflect a unique epitope either distinctly different from or partially overlapping with epitope represented by another category. This technology allows rapid filtering of genetically identical mAbs, such that characterization can be focused on genetically distinct mAbs.

When applied to hybridoma screening, MAP may facilitate identification of rare hybridoma clones that produce mAbs having the desired characteristics. MAP may be used to sort the anti-ANGPTL4 mAbs of the invention into groups of mAbs binding different epitopes.

ANGPTL4 contains an amino-terminal coiled-coil domain and a carboxyl-terminal fibrinogen like domain and the full-length ANGPTL4 protein forms an oligomer held by intermolecular disulfide bonds (Ge et al., 2004, *J Bio Chem* 279 (3):2038-2045). It has been reported that the N-terminal coiled-coil domain mediates ANGPTL4's oligomerization (Ge et al., supra) and is also important in the inhibition of LPL activity (Ge et al., 2005, *J Lipid Res* 46:1484-1490; and Ono et al., 2003, *J Biol Chem* 278:41804-41809). Thus, in certain embodiments, the anti-hANGPTL4 antibody or antigen-binding fragment of an antibody binds an epitope within the N-terminal coiled-coil domain (residues 1-123) of hANGPTL4 (SEQ ID NO:476). In certain embodiments, anti-hANGPTL4 antibody or fragment thereof binds an epitope within the region from about residue 1 to about residue 25, from about residue 25 to about residue 50, from about residue 50 to about residue 75, from about residue 75 to about residue 100, from about residue 100 to about residue 125, from about residue 125 to about residue 150, of hANGPTL4 (SEQ ID NO:476). In some embodiments, the antibody or antibody fragment binds an epitope which includes more than one of the enumerated epitopes within the N-terminal coiled-coil domain of hANGPTL4. In other embodiments, hANGPTL4 antibody or fragment thereof binds one or more fragments of hANGPTL4, for example, a fragment from residues 26 to 406, from residues 26 to 148, from residues 34 to 66, and/or residues 165 to 406, of SEQ ID NO:476.

The present invention includes hANGPTL4 antibodies that bind to the same epitope as any of the specific exemplary antibodies described herein. Likewise, the present invention also includes anti-hANGPTL4 antibodies that compete for binding to hANGPTL4 or a hANGPTL4 fragment with any of the specific exemplary antibodies described herein.

One can easily determine whether an antibody binds to the same epitope as, or competes for binding with, a reference anti-hANGPTL4 antibody by using routine methods known in the art. For example, to determine if a test antibody binds to the same epitope as a reference anti-hANGPTL4 antibody of the invention, the reference antibody is allowed to bind to a hANGPTL4 protein or peptide under saturating conditions. Next, the ability of a test antibody to bind to the hANGPTL4 molecule is assessed. If the test antibody is able to bind to hANGPTL4 following saturation binding with the reference anti-hANGPTL4 antibody, it can be concluded that the test antibody binds to a different epitope than the reference anti-hANGPTL4 antibody. On the other hand, if the test antibody is not able to bind to the hANGPTL4 molecule following saturation binding with the reference anti-hANGPTL4 antibody, then the test antibody may bind to the same epitope as the epitope bound by the reference anti-hANGPTL4 antibody of the invention.

To determine if an antibody competes for binding with a reference anti-hANGPTL4 antibody, the above-described binding methodology is performed in two orientations: In a first orientation, the reference antibody is allowed to bind to a hANGPTL4 molecule under saturating conditions followed by assessment of binding of the test antibody to the hANGPTL4 molecule. In a second orientation, the test antibody is allowed to bind to a hANGPTL4 molecule under saturating conditions followed by assessment of binding of the reference antibody to the ANGPTL4 molecule. If, in both orientations, only the first (saturating) antibody is capable of binding to the ANGPTL4 molecule, then it is concluded that the test antibody and the reference antibody compete for binding to hANGPTL4. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res, 1990:50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-ANGPTL4 monoclonal antibody conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081.

Bispecifics

The antibodies of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-hANGPTL4 mAbs can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) $C_H 3$ domain and a second Ig $C_H 3$ domain, wherein the first and second Ig $C_H 3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H 3$ domain binds Protein A and the second Ig $C_H 3$ domain contains a mutation that reduces or abolishes Protein A binding such as an H95R modification (by IMGT exon numbering; H435R by EU numbering). The second $C_H 3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Bioequivalents

The anti-hANGPTL4 antibodies and antibody fragments of the present invention encompass proteins having amino acid sequences that vary from those of the described mAbs, but that retain the ability to bind human ANGPTL4. Such variant mAbs and antibody fragments comprise one or more additions, deletions, or substitutions of amino acids when compared to parent sequence, but exhibit biological activity that is essentially equivalent to that of the described mAbs. Likewise, the hANGPTL4 antibody-encoding DNA sequences of the present invention encompass sequences that comprise one or more additions, deletions, or substitutions of nucleotides when compared to the disclosed sequence, but that encode an anti-hANGPTL4 antibody or antibody fragment that is essentially bioequivalent to an anti-hANGPTL4 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied. In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-hANGPTL4 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Therapeutic Administration and Formulations

The invention provides therapeutic compositions comprising the anti-hANGPTL4 antibodies or antigen-binding fragments thereof of the present invention and the therapeutic methods using the same. The administration of therapeutic compositions in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose may vary depending upon the age and the size of a subject to be administered, target disease, the purpose of the treatment, conditions, route of administration, and the like. When the antibody of the present invention is used for treating various conditions and diseases directly or indirectly associated with ANGPTL4, including hypercholesterolemia, disorders associated with LDL and apolipoprotein B, and lipid metabolism disorders, and the like, in an adult patient, it is advantageous to intravenously or subcutaneously administer the antibody of the present invention at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 0.1 to about 800 mg per dosage form in a unit dose; especially in the form of injection, the aforesaid antibody is contained in about 1 to about 500 mg, in about 5 to 300 mg, in about 8 to 200 mg, and in about 10 to about 100 mg for the other dosage forms.

Combination Therapies

The invention further provides therapeutic methods for treating diseases or disorders, which is directly or indirectly associated with hANGPTL4, by administering the hANGPTL4 antibody or fragment thereof of the invention in combination with one or more additional therapeutic agents. The additional therapeutic agent may be one or more of any agent that is advantageously combined with the antibody or fragment thereof of the invention, including HMG-CoA reductase inhibitors, such as cerovastatin, atorvastatin, simvastatin, pitavastin, ros uvastatin, fluvastatin, lovastatin, pravastatin, and the like; niacin; various fibrates, such as fenofibrate, bezafibrate, ciprofibrate, clofibrate, gemfibrozil, and the like; LXR transcription factor activators, and the like. Furthermore, the hANGPTL4 antibody or fragment thereof of the invention can be co-administered with other ANGPTL4 inhibitors as well as inhibitors of other molecules, such as ANGPTL3, ANGPTL5, ANGPTL6 and proprotein convertase subtilisin/kexin type 9 (PCSK9), which are involved in lipid metabolism, in particular, cholesterol and/or triglyceride homeostasis. Inhibitors of these molecules include small molecules and antibodies that specifically bind to these molecules and block their activity (see, for example, anti-PCSK9 antibodies disclosed in U.S. 2010/0166768 A1).

Furthermore, the additional therapeutic agent may be one or more anti-cancer agents, such as chemotherapeutic agents, anti-angiogenic agents, growth inhibitory agents, cytotoxic agents, apoptotic agents, and other agents well known in the art to treat cancer or other proliferative diseases or disorders. Examples of anti-cancer agents include, but are not limited to, an anti-mitotic agent, such as docetaxel, paclitaxel, and the like; a platinum-based chemotherapeutic compound, such as cisplatin, carboplatin, iproplatin, oxaliplatin, and the like; or other conventional cytotoxic agent, such as 5-fluorouracil, capecitabine, irinotecan, leucovorin, gemcitabine, and the like, and anti-angiogenic agents, including vascular endothelial growth factor (VEGF) antagonists, such as anti-VEGF antibodies, e.g., bevacizumab (AVASTIN®, Genentech) and a receptor-based blocker of VEGF, e.g., "VEGF trap" described in U.S. Pat. No. 7,070,959, delta-like ligand 4 (Dll4) antagonists, such as anti-Dll4 antibodies as described in U.S. Patent Application Publication No. 2008/0181899, and a fusion protein containing the extracellular domain of DII4, e.g., DII4-Fc as described in U.S. Patent Application Publication No. 2008/0107648; inhibitors of receptor tyrosine kinases and/or angiogenesis, including sorafenib (NEXAVAR® by Bayer Pharmaceuticals Corp.), sunitinib (SUTENT® by Pfizer), pazopanib (VOTRIENT™ by Glaxo-SmithKline), toceranib (PALLADIA™ by Pfizer), vandetanib (ZACTIMA™ by AstraZeneca), cediranib (RECENTIN® by AstraZeneca), regorafenib (BAY 73-4506 by Bayer), axitinib (AG013736 by Pfizer), lestaurtinib (CEP-701 by Cephalon), erlotinib (TARCEVA® by Genentech), gefitinib (IRESSA™ by AstraZeneca), BIBW 2992 (TO-VOK™ by Boehringer Ingelheim), lapatinib (TYKERB® by GlaxoSmithKline), neratinib (HKI-272 by Wyeth/Pfizer), and the like, and pharmaceutically acceptable salts, acids or derivatives of any of the above. In addition, other therapeutic agents, such as analgesics, anti-inflammatory agents, including non-steroidal anti-inflammatory drugs (NSAIDS), such as Cox-2 inhibitors, and the like, may be also co-administered with the hANGPTL4 antibody or fragment thereof of the invention so as to ameliorate and/or reduce the symptoms accompanying the underlying cancer/tumor.

The hANGPTL4 antibody or fragment thereof of the invention and the additional therapeutic agent(s) can be co-administered together or separately. Where separate dosage formulations are used, the antibody or fragment thereof of the invention and the additional agents can be administered concurrently, or separately at staggered times, i.e., sequentially, in appropriate orders.

Diagnostic Uses of the Antibodies

The anti-ANGPTL4 antibodies of the present invention can be also used to detect and/or measure ANGPTL4 in a sample, e.g., for diagnostic purposes. For example, an anti-ANGPTL4 Ab or fragment thereof, can be used to diagnose a condition or disease characterized by aberrant expression (e.g., over-expression, under-expression, lack of expression, etc.) of ANGPTL4. Exemplary diagnostic assays for ANGPTL4 may comprise, e.g., contacting a sample obtained from a patient, with an anti-ANGPTL4 Ab of the invention, wherein the anti-ANGPTL4 antibody is labeled with a detectable label or reporter molecule or used to selectively capture and isolate ANGPTL4 protein from patient samples. Alternatively, an unlabeled anti-ANGPTL4 Ab can be used in diagnostic applications in combination with a secondary antibody which is itself detectably labeled. The detectable label or reporter molecule can be a radioisotope, such as $^3$H, $^{14}$C, $^{32}$P, $^{35}$S, $^{131}$I or $^{125}$I; a fluorescent or chemiluminescent moiety, such as fluorescein isothiocyanate, or rhodamine; or an enzyme such as alkaline phosphatase, β-galactosidase, horseradish peroxidase, or luciferase. Assays that can be used to detect or measure ANGPTL4 in a sample include enzyme-linked immunosorbent assay (ELISA), radioimmunoassay (RIA), fluorescence-activated cell sorting (FACS), and the like.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Example 1

Generation of Human Antibodies to Human ANGPTL4

VELOCIMMUNE™ mice were immunized with human ANGPTL4, and the antibody immune response monitored by antigen-specific immunoassay using serum obtained from these mice. Anti-hANGPTL4 expressing B cells were harvested from the spleens of immunized mice shown to have elevated anti-hANGPTL4 antibody titers and were fused with mouse myeloma cells to form hybridomas. The hybridomas were screened and selected to identify cell lines expressing hANGPTL4-specific antibodies using assays as described below. The assays identified several cell lines that produced chimeric anti-hANGPTL4 antibodies designated as H1M222, H1M223, H1M224, H1M225, H1M234 and H1M236.

Human ANGPTL4-specific antibodies were also isolated directly from antigen-immunized B cells without fusion to myeloma cells, as described in U.S. 2007/0280945 A1. Heavy and light chain variable regions were cloned to generate fully human anti-hANGPTL4 antibodies designated as H1H257, H1H268, H1H283, H1H284, H1H285, H1H291, H1H292, H1H295, H1H624, H1H637, H1H638, H1H644 and H1H653. Stable recombinant antibody-expressing CHO cell lines were established.

Example 2

Variable Gene Utilization Analysis

To analyze the structure of antibodies produced, the nucleic acids encoding antibody variable regions were cloned and sequenced. From the nucleic acid sequence and predicted amino acid sequence of the antibodies, gene usage was identified for each Heavy Chain Variable Region (HCVR) and Light Chain Variable Region (LCVR). Table 1 shows the gene usage for selected antibodies in accordance with the invention.

TABLE 1

| Antibody | HCVR | | | LCVR | |
|---|---|---|---|---|---|
|  | $V_H$ | $D_H$ | $J_H$ | $V_K$ | $J_K$ |
| H1M225 | 3-9 | 1-7 | 1 | 1-5 | 2 |
| H1M236 | 3-9 | 6-6 | 5 | 3-15 | 5 |
| H1H283 | 3-13 | 1-26 | 4 | 1-5 | 1 |
| H1H285 | 3-13 | 1-26 | 4 | 1-5 | 1 |
| H1H291 | 3-13 | 1-26 | 4 | 1-5 | 1 |
| H1H292 | 3-13 | 1-26 | 4 | 1-5 | 1 |
| H1H295 | 3-13 | 1-26 | 4 | 1-5 | 1 |
| H1H637 | 3-13 | 1-26 | 4 | 1-5 | 1 |
| H1H638 | 3-13 | 1-26 | 4 | 1-5 | 1 |
| H1H644 | 3-13 | 1-26 | 4 | 1-5 | 1 |
| H1H257 | 3-13 | 1-26 | 4 | 1-5 | 1 |
| H1M224 | 3-13 | 3-3 | 4 | 1-16 | 3 |
| H1M223 | 3-15 | 3-3 | 4 | 1-12 | 3 |
| H1M234 | 3-15 | 3-3 | 4 | 1-12 | 3 |
| H1H624 | 3-23 | 5-5 | 6 | 1-9 | 3 |
| H1H284 | 3-30 | 5-12 | 6 | 1-9 | 4 |
| H1M222 | 3-33 | 3-9 | 5 | 3-20 | 4 |
| H1H653 | 3-33 | 2-8 | 6 | 1-17 | 2 |
| H1H268 | 4-34 | 3-3 | 4 | 1-27 | 4 |

Table 2 shows the heavy and light chain variable region amino acid sequence pairs of selected anti-hANGPTL4 antibodies and their corresponding antibody identifiers. The N, P and L designations refer to antibodies having heavy and light chains with identical CDR sequences but with sequence variations in regions that fall outside of the CDR sequences (i.e., in the framework regions). Thus, N, P and L variants of a particular antibody have identical CDR sequences within their heavy and light chain variable regions but contain modifications within the framework regions.

TABLE 2

| Name | HCVR/LCVR SEQ ID NOs |
|---|---|
| H1M222N | 314/322 |
| H1M223N | 410/418 |
| H1M224N | 338/346 |
| H1M225N | 362/370 |
| H1M234N | 434/442 |
| H1M236N | 386/394 |
| H1H236N2 | 458/394 |
| H1H257N | 2/10 |
| H1H268N | 26/34 |
| H1H283N | 50/58 |
| H1H284N | 74/82 |
| H1H285N | 98/106 |
| H1H291N | 122/130 |
| H1H292N | 146/154 |
| H1H295N | 170/178 |
| H1H624N | 194/202 |
| H1H637N | 218/226 |
| H1H638N | 242/250 |
| H1H644N | 266/274 |
| H1H653N | 290/298 |
| H1M222P | 330/332 |
| H1M223P | 426/428 |
| H1M224P | 354/356 |
| H1M225P | 378/380 |
| H1M234P | 450/452 |
| H1M236P | 402/404 |
| H1H236P2 | 466/404 |
| H1H257P | 18/20 |
| H1H268P | 42/44 |
| H4H268P2 | 487/44 |
| H1H283P | 66/68 |
| H1H284P | 90/92 |
| H1H285P | 114/116 |
| H1H291P | 138/140 |
| H1H292P | 162/164 |
| H1H295P | 186/188 |
| H1H624P | 210/212 |
| H1H637P | 234/236 |
| H1H638P | 258/260 |
| H1H644P | 282/284 |
| H1H653P | 306/308 |
| H1M222L | 334/336 |
| H1M223L | 430/432 |
| H1M224L | 358/360 |
| H1M225L | 382/384 |
| H1M234L | 454/456 |
| H1M236L | 406/408 |
| H1H236L2 | 468/408 |
| H1H257L | 22/24 |
| H1H268L | 46/48 |
| H1H283L | 70/72 |
| H1H284L | 94/96 |
| H1H285L | 118/120 |
| H1H291L | 142/144 |
| H1H292L | 166/168 |
| H1H295L | 190/192 |
| H1H624L | 214/216 |
| H1H637L | 238/240 |
| H1H638L | 262/264 |
| H1H644L | 286/288 |
| H1H653L | 310/312 |

Example 3 hANGPTL4 Binding Affinity Determination

Equilibrium dissociation constants ($K_D$ values) for antigen binding to selected antibodies that bind amino acid residues 26-148 of human ANGPTL4 fused in-line to mouse IgG2a (hANGPTL4-mFc; SEQ ID NO:480) were determined by surface kinetics using a real-time biosensor surface plasmon resonance assay (BIACORE™ T100). hANGPTL4-mFc was captured with goat anti-mouse IgG polyclonal antibody (GE Healthcare) that was chemically coupled to a BIACORE™ chip through free amino groups. Varying concentrations (ranging from 12.5 nM to 50 nM) of anti-ANGPTL4 antibodies were injected over the captured antigen surface for 90 seconds. Antigen-antibody binding and dissociation were monitored in real time at 25° C. and 37° C. Kinetic analysis was performed to calculate $K_D$ and half-life of antigen/antibody complex dissociation. Results are shown in Table 3. A human anti-EGFR antibody was used as a negative control, which showed no binding to the captured hANGPTL4-mFc.

TABLE 3

| | 25° C. | | 37° C. | |
|---|---|---|---|---|
| Antibody | $K_D$ (pM) | $t_{1/2}$ (min) | $K_D$ (pM) | $t_{1/2}$ (min) |
| H1H257P | 201 | 91 | 238 | 63 |
| H1H268P | 275 | 80 | 389 | 57 |
| H1H283P | 130 | 119 | 1360 | 12 |
| H1H284P | 168 | 162 | 349 | 81 |
| H1H285P | 92.5 | 156 | 194 | 71 |
| H1H291P | 87.6 | 303 | 178 | 122 |
| H1H292P | 136 | 112 | 167 | 88 |
| H1H295P | 30.7 | 874 | 2620 | 10 |
| H1H624P | 1190 | 7 | 3710 | 3 |
| H1H638P | 193 | 85 | 299 | 48 |
| H1H644P | 111 | 144 | 3000 | 6 |
| H1H653P | 411 | 43 | 2130 | 6 |

For H1H268P and H1H284P, Fab fragments were prepared by papain digestion and purified by standard purification methods, and their binding affinities to hANGPTL4 were measured at 25° C. at pH 7.2 and pH 5.75 using the BIACORE™ system, essentially according to the method described above. Briefly, various concentrations (3.125 nM-100 nM) of anti-hANGPTL4 antibodies (i.e., H1H268 Fab, entire H1H268 mAb, H1H284 Fab, and entire H1H284 mAb) were injected over a low density anti-mFc captured hANGPTL4(26-148)-mFc (~68±4 RU) surface, or the surface of amino-coupled hANGPTL4(26-406)-His (R&D Systems) (450 RU) or amino-coupled cynomolgus monkey N-terminal region (amino acid residues 1-130 of SEQ ID NO:490) expressed with an C-terminal hexa-histidine tag (MfANGPTL4(1-130)-His) (1,028 RU). Kinetic analysis was performed to measure $k_a$ and $k_d$, and $K_D$ values and half-life of antigen/antibody complex dissociation were calculated. The results are shown in Table 4 (H1H268P) and Table 5 (H1H284P).

TABLE 4

| Antigen | Antibody H1H268P | pH | Antigen captured (RU) | 50 mM mAb or Fab bound | $k_a$ ($M^{-1}s^{-1}$) | $k_d$ ($s^{-1}$) | $K_D$ (pM) | $t_{1/2}$ (min) |
|---|---|---|---|---|---|---|---|---|
| hANGPTL4 (26-148)-mFc | Full mAb | 7.2 | 35 ± 1.9 | 40 | $1.53 \times 10^5$ | $9.59 \times 10^{-5}$ | 629 | 120 |
| | | 5.75 | 27 ± 0.6 | 77 | $6.28 \times 10^5$ | $1.38 \times 10^{-4}$ | 220 | 84 |
| | Fab | 7.2 | 35 ± 1.9 | 10 | $3.00 \times 10^5$ | $6.01 \times 10^{-4}$ | 2,000 | 19 |
| | | 5.75 | 27 ± 0.6 | 20 | $1.74 \times 10^5$ | $3.04 \times 10^{-3}$ | 17,500 | 4 |
| hANGPTL4 (26-406)-His | Full mAb | 7.2 | Amino-coupled | 38 | $4.89 \times 10^5$ | $2.00 \times 10^{-4}$ | 408 | 58 |
| | | 5.75 | | 45 | $9.23 \times 10^5$ | $4.46 \times 10^{-4}$ | 483 | 26 |
| | Fab | 7.2 | 450 RU | 13 | $7.26 \times 10^5$ | $1.18 \times 10^{-2}$ | 16,300 | 1 |
| | | 5.75 | | 10 | $4.44 \times 10^5$ | $6.57 \times 10^{-3}$ | 14,800 | 2 |
| MfANGPTL4(1-130)-His | Full mAb | 7.2 | Amino-coupled | 279 | $3.92 \times 10^5$ | $4.76 \times 10^{-5}$ | 122 | 243 |
| | | 5.75 | | 583 | $1.07 \times 10^5$ | $8.24 \times 10^{-5}$ | 77.2 | 140 |
| | Fab | 7.2 | 1,028 RU | 167 | $2.67 \times 10^5$ | $1.71 \times 10^{-3}$ | 6,420 | 7 |
| | | 5.75 | | 178 | $3.12 \times 10^5$ | $4.32 \times 10^{-3}$ | 13,800 | 3 |

TABLE 5

| Antigen | Antibody H1H284P | pH | Antigen captured (RU) | 50 mM mAb or Fab bound | $k_a$ ($M^{-1}s^{-1}$) | $k_d$ ($s^{-1}$) | $K_D$ (pM) | $t_{1/2}$ (min) |
|---|---|---|---|---|---|---|---|---|
| hANGPTL4 (26-148)-mFc | Full mAb | 7.2 | 35 ± 1.9 | 99 | $2.74 \times 10^5$ | $5.36 \times 10^{-5}$ | 196 | 216 |
| | | 5.75 | 27 ± 0.6 | 171 | $1.09 \times 10^6$ | $8.91 \times 10^{-5}$ | 81.9 | 130 |
| | Fab | 7.2 | 35 ± 1.9 | 29 | $2.45 \times 10^5$ | $2.02 \times 10^{-4}$ | 823 | 57 |
| | | 5.75 | 27 ± 0.6 | 56 | $4.72 \times 10^5$ | $1.60 \times 10^{-3}$ | 3,400 | 7 |
| hANGPTL4 (26-406)-His | Full mAb | 7.2 | Amino-coupled | 77 | $8.50 \times 10^5$ | $8.85 \times 10^{-5}$ | 105 | 130 |
| | | 5.75 | | 101 | $1.93 \times 10^6$ | $2.72 \times 10^{-4}$ | 141 | 42 |
| | Fab | 7.2 | 450 RU | 32 | $1.11 \times 10^6$ | $3.44 \times 10^{-4}$ | 310 | 34 |
| | | 5.75 | | 33 | $1.21 \times 10^6$ | $1.73 \times 10^{-3}$ | 1,440 | 7 |
| MfANGPTL4(1-130)-His | Full mAb | 7.2 | Amino-coupled | 414 | $4.67 \times 10^5$ | $5.83 \times 10^{-5}$ | 125 | 198 |
| | | 5.75 | | 804 | $1.55 \times 10^6$ | $8.42 \times 10^{-5}$ | 54.3 | 137 |
| | Fab | 7.2 | 1,028 RU | 214 | $3.10 \times 10^5$ | $3.13 \times 10^{-3}$ | 10,100 | 4 |
| | | 5.75 | | 255 | $7.24 \times 10^5$ | $6.19 \times 10^{-3}$ | 8,540 | 2 |

Both Fab fragments were capable of binding to all forms of ANGPTL4, albeit with lower affinities than the whole antibody molecules.

Example 4

Anti-hANGPTL4 Antibody Cross-Reactivity Determination

Possible cross-reactivity of the anti-hANGPTL4 antibodies to related proteins, i.e., hANGPTL3, human angiopoietin-like protein 5 (hANGPTL5) and mouse ANGPTL4 (mANGPTL4), was tested for the selected antibodies, i.e., H1H268P and H1H284P, using the BIACORE™ system. Briefly, anti-hANGPTL4 antibodies as well as negative controls, i.e., two monoclonal antibodies (Control a and Control b) that are non-binders to any ANGPTL proteins, were injected at 3.125 µg/mL-50 µg/mL over amine coupled chip surfaces of hANGPTL3-His (R&D Systems, cat #3829-AN) at 5228 RU, hANGPTL4-His (R&D Systems, cat #4487-AN) at 6247 RU, hANGPTL5-His (Abnova Corp., cat #H00253935-P01) at 5265 RU, and mANGPTL4-His [R26-S410 of mANGPTL4 (SEQ ID NO: 478) fused with an AS linker to a C-terminal 6-histidine tag] at 5233 RU, respectively. A polyclonal antibody specific for hANGPTL3 (R&D System, cat #BAF3485) was also tested. The binding of each antibody, expressed as a specific RU value, was determined and the results are shown in Table 6.

TABLE 6

| | Specific RU | | | |
|---|---|---|---|---|
| mAb injected | hANGPTL3-His | hANGPTL4-His | hANGPTL5-His | mANGPTL4-His |
| Buffer | −17 | −23 | −18 | −7 |
| H1H268P | −17 | 768 | −16 | −7 |
| H1H284P | −6 | 1351 | −13 | 18 |
| Control a | −16 | −23 | −18 | −6 |
| Control b | −17 | −23 | −18 | −6 |
| Anti-hANGPTL3 | 680 | −1 | −1 | 2319 |

H1H268P and H1H284P only bound specifically to hANGPTL4-His and did not bind any of the other related ANGPTL proteins.

Further, the binding affinities of H1H268P and H1H284P for various ANGPTL3 and ANGPTL4 peptides were also determined by BIACORE™ system. Briefly, H1H268P (1348±11 RU) and H1H284P (868±13 RU) were captured over anti-human Fc surface and various concentrations (62.5 nM-500 nM) of the hANGPTL3 and hANGPTL4 peptides were injected. The peptides tested were hANGPTL4 (R34-L66 of SEQ ID NO:476), N-terminally biotinylated hANGPTL4 (R34-L66 of SEQ ID NO:476), hANGPTL3 (R36-I68 of SEQ ID NO:485), and N-terminally biotinylated hANGPTL3 (R36-I68 of SEQ ID NO:485). Kinetic analysis was performed to measure $k_a$ and $k_d$, and $K_D$ values and half-life of antigen/antibody complex dissociation were calculated. The results are shown in Table 7. NB: No binding under the experimental conditions described.

TABLE 7

| Anti-hANGPTL4 Antibody | Peptide | $k_a$ (M$^{-1}$s$^{-1}$) | $k_d$ (s$^{-1}$) | $K_D$ (nM) | $t_{1/2}$ (min) |
|---|---|---|---|---|---|
| H1H268P | hANGPTL3-Nterm biotin | NB | — | — | — |
| | hANGPTL4-Nterm biotin | $4.53 \times 10^3$ | $2.94 \times 10^{-4}$ | 64.8 | 39 |
| | hANGPTL3 | NB | — | — | — |
| | hANGPTL4 | $6.49 \times 10^3$ | $3.65 \times 10^{-4}$ | 56.3 | 32 |

Neither of the antibodies bound to any of the hANGPTL3 peptides. In addition, H1H284P did not bind to any of the hANGPTL4 peptides even at the highest peptide concentration tested (500 nM), while H1H268P was able to bind to both hANGPTL4 peptides. This suggests that H1H268P recognizes a linear epitope within the 34-66 region. In contrast, H1H284P either binds outside this region or does not recognize a linear epitope in this region.

Example 5

Inhibition of hANGPTL4 by Anti-ANGPTL4 Antibodies

Lipoprotein Lipase (LPL) plays a critical role in lipid metabolism in humans. LPL catalyzes hydrolysis of triglycerides and releases fatty acids to be metabolized. ANGPTL4 inhibits LPL activity leading to increased level of lipids (Oike et al., 2005, *Trends in Molecular Medicine* 11(10):473-479). The N-terminal coiled-coil region of ANGPTL4 undergoes homo-multimerization, both in isolation and when joined to the C-terminal fibrinogen-like region. The N-terminal region also inhibits LPL when expressed without the C-terminal fibrinogen region. A cell-free bioassay was developed to determine the ability of selected anti-hANGPTL4 antibodies to inhibit ANGPTL4-induced decrease in LPL activity.

Inhibition of hANGPTL4 activity by selected anti-hANGPTL4 antibodies was determined using the CON-FLUOLIP™ Continuous Fluorometric Lipase Test (Progen, Germany) using two hANGPTL4 proteins: full-length hANGPTL4 (i.e., amino acid residues 26-406 of SEQ ID NO:476) with a C-terminal hexa-histidine tag (hANGPTL4-His; R&D Systems, MN) and hANGPTL4-mFc (SEQ ID NO:480) containing the N-terminal coiled-coil region.

Briefly, 2 nM bovine LPL, 0.25 µM human ApoCII (a cofactor of LPL), 2 mg/mL BSA and 1.6 mM CaCl$_2$, were premixed in a 96-well assay plate. Either hANGPTL4-His or hANGPTL4-mFc protein was added to the Apo/LPL mixture to a final concentration of 10 nM and 2 nM, respectively. The Apo/LPL/ANGPTL4 protein mixtures were then added together with serially diluted anti-hANGPTL4 antibodies with a starting concentration of 300 nM (for inhibition of hANGPTL4-His) or 100 nM (for inhibition of hANGPTL4-mFc) and incubated at room temperature for 30 minutes (final volume 50 µl). Following the incubation, 200 µl of reconstituted lipase substrate, 1-trinitrophenyl-amino-dodecanoyl-2-pyrendecanoyl-3-O-hexadecyl-sn-glycerol (LS-A, Progen), was added to the antibody mixture and incubated at 37° C. for two hours. Fluorescence was then measured at 342 nm/400 nm (excitation/emission) using a FlexStation® 3 Microplate Reader (Molecular Devices, CA). Fluorescence is directly proportional to LPL activity. Results are shown in Table 8. Control I: a rabbit polyclonal antibody specific for hANGPTL4 (BioVendor). Control II: an irrelevant human antibody that does not bind hANGPTL4. NT: not tested. The total inhibition (i.e., 100% inhibition) was determined from the relative fluorescence unit (RFU) of the assay with 2 nM bovine LPL, 0.25 µM human ApoCII, 2 mg/mL BSA and 1.6 mM CaCl$_2$, in the absence of anti-ANGPTL4 antibodies and ANGPTL4 proteins.

TABLE 8

| | % Inhibition of hANGPTL4 Activity | |
|---|---|---|
| Antibody | hANGPTL4-mFc (2 nM) | hANGPTL4-His (10 nM) |
| H1H236N2 | 13 | 19 |
| H1H257P | 16 | NT |
| H1H268P | 76 | 80 |
| H1H284P | 82 | 90 |
| H1H285P | 28 | 47 |
| H1H292P | 20 | 53 |
| H1H624P | 62 | 48 |
| H1H653P | 55 | 48 |
| Control I | 29 | 66 |
| Control II | No inhibition | No inhibition |

Antibodies H1H284P and H1H268P exhibited the highest inhibition of ANGPTL4's inhibitory activity against LPL among the antibodies tested, including the polyclonal hANGPTL4 antibody control. For antibodies H1H284P and H1H268P, the antibody concentrations required for 50% maximum inhibition (1050) of 2 nM hANGPTL4-mFc were determined to be 0.8 nM and 1.2 nM, respectively. In addition, the antibody concentrations required for 50% maximum inhibition of 10 nM hANGPTL4-His were determined to be 0.5 nM and 0.2 nM, respectively.

Similarly, H1H284P and H1H268P were tested in the LPL bioassay for their ability to inhibit cross-species orthologs: the cynomolgus monkey N-terminal region (amino acid residues 26-148) expressed with an N-terminal hexa-histidine tag (His-MfANGPTL4; SEQ ID NO:488) and the mouse full-length ortholog (amino acid residues 26-410 of SEQ ID NO:478) with a C-terminal hexa-histidine tag (mANGPTL4-His). A full dose-response using the ANGPTL4 protein in the LPL assay was first performed to determine the ANGPTL4 EC50 for each experiment and 1050 determinations for each antibody were then performed using constant concentrations of ANGPTL4 protein, as shown in Table 9. Antibody concentrations ranged from 0 to 100 nM. NB: Not blocking.

TABLE 9

|  | hANGPTL4 (26-406)-His | hANGPTL4 (26-148)-mFc | His-MfANGPTL4 (26-148) | mANGPTL4 (26-410)-His |
|---|---|---|---|---|
| EC50 (nM) | 6.00 | 0.50 | 3.89 | 0.63 |
| Constant ANGPTL4 (nM) | 10 | 2 | 10 | 1 |
| IC50 (nM)  H1H268P | 0.46 | 0.47 | 0.42 | NB |
| H1H284P | 0.31 | 0.51 | 0.42 | NB |
| IgG1 control | NB | NB | NB | NB |

Both antibodies inhibited both human ANGPTL4 (full-length and N-terminal) and monkey ANGPTL4 (N-terminal) protein activity with IC50s of about 0.3-0.5 nM; but neither antibody inhibited mouse ANGPTL4 (full-length) up to the highest antibody concentrations tested (i.e., 100 nM).

Example 6

In Vivo Effect of ANGPTL4 on Plasma Lipid Levels hANGPTL4 was administered intravenously to C57BL/6 mice to determine the biological effect of hANGPTL4 on plasma lipid levels. Briefly, C57BL/6 mice were put into four groups of five animals and each group was administered with different amount of hANGPTL4-mFc protein (SEQ ID NO:480): 25 µg, 50 µg, 100 µg and 300 µg, per mouse. A control group received injections of PBS. hANGPTL4-mFc protein and PBS were administered by intravenous injection (i.v.) via tail vein. Mice were bled at 15 min, 30 min, 60 min and 120 min after delivery of hANGPTL4-mFc or PBS and plasma lipid levels were determined by ADVIA® 1650 Chemistry System (Siemens). Measurements of triglycerides, total cholesterol, low density lipoprotein (LDL), nonesterified fatty acids (NEFA-C) and high density lipoprotein (HDL) were determined for each dose group. Measurements of total cholesterol, LDL, NEFA-C and HDL were not significantly different across each dose group for each time point post-injection. Injection of 25 µg/mouse of hANGPTL4-mFc increased circulating triglycerides greater than two-fold as compared to control mice (PBS) 30 minutes post injection. Thus, the 25 µg dose of hANGPTL4-mFc was selected as a possible minimum dosage for analysis of inhibition of ANGPTL4-induced increase in serum triglyceride levels by selected anti-hANGPTL4 antibodies as described below.

Example 7

In Vivo Inhibition of ANGPTL4 by Anti-ANGPTL4 Antibodies

In another set of experiments, selected anti-hANGPTL4 antibodies were tested for their ability to inhibit hANGPTL4-induced increase of triglyceride levels. Measurements of total cholesterol, LDL, NEFA-C and HDL were also made. Briefly, C57BL/6 mice were put into groups of five mice each for each antibody tested. Antibodies were administered at 5 mg/kg dose by subcutaneous injection. Control group I, i.e., mice that received neither anti-hANGPTL4 antibodies nor hANGPTL4, were administered with PBS. Twenty-four hours post-injection of antibody, hANGPTL4-mFc (SEQ ID NO:480) was administered (i.v.) at a dose of 25 µg/mouse to each antibody group. Mice were bled at 30 min after hANGPTL4-mFc injection and lipid levels were determined by ADVIA® 1650 Chemistry System (Siemens). Averages were calculated for each of the measurements of triglycerides, total cholesterol (Total-C), LDL, NEFA-C and HDL for each antibody or control group. Levels of circulating anti-hANGPTL4 antibodies (Serum Ab) were also determined using a standard ELISA assay. Briefly, plates were coated with a goat anti-human Fc antibody (Sigma-Aldrich) to capture Serum Ab. Serum was then added to the plates and captured anti-hANGPTL4 antibodies were detected by chemiluminescence using a horseradish peroxidase (HRP) conjugated goat anti-human IgG antibody (Sigma-Aldrich). Results, expressed as (mean±SEM) of serum lipid concentration, are shown in Tables 10-12. Control I: Mice that received PBS, but neither anti-hANGPTL4 antibodies nor hANGPTL4-mFc. Control II: Mice that received a human antibody specific for CD20 (i.e., the mAb having the sequence of 2F2 clone disclosed in US 2008/0260641) and hANGPTL4-mFc.

TABLE 10

| Antibody | Triglycerides (mg/dL) | Total-C (mg/dL) | LDL (mg/dL) | NEFA-C (mg/dL) | HDL (mg/dL) | Serum Ab (µg/mL) |
|---|---|---|---|---|---|---|
| Control I | 98.20 ± 5.49 | 89.80 ± 4.28 | 5.60 ± 0.66 | 1.01 ± 0.04 | 44.18 ± 2.43 | — |
| Control II | 211.60 ± 58.29 | 93.40 ± 5.52 | 6.30 ± 0.22 | 1.33 ± 0.17 | 44.62 ± 3.14 | 12.76 ± 0.52 |
| H1H284P | 99.20 ± 9.52 | 80.80 ± 6.40 | 4.98 ± 0.87 | 0.99 ± 0.11 | 39.60 ± 3.46 | 7.96 ± 0.55 |
| H1H257P | 115.80 ± 6.43 | 84.40 ± 3.53 | 5.30 ± 0.36 | 0.97 ± 0.03 | 41.38 ± 3.24 | 8.43 ± 0.86 |

TABLE 11

| Antibody | Triglycerides (mg/dL) | Total-C (mg/dL) | LDL (mg/dL) | NEFA-C (mg/dL) | HDL (mg/dL) | Serum Ab (µg/mL) |
|---|---|---|---|---|---|---|
| Control I | 66.60 ± 7.94 | 70.00 ± 2.3 | 3.88 ± 0.36 | 0.76 ± 0.08 | 35.26 ± 1.09 | — |
| Control II | 161.00 ± 17.83 | 73.60 ± 0.93 | 4.12 ± 0.17 | 1.18 ± 0.09 | 35.10 ± 0.6 | 11.05 ± 2.28 |

TABLE 11-continued

| Antibody | Triglycerides (mg/dL) | Total-C (mg/dL) | LDL (mg/dL) | NEFA-C (mg/dL) | HDL (mg/dL) | Serum Ab (µg/mL) |
|---|---|---|---|---|---|---|
| H1H236N2 | 151.80 ± 9.26 | 72.40 ± 1.81 | 4.26 ± 0.25 | 1.11 ± 0.18 | 33.78 ± 1.13 | 9.20 ± 0.63 |
| H1H624P | 81.20 ± 9.26 | 72.80 ± 5.49 | 4.36 ± 0.92 | 0.86 ± 0.07 | 35.40 ± 2.68 | 11.76 ± 0.89 |
| H1H268P | 92.60 ± 11.44 | 76.00 ± 2.14 | 4.94 ± 0.51 | 0.82 ± 0.04 | 35.94 ± 1.64 | 8.05 ± 1.06 |

TABLE 12

| Antibody | Triglycerides (mg/dL) | Total-C (mg/dL) | LDL (mg/dL) | NEFA-C (mg/dL) | HDL (mg/dL) | Serum Ab (µg/mL) |
|---|---|---|---|---|---|---|
| Control I | 94.20 ± 10.91 | 75.00 ± 5.32 | 3.98 ± 0.25 | 1.01 ± 0.05 | 40.46 ± 3.25 | — |
| Control II | 179.80 ± 28.06 | 76.80 ± 3.46 | 4.38 ± 0.09 | 1.30 ± 0.13 | 39.06 ± 2.94 | 11.59 ± 1.2 |
| H1H291P | 111.00 ± 7.51 | 71.20 ± 3.26 | 3.84 ± 0.12 | 1.11 ± 0.04 | 38.24 ± 2.14 | 9.46 ± 0.73 |
| H1H283P | 113.60 ± 8.74 | 75.80 ± 1.53 | 4.62 ± 0.39 | 1.13 ± 0.05 | 40.30 ± 0.72 | 7.85 ± 1.00 |
| H1H295P | 104.80 ± 9.44 | 74.60 ± 4.82 | 4.04 ± 0.40 | 1.12 ± 0.04 | 39.70 ± 3.13 | 12.61 ± 0.83 |
| H1H653P | 88.00 ± 13.52 | 74.20 ± 4.49 | 3.84 ± 0.32 | 1.04 ± 0.1 | 40.10 ± 2.72 | 8.77 ± 1.06 |
| H1H285P | 91.40 ± 11.99 | 76.40 ± 1.75 | 3.72 ± 0.44 | 0.97 ± 0.06 | 42.20 ± 0.91 | 10.49 ± 0.67 |
| H1H292P | 85.80 ± 7.00 | 74.40 ± 2.11 | 3.96 ± 0.15 | 1.06 ± 0.06 | 39.44 ± 1.68 | 12.61 ± 0.55 |
| H1H638P | 102.80 ± 10.75 | 73.80 ± 2.78 | 4.14 ± 0.18 | 1.06 ± 0.05 | 39.54 ± 1.65 | 12.20 ± 0.80 |

After injection of hANGPTL4-mFc (25 µg), most of the anti-hANGPTL4 antibodies tested (shown in Tables 10-12) exhibited significantly reduced levels of serum triglycerides compared to mice treated with irrelevant antibody (control II).

Example 8

Preparation of Anti-ANGPTL4 Antibodies with hIgG4 Isotype

The antibodies H1H268P and H1H284P with hIgG1 isotype were converted to hIgG4 isotype by replacing the respective constant regions with the hIgG4 amino acid sequence of SEQ ID NO:483, which contains a S108P mutation in the hinge region. Furthermore, a single amino acid substitution was introduced in the framework region 1 of H1H268P (SEQ ID NO:42) to form H4H268P2 (SEQ ID NO:487) in the IgG4 version. $K_D$ (pM) and $t_{1/2}$ values of the IgG4 antibodies, designated as H4H268P2 and H4H284P, respectively, for hANGPTL4-mFc (SEQ ID NO:480) binding were obtained by Biacore at pH7.4 and 25° C., according to the protocol as described in Example 3 above. The results are shown in Table 13 below.

TABLE 13

| Antibody | $K_D$ (pM) | $t_{1/2}$ (min) |
|---|---|---|
| H4H268P2 | 146 | 195 |
| H4H284P | 143 | 205 |

H4H268P2 and H4H284P together with the corresponding IgG1 versions, H1H268P and H1H284P, respectively, were tested in the LPL inhibition assay, as described in Example 5 above, to determine I050 values. The results are shown in Table 14. NB: Not blocking.

TABLE 14

| | | hAngPTL4 (26-406)-His | hANGPTL4 (26-148)-mFc |
|---|---|---|---|
| EC50 (nM) | | 4.54 | 0.29 |
| Constant ANGPTL4 (nM) | | 10 | 2 |
| IC50 (nM) | H1H268P | 0.20 | 0.67 |
| | H1H284P | 0.42 | 0.33 |
| | IgG1 control | NB | NB |
| | H4H268P2 | 1.61 | 1.85 |
| | H4H284P | 1.19 | 1.69 |
| | IgG4 control | NB | NB |

In this assay, H1H268P and H1H284P showed IC50s ranging from about 0.2-0.7 nM for the full-length and the N-terminal hANGPTL4 proteins, while H4H268P2 and H4H284P showed IC50s ranging from about 1.0-2.0 nM.

Example 9

Pharmacokinetic Study of Anti-ANGPTL4 Antibodies

Pharmacokinetic clearance rates of anti-hANGPTL4 antibodies H4H268P2 and H4H284P were determined in wild-type mice and in transgenic mice expressing human ANGPTL4 [hANGPTL4(+/+) mice]. The strain background for both wild-type and transgenic mice was C57BL6 (75%) and 129Sv (25%). Separate cohorts consisting of 5 mice each of either wild-type or hANGPTL4(+/+) mice received subcutaneously (s.c.) 1 mg/kg of H4H268P2, H4H284P, or an isotype-matched (hIgG4) control with irrelevant specificity. Blood samples were collected at 0 hour, 6 hours, 1 day, 2 days, 3 days, 4 days, 7 days, 10 days, and 15 days, 22 days, and 30 days after the injection. Serum levels of human antibodies were determined by a sandwich ELISA. Briefly, a goat polyclonal anti-human IgG (Fc-specific) capture antibody (Jackson ImmunoResearch, PA) was coated in 96-well plates at a concentration of 1 µg/mL and incubated overnight at 4° C. After the plates were blocked with BSA, serum samples in a six-point serial dilution and reference standards of the respective antibody in a twelve-point serial dilution were added to the plate and incubated for one hour at room temperature. After washing with a suitable washing buffer, captured human antibodies were detected using the same goat polyclonal anti-human IgG (Fc-specific) antibody conjugated with horse radish peroxidase (HRP) (Jackson ImmunoResearch, PA) and developed by standard colorimetric response using tetramethylbenzidine (TMB) substrate, measuring absorbance at 450 nm in a plate reader. Concentrations of human antibodies in serum were determined using the reference standard curve generated for the same sample plate. The results are shown in Table 15 and FIGS. 3A and 3B.

TABLE 15

| Antibody | Mouse Genotype | Cmax (µg/mL) | AUC (hr*µg/mL) |
|---|---|---|---|
| H4H268P2 | Wild-type | 18.4 | 318 |
| H4H284P | Wild-type | 15.7 | 200 |
| hIgG4 control | Wild-type | 14.2 | 199 |
| H4H268P2 | hANGPTL4(+/+) | 13.3 | 37.0 |
| H4H284P | hANGPTL4(+/+) | 5.86 | 7.60 |
| hIgG4 control | hANGPTL4(+/+) | 11.6 | 168 |

As shown in Table 15, both anti-hANGPTL4 antibodies showed similar clearance rates as the isotype-matched control antibody in wild-type mice, as reflected in the area under the curve (AUC) calculated over the 30-day period of about 318, 200, and 199 (hr*µg/mL), respectively, for H4H268P2, H4H284P, and hIgG4 control (also see FIG. 3A). In the transgenic mice expressing only human ANGPTL4 [hANGPTL4 (+/+)], the clearance rates as reflected in AUCs were faster for both H4H268P2 (37.0 hr*µg/mL) and H4H284P (7.60 hr*µg/mL) compared to clearance rates in wild-type mice (318 and 200 hr*µg/mL, respectively) and compared to the clearance rate of the isotype-matched control antibody in either the hANGPTL4(+/+) mice (168 hr*µg/mL) or the wild-type mice (199 hr*µg/mL) (also see FIG. 3B). In the hANGPTL4(+/+) mice, the 30-day AUC for H4H284P (7.60 hr*µg/mL) was about 5-fold less than that for H4H268P2 (37.0 hr*µg/mL). Together these results suggest that both anti-hANGPTL4 antibodies exhibit target-mediated clearance in mice expressing human ANGPTL4, and H4H284P exhibits a substantially faster clearance rate than H4H268P2.

Example 10

In Vivo Effect of IgG1 Anti-hANGPTL4 Antibodies on Circulating TG Levels in Humanized ANGPTL4 Mice The effect of anti-hANGPTL4 antibodies H1H268P and H1H284P on serum TG levels was determined in mice expressing the ANGPTL4 protein containing the human N-terminal coil-coil region ("humanized ANGPTL4 mice"). The humanized ANGPTL4 mouse was made by replacing first three exons of the mouse Angptl4 gene (the N terminal coil-coil region) with the corresponding human N-terminal coil-coil ANGPLT4 sequence in C57BL6/129 (F1H4) embryonic stem cells. After germ line transmission was established, heterozygous mice (ANGPTL4hum/+) were bred together to generate homozygous mice [ANGPTL4hum/hum or hANGPTL4(+/+)] on a C57BL6 background. Humanized ANGPTL4 mice were pre-bled 7 days before (day −7) the experiment and put into groups of six mice each for each antibody tested. Antibodies (H1H268P, H1H284P and isotype-matched (hIgG1) control with no known cross-reactivity to mouse antigens) were administered at 10 mg/kg dose by subcutaneous injection. Mice were bled after 4 hours of fasting at days 1, 4, 7 and 11 after antibody injection; and serum TG levels were determined by ADVIA® 1800 Chemistry System (Siemens). Average TG levels were calculated for each time point for each antibody. Results, expressed as (mean±SEM) of serum TG concentration, are shown in Table 16.

TABLE 16

| Days after injection | Serum TG (mg/dL) | | |
|---|---|---|---|
| | hIgG1 Control | H1H268P | H1H284P |
| −7 | 117 ± 18 | 112 ± 9.3 | 113 ± 11 |
| 1 | 138 ± 21 | 129.8 ± 5.6 | 125 ± 18 |
| 4 | 102 ± 14 | 73.3 ± 8.9 | 67 ± 9.8 |
| 7 | 112 ± 10 | 83 ± 14 | 91 ± 7.2 |
| 11 | 110 ± 15 | 76 ± 5.5 | 109 ± 11 |

Levels of circulating anti-hANGPTL4 antibodies ("serum human Ab") were also determined using a standard ELISA assay. Briefly, plates were coated with a goat anti-human Fc antibody (Sigma-Aldrich) to capture serum human Ab. Serum was then added to the plates and captured anti-hANGPTL4 antibodies were detected by chemiluminescence using a horseradish peroxidase (HRP)-conjugated goat anti-human IgG antibody (Sigma-Aldrich). Results, expressed as (mean±SEM) of serum human Ab, are shown in Table 17.

TABLE 17

| Days after injection | Serum Human Antibody (µg/mL) | | |
|---|---|---|---|
| | hIgG1 Control | H1H268P | H1H284P |
| −7 | 2.71 ± 2.18 | 2.92 ± 2.92 | 3.02 ± 2.38 |
| 1 | 24384 ± 911 | 24130 ± 1788 | 16459 ± 1455 |
| 4 | 22553 ± 1811 | 16557 ± 1369 | 9103 ± 767 |
| 7 | 13833 ± 467 | 12586 ± 1176 | 2428 ± 525 |
| 11 | 13145 ± 1598 | 6106 ± 1111 | 135 ± 38 |

Administration of H1H268P to humanized ANGPTL4 mice led to ~25-30% reduction in circulating TG 4-11 days after the antibody administration, compared to mice dosed with an isotype-matched control antibody. TG reduction resulting from H1H284P administration was most effective at day 4 after injection of the antibody (~34% in TG reduction), but by day 11 TG levels were increased back to control level, probably due to fast clearance rate of the antibody.

Example 11

In Vivo Effect of IgG4 Anti-hANGPTL4 Antibodies on Circulating TG Levels in Humanized ANGPTL4 Mice The effect of anti-hANGPTL4 antibodies, H4H268P2 and H4H284P, on serum TG levels was determined in humanized ANGPTL4 mice. Humanized ANGPTL4 mice were pre-bled 7 days before the experiment and put into groups of six mice each for each antibody tested. Antibodies (H4H268P2, H4H284P and isotype-matched (hIgG4) control with no known cross-reactivity to mouse antigens) were administered at 10 mg/kg dose by subcutaneous injection. Mice were bled after 4 hours of fasting at days 1, 4, 7 and 11 after antibody injection; and TG levels were determined in the serum by ADVIA® 1800 Chemistry System (Siemens). Average TG levels were calculated for each time point for each antibody. Results, expressed as (mean±SEM) of serum TG concentration, are shown in Table 18.

TABLE 18

| Days after injection | Serum TG (mg/dL) | | |
|---|---|---|---|
| | hIgG4 Control | H4H268P2 | H4H284P |
| −7 | 103 ± 9.5 | 101 ± 9.3 | 103 ± 8.0 |
| 1 | 118 ± 13 | 81 ± 6.8 | 86 ± 8.6 |
| 4 | 115 ± 9.8 | 67 ± 5.3 | 69 ± 6.4 |
| 7 | 81 ± 9.7 | 56 ± 7.1 | 71 ± 11 |
| 11 | 109 ± 10 | 87 ± 8.7 | 83 ± 7.3 |

Administration of H4H268P2 and H4H284P to humanized ANGPTL4 mice led to a significant reduction in circulating TG on day 1 (H4H268P2) and day 4 (H4H268P2 and H4H284P) after the antibodies administration, compared to mice dosed with isotype-matched control antibody.

Figure 4:
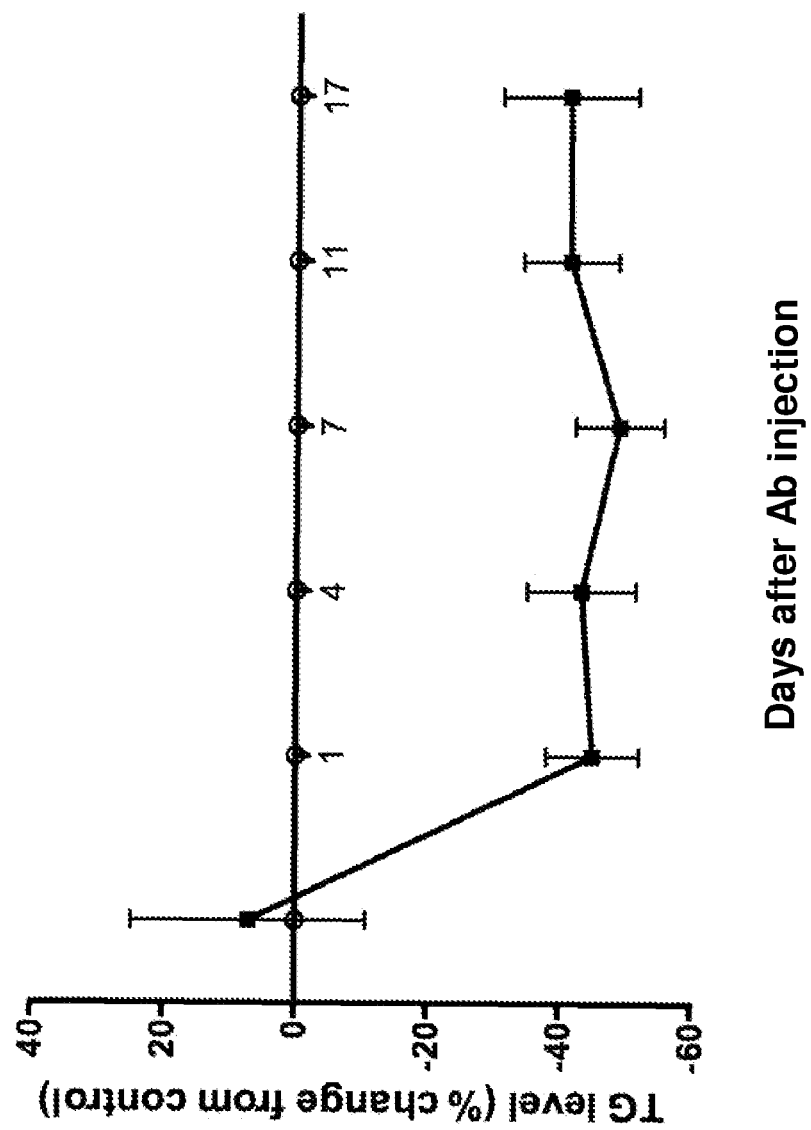
FIG. 4 shows the effect of anti-ANGPTL4 antibody, H4H268P2, on serum triglyceride (TG) levels in humanized ANGPTL4 mice crossed to ApoE null mice. Percent (%) changes of serum TG levels by H4H268P2, compared to control antibody with irrelevant specificity, are shown. Control Ab (○); and H4H268P2 (■).

The effect of H4H268P2 on circulating TG levels was further studied in humanized ANGPTL4 mice crossed to ApoE null mice. The ApoE null mouse model is known as a highly atherogenic and hyperlipidemic model with the majority of cholesterol and TG circulating in VLDL particles due to impaired VLDL remnant clearance. Humanized ANGPTL4× ApoE null mice were pre-bled 7 days before the experiment and put into 2 groups of six mice each. Antibodies H4H268P2 and Control Ab were administered at 10 mg/kg by subcutaneous injection. Mice were bled after 4 hours of fasting on days 1, 4, 7, 11 and 17 after antibody injection and TG levels were determined in the serum by ADVIA® 1800 Chemistry System (Siemens). TG reductions shown in FIG. 4 are expressed as a percent of TG levels compared to Control Ab.

TG levels were significantly reduced for all 17 days (more than 42%) with the greatest reduction at day 7 (~50%) after administration of H4H268P2, compared to mice dosed with Control Ab.

Example 12

Figure 5:
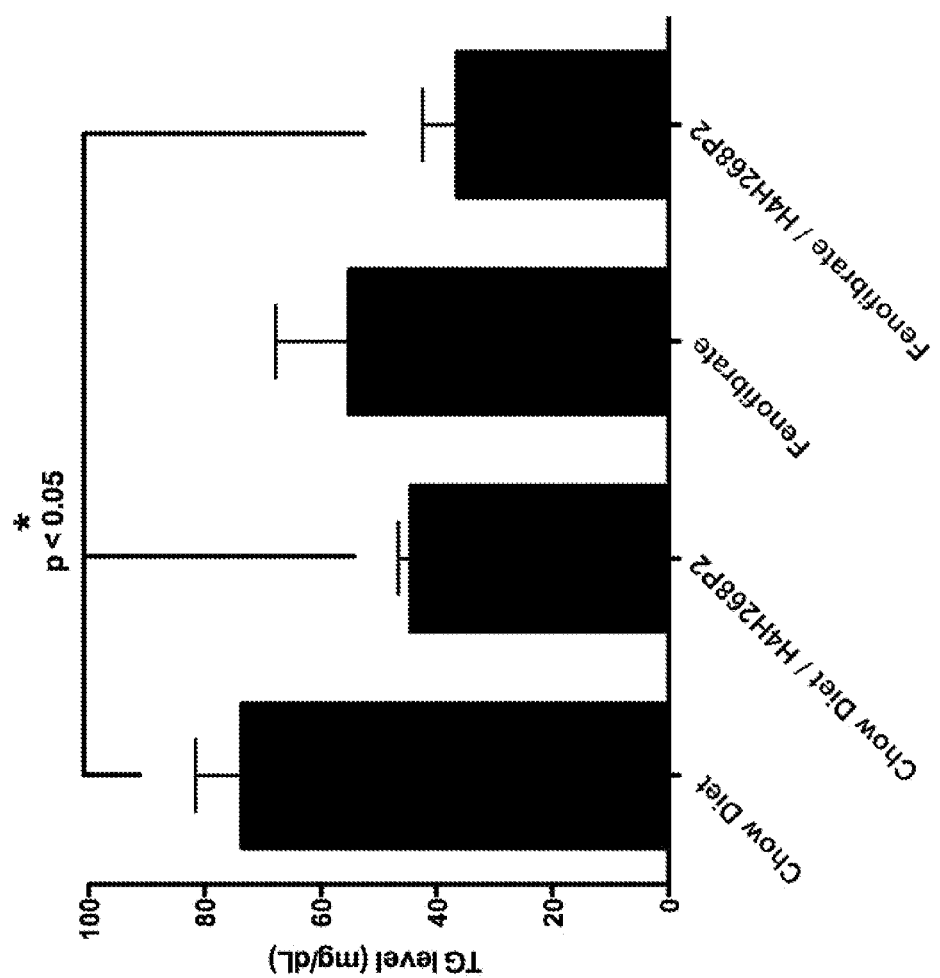
FIG. 5 shows the effects of anti-ANGPTL4 antibody H4H268P2 and TG-reducing drug fenofibrate, each alone or in combination, on serum TG levels in humanized ANGPTL4 mice.

In Vivo Effect of Anti-hANGPTL4 Antibodies in Combination with Fenofibrate on Serum TG Levels The effects of the anti-ANGPTL4 antibody H4H268P2 and TG-reducing drug fenofibrate, each alone or in combination, on serum TG levels were evaluated in humanized ANGPTL4 mice. The mice were pre-bled 7 days before the experiment after 4 hours of fasting and put into 4 groups of six mice each. Groups 2 and 4 were administered with H4H268P2 at 10 mg/kg by subcutaneous injection on day 0 and groups 1 (control group) and 2 were placed on regular chow diet. Groups 3 and 4 received chow diet supplemented with 0.05% (w/w) of fenofibrate (the dosage level was determined experimentally in a pilot study). Serum was collected from a terminal bleed on day 7 after H4H268P2 and/or fenofibrate administration (after 4 hours of fasting) and analyzed by ADVIA® 1800 Chemistry System (Siemens). The results are shown in FIG. 5.

Administration of H4H268P2 alone and in combination with fenofibrate led to significant reduction in circulating TG levels 7 days after administration. TG levels were reduced by ~40% (mean) 7 days after H4H268P2 administration alone, ~25% after fenofibrate treatment alone, and ~50% after combination treatment of H4H268P2 and fenofibrate, compared to control group treated with chow diet. H4H268P2 showed more efficacy than fenofibrate in reducing circulating TG levels in mouse models. Combination treatment showed a synergistic effect of H4H268P2 and fenofibrate on TG levels. Remarkably, livers collected from mice consumed fenofibrate (groups 3 and 4) for 7 days were significantly enlarged (1.8 times, liver weight/body weight), compared to mice consumed control chow diet (groups 1 and 2) (data not shown).

Example 13

Pilot Study on Pharmacokinetics/Pharmacodynamics of Anti-ANGPTL4 Antibodies in Obese Rhesus Monkeys Phase I: In a pilot non-GLP pharmacokinetics/pharmacodynamic (PK/PD) study, H4H268P2 and H4H284P were administered as a single bolus intravenous (IV) injection, to obese rhesus monkeys (*Macaca mulatta*). Rhesus monkeys were selected because this species is closely related, both phylogenically and physiologically, to humans and is a species commonly used for nonclinical toxicity evaluations. Obese monkeys that had been on a high fat diet for greater than 6 months were selected because they typically display moderately elevated TG levels (i.e., mean >100 mg/dL; hyper-TG). Eight confirmed healthy, male monkeys were acclimated and assigned to the study for baseline assessment for 7 days prior to dosing. All animals received a vehicle (10 mM histidine, pH 6) IV infusion on Day −5, after which four of them received H4H268P2 and another four H4H284P at 10 mg/kg IV on day 0. No injection site reactions or other adverse effects were observed at any time point after infusion.

Figure 6:
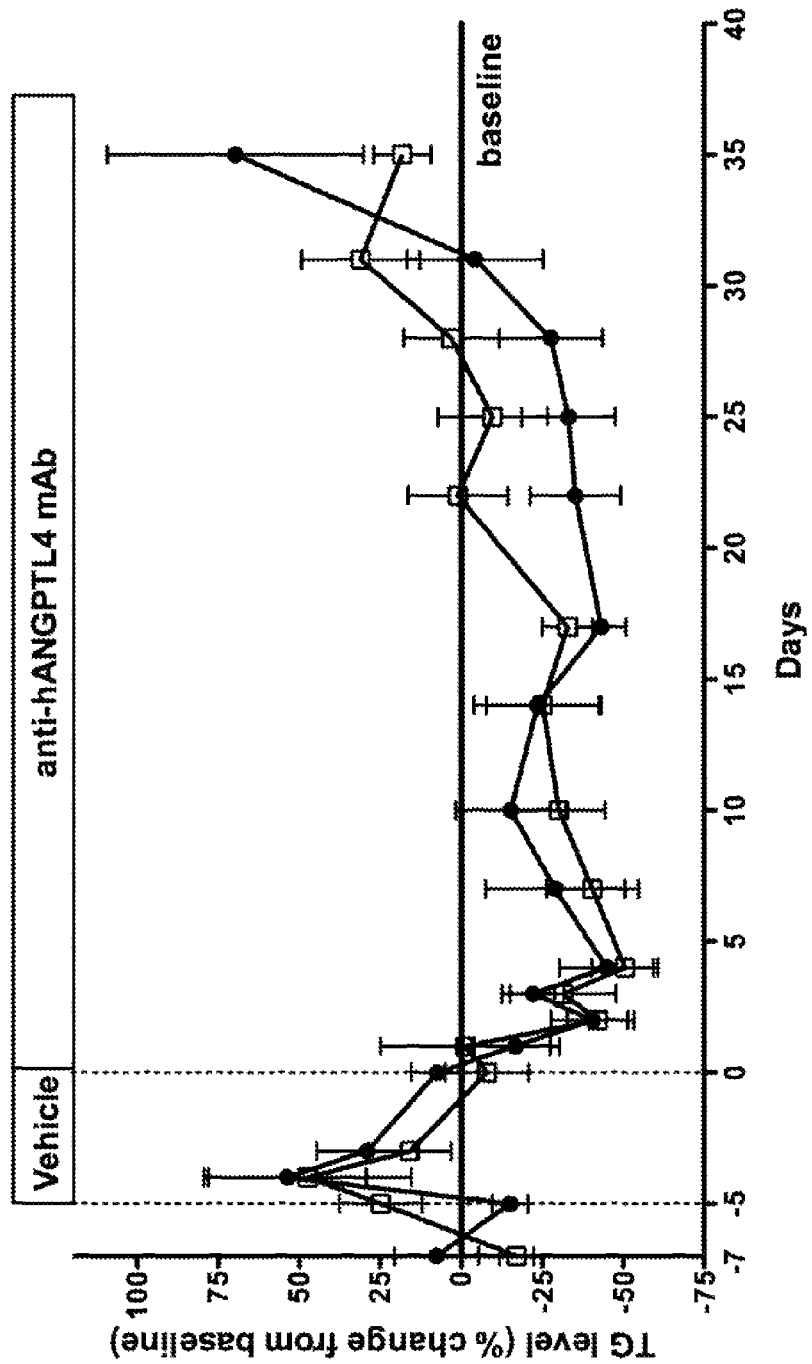
FIG. 6 shows the results of phase I pilot study on effects of anti-ANGPTL4 antibodies on fasting serum TG levels, among other lipids, in obese rhesus monkeys (*Macaca mulatta*). All monkeys received a vehicle (10 mM histidine, pH 6) intravenous (IV) infusion on Day −5 and either H4H268P2 (n=3) (●) or H4H284P (n=3) (□) at 10 mg/kg IV on Day O, Serum samples were collected from the baseline period through Day 35 post-dosing. The average baseline for each animal was determined based on the samples taken on Days −7, −5 and 0, and percent (%) changes of serum TG levels from the baseline determined and averaged for each Ab group.

Serum samples were collected from the baseline period through day 35 post-dosing and assessed for serum lipid levels by ADVIA® 1800 Chemistry System (Siemens). The average baseline for each animal was determined based on the samples taken on Days −7, −5 and 0. Preliminary analysis of samples taken after vehicle administration revealed that 3 obese animals from each group displayed elevated fasted TG levels (i.e., TG>100 mg/dL) while one animal from each group had an average TG level well within the normal range (i.e., mean fasting TG level of 42 mg/dL and 84 mg/dL). Thus the data analysis was done with 3 animals in each group. Percent (%) changes of serum TG levels from the baseline were determined for each animal and averaged for each Ab group. The results are shown in FIG. 6.

Administration of H4H268P2 to the three mildly hyper-TG animals showed a maximal reduction of 57% at day 4 post-dosing. The mean serum TG levels for these animals after H4H268P2 treatment remained at or below 100 mg/dL until approximately Day 25. Moderate effects were observed on additional lipids, such as LDL-cholesterol (LDL-C) and HDL-C; however total-C was unchanged (data not shown). Administration of H4H268P2 to the single obese animal with low TG levels did not yield any significant effect to lower fasting TG's or any other lipid parameters (data not shown), suggesting a lower limit for the reduction of TG levels by the antibody.

Phase II: In the second non-GLP pharmacokinetics/pharmacodynamic (PK/PD) study only H4H268P2 was administered as a single bolus intravenous (IV) injection to eight obese rhesus monkeys (*Macaca mulatta*). The step of pre-dosing vehicle injection was omitted in this study. Three baseline assessments were taken at days −7, −3 and 0 of the study and all eight monkeys received H4H268P2 at 10 mg/kg by IV on day 0, Serum samples were collected from the baseline period through day 35 post-dosing and assessed for serum lipid levels by ADVIA® 1800 Chemistry System (Siemens). Animals were grouped for data analysis according to average baseline TG levels so as to prospectively predict the effect: A. TG<150 mg/dL (n=3); B. 150 mg/dL<TG<500 mg/dL (n=4); and C. TG>1000 mg/dL (n=1).

Figure 7:
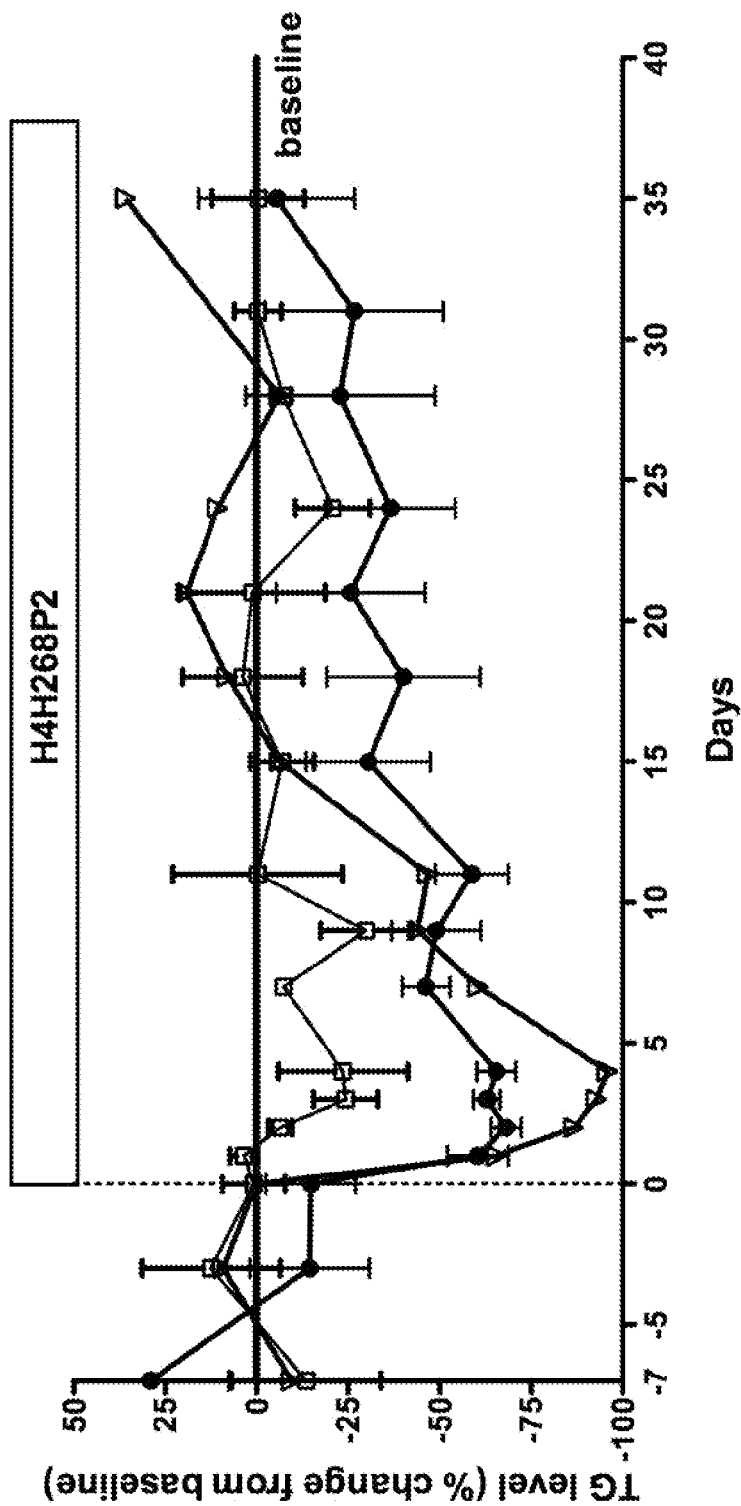
FIG. 7 shows the results of phase II pilot study on effects of anti-ANGPTL4 antibody H4H268P2 on fasting serum TG levels in obese monkeys, as described for FIG. 6, except that the step of vehicle infusion was omitted. The average baseline was obtained for each monkey based on the samples taken on Days −7, −3 and 0. Monkeys were divided into Groups based on their baselines: A. TG<150 mg/dL (n=3; □); B. 150 mg/dL<TG<500 mg/dL (n=4; ●); and C. TG>1000 mg/dL (n=1; ∇). Percent (%) changes of fasting TG levels from the baseline were determined for each monkey and averaged for each Group.

FIG. 7 shows the TG levels of the three groups expressed as percent changes of TG levels from the average of 3 baseline TG values. As expected on the basis of preclinical data, the greater reduction in fasting TG levels was seen in the animals with higher basal serum TG levels. An especially dramatic and rapid drop in TG level was observed in an individual animal whose baseline TG level was >1000 mg/dL. A robust decrease in TG levels (50-68%) was observed for animals with baseline 150 mg/dL<TG<500 mg/dL. In this group of obese monkeys administration of H4H268P2 increased HDL-C, but had no effect on LDL-C or Total-C (data not shown). Animals with baseline TG<150 mg/dL (normal TG levels) were largely unresponsive to H4H268P2.

We claim:

1. An isolated human antibody or antigen-binding fragment thereof that specifically binds human angiopoietin-like protein 4 (hANGPTL4), comprising three heavy chain complementarity determining regions, HCDR1, HCDR2 and HCDR3, and three light chain complementarity determining regions, LCDR1, LCDR2 and LCDR3, wherein the amino acid sequences of the HCDR1, HCDR2 and HCDR3 comprise SEQ ID NO:28, 30 and 32, respectively; and the amino acid sequences of the LCDR1, LCDR2 and LCDR3 comprise SEQ ID NO:36, 38 and 40, respectively.

2. The antibody or antigen-binding fragment of claim 1, comprising a heavy chain variable region (HCVR) comprising an amino acid sequence selected from the group consisting of SEQ ID NO:487, 42, 26 and 46.

3. The antibody or antigen-binding fragment of claim 1, comprising a light chain variable region (LCVR) comprising an amino acid sequence selected from the group consisting of SEQ ID NO:44, 34 and 48.

4. The antibody or antigen-binding, fragment of claim 1, comprising a HCVR/LCVR sequence pair selected from the group consisting of SEQ ID NO:487/44, 42/44, 26/34 and 46/48.

5. A pharmaceutical composition comprising the antibody or antigen-binding fragment of claim 4 and a pharmaceutically acceptable carrier.

6. A pharmaceutical composition comprising the antibody or antigen-binding fragment of claim 1 and a pharmaceutically acceptable carrier.

* * * * *